(12) United States Patent
Pestka et al.

(10) Patent No.: US 6,287,853 B1
(45) Date of Patent: Sep. 11, 2001

(54) ACCESSORY FACTORY FUNCTION FOR INTERFERON GAMMA AND ITS RECEPTOR

(75) Inventors: Sidney Pestka, North Caldwell; Serguei Kotenko, Highland Park; Jaemog Soh, Highland Park; Robert J. Donnelly, Highland Park; Thomas M. Mariano, Somerset; Jeffry R. Cook, Kendall Park; Stuart Emanuel, New Brunswick; Barbara Schwartz, Annandale, all of NJ (US)

(73) Assignee: University of Medicine & Dentistry of New Jersey, Newark, NJ (US)

( * ) Notice: Subject to any disclaimer, the term of this patent is extended or adjusted under 35 U.S.C. 154(b) by 0 days.

(21) Appl. No.: 08/871,572

(22) Filed: Jun. 9, 1997

Related U.S. Application Data

(60) Continuation of application No. 08/444,134, filed on May 18, 1995, now abandoned, which is a division of application No. 08/110,119, filed on Aug. 20, 1993, now abandoned.

(51) Int. Cl.$^7$ .............................. C12N 15/63; C12N 1/21; C07K 14/435
(52) U.S. Cl. ................. 435/320.1; 435/243; 435/252.33; 530/350
(58) Field of Search .................................. 435/69.1, 325, 435/254.11, 252.3; 530/350; 536/235

(56) References Cited

PUBLICATIONS

George et al., Macromolecular Sequencing and Synthesis, 127–149, 1988.*
Boctor et al Federation Proceedings 41(4): 5220 (1982).*
Greenlund et al. *J. Biol Chem* 268(24):18103–18110 (1993).*
Metzger et al *J. Biol Chem* 265(17):9978–83 (1990).*
Nagpal et al. *EMBO J.* 12(6):2349–60 (1993).*
Reeck et al., Cell, 50, 667, 1987.*
Lewin, Science, 237, Sep. 25, 1987.*
Kalina et al., J. of Virology, 1993, vol. 67, 1702–1706.*
Chumakov et al., Nature, 1992, vol. 359, 380–387.*
Sambrook et al., Molecular Cloning, A Laboratory Manual, vol. 3, 17.10–1728, 1989, CSH Laboratory Press.*

* cited by examiner

*Primary Examiner*—Christine J. Saoud
(74) *Attorney, Agent, or Firm*—Richard R. Muccino

(57) ABSTRACT

This invention relates (a) to a 540 kb YAC which encodes the necessary species-specific factor(s) and is able to substitute for human Chromosome 21 to reconstitute the Hu-IFN-gamma receptor-mediated induction of class I HLA antigens; (b) to the construction of a plasmid to integrate the selective marker for antibiotic G418 resistance into YACs and to delete some of the human DNA fragments from YACs in order to facilitate the manipulation of human genomic DNA in yeast artificial chromosome (YAC) clones; (c) to two fragmentation vectors, pSE1 and pSE2, which contain a neomycin resistance and URA3 gene, developed for targeting yeast artificial chromosomes (YACs) containing human genomic DNA; (d) to a chromosomal fragmentation procedure employed to produce a deletion set of yeast artificial chromosomes (YACs) from a parental YAC (GART D142H8) known to map to Chromosome 21q and to encode the human interferon-gamma receptor (Hu-IFN-gamma R) accessory factor gene as well as the phosphoribosylglycinamide formyltranisferase (GART) gene; and (e) to the isolation of cDNA clones that encode the necessary species-specific factor and that are able to substitute for human Chromosome 21 to reconstitute the Hu-IFN-gamma receptor-mediated induction of class I HLA antigens.

5 Claims, 24 Drawing Sheets

Figure 7
Fig 7A
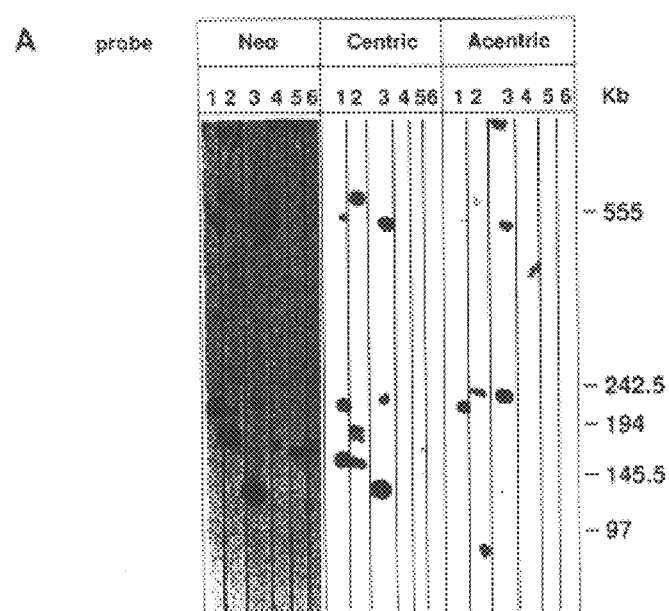
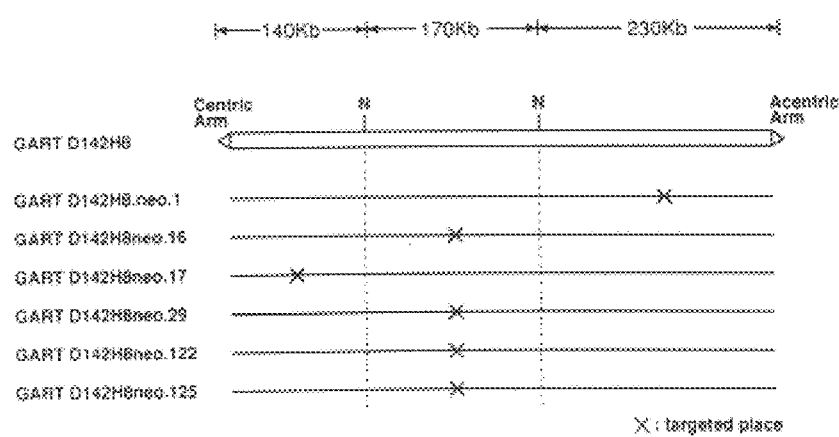
Fig 7B

Figure 9
Fig 9A
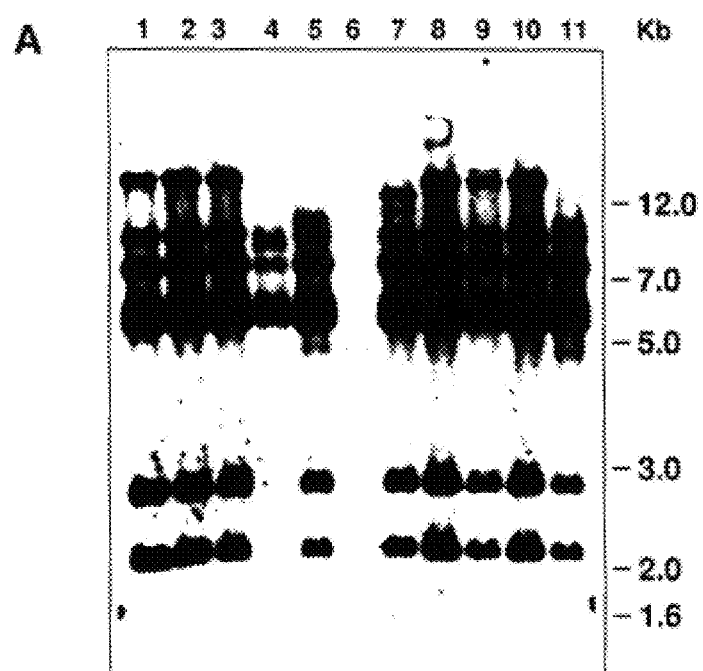
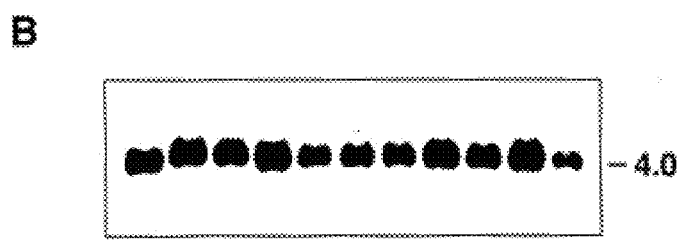
Fig 9B

Figure 13

| YAC | 0    100    200    300    400    500    600 kb | MHC Induction |
|---|---|---|
| GART | •—————————————————————————• | + |
| J29 | •———————————————————————• | + |
| J28 | •——————————————————————• | + |
| J16 | •——————————————• | + |
| J18 | •———————• | + |
| J20 | •—————• | − |
| J6 | •——• | − |

Figure 16
Fig 16 A
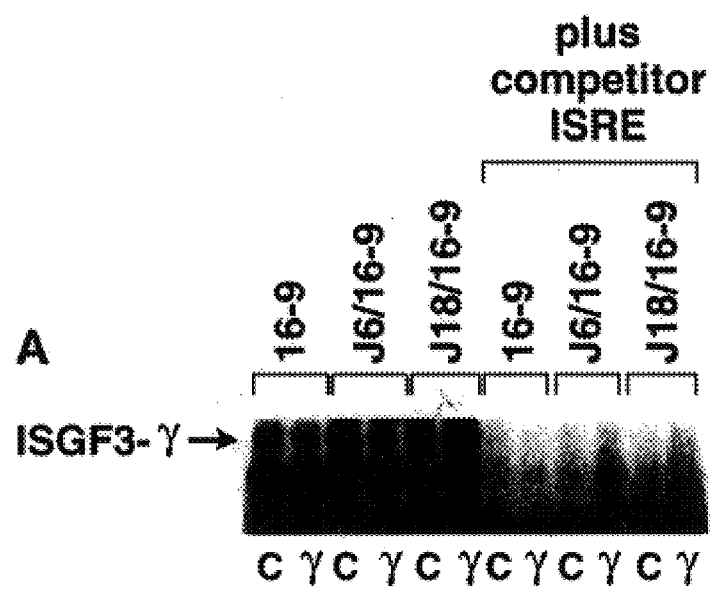
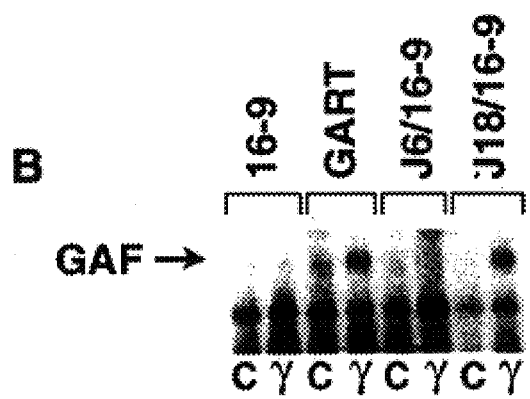
Fig 16B

Restriction Map for the Human IFN-γ Receptor
Accessory Factor-1 (Plasmid pSK1)

Figure 21

Sequence of Accessory Factor-1 for the Human
IFN-γ Receptor (Plasmid pSK1)

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 337 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:1:

```
Met Arg Pro Thr Leu Leu Trp Ser Leu Leu Leu Leu Gly Val Phe
 1               5                  10                  15

Ala Ala Ala Ala Ala Ala Pro Pro Asp Pro Leu Ser Gln Leu Pro Ala
                20                  25                  30

Pro Gln His Pro Lys Ile Arg Leu Tyr Asn Ala Glu Gln Val Leu Ser
                35                  40                  45

Trp Glu Pro Val Ala Leu Ser Asn Ser Thr Arg Pro Val Val Tyr Gln
     50                  55                  60

Val Gln Phe Lys Tyr Thr Asp Ser Lys Trp Phe Thr Ala Asp Ile Met
 65                  70                  75                  80

Ser Ile Gly Val Asn Cys Thr Gln Ile Thr Ala Thr Glu Cys Asp Phe
                85                  90                  95
```

```
Thr Ala Ala Ser Pro Ser Ala Gly Phe Pro Met Asp Phe Asn Val Thr
            100                 105                 110
Leu Arg Leu Arg Ala Glu Leu Gly Ala Leu His Ser Ala Trp Val Thr
            115                 120                 125
Met Pro Trp Phe Gln His Tyr Arg Asn Val Thr Val Gly Pro Pro Glu
            130                 135                 140
Asn Ile Glu Val Thr Pro Gly Glu Gly Ser Leu Ile Ile Arg Phe Ser
145                 150                 155                 160
Ser Pro Phe Asp Ile Ala Asp Thr Ser Thr Ala Phe Phe Cys Tyr Tyr
                165                 170                 175
Val His Tyr Trp Glu Lys Gly Gly Ile Gln Gln Val Lys Gly Pro Phe
            180                 185                 190
Arg Ser Asn Ser Ile Ser Leu Asp Asn Leu Lys Pro Ser Arg Val Tyr
            195                 200                 205
Cys Leu Gln Val Gln Ala Gln Leu Leu Trp Asn Lys Ser Asn Ile Phe
210                 215                 220
Arg Val Gly His Leu Ser Asn Ile Ser Cys Tyr Glu Thr Met Ala Asp
225                 230                 235                 240
Ala Ser Thr Glu Leu Gln Gln Val Ile Leu Ile Ser Val Gly Thr Phe
                245                 250                 255
Ser Leu Leu Ser Val Leu Ala Gly Ala Cys Phe Phe Leu Val Leu Lys
            260                 265                 270
Tyr Arg Gly Leu Ile Lys Tyr Trp Phe His Thr Pro Pro Ser Ile Pro
            275                 280                 285
Leu Gln Ile Glu Glu Tyr Leu Lys Asp Pro Thr Gln Pro Ile Leu Glu
            290                 295                 300
Ala Leu Asp Lys Asp Ser Ser Pro Lys Asp Asp Val Trp Asp Ser Val
305                 310                 315                 320
Ser Ile Ile Ser Phe Pro Glu Lys Glu Gln Glu Asp Val Leu Gln Thr
                325                 330                 335
Leu (2) INFORMATION FOR SEQ ID NO:2:

(i) SEQUENCE CHARACTERISTICS:
        (A) LENGTH: 1566 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:2:

AGCCCCGGGG CCATGCGACC GACGCTGCTG TGGTCGCTGC TGCTGCTGCT CGGAGTCTTC      60

GCCGCCGCCG CCGCGGCCCC GCCAGACCCT CTTTCCCAGC TGCCCGCTCC TCAGCACCCG    120

AAGATTCGCC TGTACAACGC AGAGCAGGTC CTGAGTTGGG AGCCAGTGGC CCTGAGCAAT    180

AGCACGAGGC CTGTTGTCTA CCAAGTGCAG TTTAAATACA CCGACAGTAA ATGGTTCACG    240

GCCGACATCA TGTCCATAGG GGTGAATTGT ACACAGATCA CAGCAACAGA GTGTGACTTC    300

ACTGCCGCCA GTCCCTCAGC AGGCTTCCCA ATGGATTTCA ATGTCACTCT ACGCCTTCGA    360

GCTGAGCTGG GAGCACTCCA TTCTGCCTGG GTGACAATGC CTTGGTTTCA ACACTATCGG    420

AATGTGACTG TCGGGCCTCC AGAAAACATT GAGGTGACCC CAGGAGAAGG CTCCCTCATC    480
```

-continued

```
ATCAGGTTCT CCTCTCCCTT TGACATCGCT GATACCTCCA CGGCCTTTTT TTGTTATTAT      540

GTCCATTACT GGGAAAAAGG AGGAATCCAA CAGGTCAAAG GCCCTTTCAG AAGCAACTCC      600

ATTTCATTGG ATAACTTAAA ACCCTCCAGA GTGTACTGTT TACAAGTCCA GGCACAACTG      660

CTTTGGAACA AAAGTAACAT CTTTAGAGTC GGGCATTTAA GCAACATATC TTGCTACGAA      720

ACAATGGCAG ATGCCTCCAC TGAGCTTCAG CAAGTCATCC TGATCTCCGT GGGAACATTT      780

TCGTTGCTGT CGGTGCTGGC AGGAGCCTGT TTCTTCCTGG TCCTGAAATA TAGAGGCCTG      840

ATTAAATACT GGTTTCACAC TCCACCAAGC ATCCCATTAC AGATAGAAGA GTATTTAAAA      900

GACCCAACTC AGCCCATCTT AGAGGCCTTG ACAAGGACA GCTCACCAAA GGATGACGTC       960

TGGGACTCTG TGTCCATTAT CTCGTTTCCG GAAAAGGAGC AAGAAGATGT TCTCCAAACG     1020

CTTTGAACCA AGCATGGGC CTAGCCCACT GGCTCCCTGG AAGAGATCAA GCCATCGGAG     1080

CTGCTAGAGT TCTGTCTGGA CTTTCCAGAG ACCAGTATTC CCTTTTGCTG CCTCTAAAAG    1140

GCCTGTCCCT GCAGACATGA GAGACAGCAG GTCTCATGGG GGTGACAAGC TTTTTTTTTT    1200

TTTTCTTAAA GAATTTTCAA AATCAAATTC CAGAATGATT TTACGGAGAT ATCCCAGGAA    1260

AATTAAGGCT TCTCTTAAAC ACTAAAAAGG CATGTAATTG CTTGTTAGCA AAATGGATAT    1320

GACACATCTC TGATACTTTT TTCATTATTG GTTGGGCTGA GCAGTCAGAA GACCTGGTCG    1380

TCGTCTTGAC TTTGGCAAAT GAGCCGGAGC CCCTTGCGAG GTCACACAAC CTGTCCCAGC    1440

GAGGGACACT GAGTGGCCTT CATGTACATC CATGGTGTGC TGGCTTAAAA TGTAATTAAT    1500

CTTGTAAATA TACTCCTAGT AATTTAAGAT TTTGTTTTTA AACTGGAAAT AAAAGATTGT    1560

ATAGTG                                                              1566

(2) INFORMATION FOR SEQ ID NO:3:

(i) SEQUENCE CHARACTERISTICS:
        (A) LENGTH: 2255 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:3:

GTTGACTGGA GGCGGAGGTT GCAGTGAGCC GAGATCGCCC CACTGCACTC CAGCCTGGTG       60

ACTCCGTCTC AAAAAAAAGG GGAGGGGGGC GGGGAGAGT TGAAAGCTTA ATATGTACTT      120

TGGGGCTAT TAAAGCAAAC ATTTCGACTA AAGGGGCGAA TCCTCGAATT GTGCGATCAA      180

GCCACCGAGA GGAGAGTTGG GGGGGGTCAG GAGGGGTGGG GGCTCCAGGG AACGCCCGGG      240

GGCCTGGGCC GGGGTCTCGC GGGGCCCTTC CGGAAGGATC GCGGCCCCCG AAGGTGGCGG      300

TCCCGCGGGG CTCCAGTCTC CAGGACGTTC CGGGAGGCTC CGCGCTCTGG GAGGCCGGCT      360

GCGTGGGGTC CCCGCGCTGC AGCCGCAGAG GCCCCCCAGG GCCGCGGTTC CCGGAGCGGG      420

AAAGTCCCGC GCGGGGCGG TGGCCTCGGG GGCGGGACGG GGCGGGGCG GGGGCGCGGG       480

CGGCCGAGCC GAATCCCCTC CACCGGGACG CCCCGCTGCC GCTCGGGAAG AGGCGGGCCC      540

TGCGCGCCCT GCGCTCGCCA TGGCGGTTTG GGCGGCGACG TGAGCGGCTC CGCGGACCCC      600

GAGCGGGGCC CCGGCCGCGA CCTGAGCCGC CGCCGAGCGC CCGGGGCCAT GCGACCGACG      660

CTGCTGTGGT CGCTGCTGCT GCTGCTCGGA GTCTTCGCCG CCGCCGCCGC GGCCCCGCCA      720
```

| | |
|---|---|
| GACCCTCTTT CCCAGCTGCC CGCTCCTCAG CACCCGAAGA TTCGCCTGTA CAACGCAGAG | 780 |
| CAGGTCCTGA GTTGGGAGCC AGTGGCCCTG AGCAATAGCA CGAGGCCTGT TGTCTACCGA | 840 |
| GTGCAGTTTA AATACACCGA CAGTAAATGG TTCACGGCCG ACATCATGTC CATAGGGGTG | 900 |
| AATTGTACAC AGATCACAGC AACAGAGTGT GACTTCACTG CCGCCAGTCC CTCAGCAGGC | 960 |
| TTCCCAATGG ATTTCAATGT CACTCTACGC CTTCGAGCTG AGCTGGGAGC ACTCCATTCT | 1020 |
| GCCTGGGTGA CAATGCCTTG GTTTCAACAC TATCGGAATG TGACTGTCGG GCCTCCAGAA | 1080 |
| AACATTGAGG TGACCCCAGG AGAAGGCTCC CTCATCATCA GGTTCTCCTC TCCCTTTGAC | 1140 |
| ATCGCTGATA CCTCCACGGC CTTTTTTTGT TATTATGTCC ATTACTGGGA AAAAGGAGGA | 1200 |
| ATCCAACAGG TCAAAGGCCC TTTCAGAAGC AACTCCATTT CATTGGATAA CTTAAAACCC | 1260 |
| TCCAGAGTGT ACTGTTTACA AGTCCAGGCA CAACTGCTTT GGAACAAAAG TAACATCTTT | 1320 |
| AGAGTCGGGC ATTTAAGCAA CATATCTTGC TACGAAACAA TGGCAGATGC CTCCACTGAG | 1380 |
| CTTCAGCAAG TCATCCTGAT CTCCGTGGGA ACATTTTCGT TGCTGTCGGT GCTGGCAGGA | 1440 |
| GCCTGTTTCT TCCTGGTCCT GAAATATAGA GGCCTGATTA ATACTGGTT TCACACTCCA | 1500 |
| CCAAGCATCC CATTACAGAT AGAAGAGTAT TTAAAAGACC CAACTCAGCC CATCTTAGAG | 1560 |
| GCCTTGGACA AGGACAGCTC ACCAAAGGAT GACGTCTGGG ACTCTGTGTC CATTATCTCG | 1620 |
| TTTCCGGAAA AGGAGCAAGA AGATGTTCTC CAAACGCTTT GAACCAAAGC ATGGGCCTAG | 1680 |
| CCCACTGGCT CCCTGGAAGA GATCAAGCCA TCGGAGCTGC TAGAGTTCTG TCTTGGACTT | 1740 |
| TCCAGAGACC AGTATTCCCT TTTTGCTGCC TCTAAAAGGC CTGTCCCTGC AGACATGAGA | 1800 |
| GACAGCAGGT CTCATGGGGG TGACAAGCTT TTTTTTTTTT TTCTTAAAGA ATTTTCAAAA | 1860 |
| TCAAATTCCA GAATGATTTT ACGGAGATAT CCCAGGAAAA TTAAGGCTTC TCTTAAACAC | 1920 |
| TAAAAAGGCA TGTAATTGCT TGTTAGCAAA ATGGATATGA CACATCTCTG ATACTTTTTT | 1980 |
| CATTATTGGT TGGGCTGAGC AGTCAGAAGA CCTGGTCGTC GTCTTGACTT TGGCAAATGA | 2040 |
| GCCGGAGCCC CTTGGGCAGG TCACACAACC TGTCCCAGCG AGGGACACTG AGTGGCCCTT | 2100 |
| CATGTACATC CATGGTGTGC TGGCTTAAAA TGTAATTAAT CTTGTAAATA TACTCCTAGT | 2160 |
| AATTTAAGAT TTTGTTTTTA AACTGGAAAT AAAAGATTGT ATAGTGCATG TTTTTTAAAA | 2220 |
| AAAAAAAAAA AAAAAAAAAA AAAAAAAAAA AAAAA | 2255 |

(2) INFORMATION FOR SEQ ID NO:4:

(i) SEQUENCE CHARACTERISTICS:
        (A) LENGTH: 337 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:4:

```
Met Arg Pro Thr Leu Leu Trp Ser Leu Leu Leu Leu Gly Val Phe
1               5                   10                  15

Ala Ala Ala Ala Ala Ala Pro Pro Asp Pro Leu Ser Gln Leu Pro Ala
                20                  25                  30

Pro Gln His Pro Lys Ile Arg Leu Tyr Asn Ala Glu Gln Val Leu Ser
            35                  40                  45
```

-continued

```
Trp Glu Pro Val Ala Leu Ser Asn Ser Thr Arg Pro Val Val Tyr Arg
     50                  55                  60

Val Gln Phe Lys Tyr Thr Asp Ser Lys Trp Phe Thr Ala Asp Ile Met
 65                  70                  75                  80

Ser Ile Gly Val Asn Cys Thr Gln Ile Thr Ala Thr Glu Cys Asp Phe
                     85                  90                  95

Thr Ala Ala Ser Pro Ser Ala Gly Phe Pro Met Asp Phe Asn Val Thr
                100                 105                 110

Leu Arg Leu Arg Ala Glu Leu Gly Ala Leu His Ser Ala Trp Val Thr
                115                 120                 125

Met Pro Trp Phe Gln His Tyr Arg Asn Val Thr Val Gly Pro Pro Glu
    130                 135                 140

Asn Ile Glu Val Thr Pro Gly Glu Gly Ser Leu Ile Ile Arg Phe Ser
145                 150                 155                 160

Ser Pro Phe Asp Ile Ala Asp Thr Ser Thr Ala Phe Phe Cys Tyr Tyr
                165                 170                 175

Val His Tyr Trp Glu Lys Gly Gly Ile Gln Gln Val Lys Gly Pro Phe
                180                 185                 190

Arg Ser Asn Ser Ile Ser Leu Asp Asn Leu Lys Pro Ser Arg Val Tyr
    195                 200                 205

Cys Leu Gln Val Gln Ala Gln Leu Leu Trp Asn Lys Ser Asn Ile Phe
    210                 215                 220

Arg Val Gly His Leu Ser Asn Ile Ser Cys Tyr Glu Thr Met Ala Asp
225                 230                 235                 240

Ala Ser Thr Glu Leu Gln Gln Val Ile Leu Ile Ser Val Gly Thr Phe
                245                 250                 255

Ser Leu Leu Ser Val Leu Ala Gly Ala Cys Phe Phe Leu Val Leu Lys
                260                 265                 270

Tyr Arg Gly Leu Ile Lys Tyr Trp Phe His Thr Pro Pro Ser Ile Pro
    275                 280                 285

Leu Gln Ile Glu Glu Tyr Leu Lys Asp Pro Thr Gln Pro Ile Leu Glu
    290                 295                 300

Ala Leu Asp Lys Asp Ser Ser Pro Lys Asp Asp Val Trp Asp Ser Val
305                 310                 315                 320

Ser Ile Ile Ser Phe Pro Glu Lys Glu Gln Glu Asp Val Leu Gln Thr
                325                 330                 335

Leu
```

(2) INFORMATION FOR SEQ ID NO:5:

(i) SEQUENCE CHARACTERISTICS:
        (A) LENGTH: 258 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:5:

```
Met Arg Pro Thr Leu Leu Trp Ser Leu Leu Leu Leu Gly Val Phe
 1               5                  10                  15

Ala Ala Ala Ala Ala Ala Pro Asp Pro Leu Ser Gln Leu Pro Ala
                20                  25                  30
```

```
Pro Gln His Pro Lys Ile Arg Leu Tyr Asn Ala Glu Gln Val Leu Ser
        35                  40                  45

Trp Glu Pro Val Ala Leu Ser Asn Ser Thr Arg Pro Val Val Tyr Arg
 50                  55                  60

Val Gln Phe Lys Tyr Thr Asp Ser Lys Trp Phe Thr Ala Asp Ile Met
 65                  70                  75                  80

Ser Ile Gly Val Asn Cys Thr Gln Ile Thr Ala Thr Glu Cys Asp Phe
                 85                  90                  95

Thr Ala Ala Ser Pro Ser Ala Gly Phe Pro Met Asp Phe Asn Val Thr
                100                 105                 110

Leu Arg Leu Arg Ala Glu Leu Gly Ala Leu His Ser Ala Trp Val Thr
            115                 120                 125

Met Pro Trp Phe Gln His Tyr Arg Asn Val Thr Val Gly Pro Pro Glu
        130                 135                 140

Asn Ile Glu Val Thr Pro Gly Glu Gly Ser Leu Ile Ile Arg Phe Ser
145                 150                 155                 160

Ser Pro Phe Asp Ile Ala Asp Thr Ser Thr Ala Phe Phe Cys Tyr Tyr
                165                 170                 175

Val His Tyr Trp Glu Lys Gly Gly Ile Gln Gln Val Lys Gly Pro Phe
            180                 185                 190

Arg Ser Asn Ser Ile Ser Leu Asp Asn Leu Lys Pro Ser Arg Val Tyr
            195                 200                 205

Cys Leu Gln Val Gln Ala Gln Leu Leu Trp Asn Lys Ser Asn Ile Phe
210                 215                 220

Arg Val Gly His Leu Ser Asn Ile Ser Cys Tyr Glu Thr Met Ala Asp
225                 230                 235                 240

Ala Ser Thr Glu Leu Gln Gln Val Ile Leu Ile Ser Val Gly Thr Phe
                245                 250                 255

Ser Leu (2) INFORMATION FOR SEQ ID NO:6:

(i) SEQUENCE CHARACTERISTICS:
        (A) LENGTH: 259 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:6:

Met Ala Leu Leu Phe Leu Leu Pro Leu Val Met Gln Gly Val Ser Arg
 1               5                  10                  15

Ala Glu Met Gly Thr Ala Asp Leu Gly Pro Ser Ser Val Pro Thr Pro
                20                  25                  30

Thr Asn Val Thr Ile Glu Ser Tyr Asn Met Asn Pro Ile Val Tyr Trp
            35                  40                  45

Glu Tyr Gln Ile Met Pro Gln Val Pro Val Phe Thr Val Glu Val Lys
 50                  55                  60

Asn Tyr Gly Val Lys Asn Ser Glu Trp Ile Asp Ala Cys Ile Asn Ile
 65                  70                  75                  80

Ser His His Tyr Cys Asn Ile Ser Asp His Val Gly Asp Pro Ser Asn
                 85                  90                  95
```

```
Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
            115                 120                 125

Pro Pro Lys Leu Asp Ile Arg Lys Glu Glu Lys Gln Ile Met Ile Asp
130             135                 140

Ile Phe His Pro Ser Val Phe Val Asn Gly Asp Glu Gln Glu Val Asp
145             150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
            195                 200                 205

Leu Asn Ser Gln Tyr Cys Val Ser Ala Glu Gly Val Leu His Val Trp
            210                 215                 220

Gly Val Thr Thr Glu Lys Ser Lys Glu Val Cys Ile Thr Ile Phe Asn
225             230                 235                 240

Ser Ser Ile Lys Gly Ser Leu Trp Ile Pro Val Val Ala Ala Leu Leu
                245                 250                 255

Leu Phe Leu (2) INFORMATION FOR SEQ ID NO:7:

(i) SEQUENCE CHARACTERISTICS:
        (A) LENGTH: 267 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:7:

Met Gly Pro Gln Ala Ala Ala Gly Arg Met Ile Leu Leu Val Val Leu
1               5                   10                  15

Met Leu Ser Ala Lys Val Gly Ser Gly Ala Leu Thr Ser Thr Glu Asp
            20                  25                  30

Pro Glu Pro Pro Ser Val Pro Val Pro Thr Asn Val Leu Ile Lys Ser
            35                  40                  45

Tyr Asn Leu Asn Pro Val Val Cys Trp Glu Tyr Gln Asn Met Ser Gln
50              55                  60

Thr Pro Ile Phe Thr Val Gln Val Lys Val Tyr Ser Gly Ser Trp Thr
65              70                  75                  80

Asp Ser Cys Thr Asn Ile Ser Asp His Cys Cys Asn Ile Tyr Gly Gln
            85                  90                  95

Ile Met Tyr Pro Asp Val Ser Ala Trp Ala Arg Val Lys Ala Lys Val
            100                 105                 110

Gly Gln Lys Glu Ser Asp Tyr Ala Arg Ser Lys Glu Phe Leu Met Cys
            115                 120                 125

Leu Lys Gly Lys Val Gly Pro Pro Gly Leu Glu Ile Arg Arg Lys Lys
            130                 135                 140

Glu Glu Gln Leu Ser Val Leu Val Phe His Pro Glu Val Val Val Asn
145             150                 155                 160
```

```
Gly Glu Ser Gln Gly Thr Met Phe Gly Asp Gly Ser Thr Cys Tyr Thr
                165                 170                 175

Phe Asp Tyr Thr Val Tyr Val Glu His Asn Arg Ser Gly Glu Ile Leu
                180                 185                 190

His Thr Lys His Thr Val Glu Lys Glu Glu Cys Asn Glu Thr Leu Cys
                195                 200                 205

Glu Leu Asn Ile Ser Val Ser Thr Leu Asp Ser Arg Tyr Cys Ile Ser
            210                 215                 220

Val Asp Gly Ile Ser Ser Phe Trp Gln Val Arg Thr Glu Lys Ser Lys
225                 230                 235                 240

Asp Val Cys Ile Pro Pro Phe His Asp Asp Arg Lys Asp Ser Ile Trp
                245                 250                 255

Ile Leu Val Val Ala Pro Leu Thr Val Phe Thr
                260                 265

(2) INFORMATION FOR SEQ ID NO:8:

(i) SEQUENCE CHARACTERISTICS:
        (A) LENGTH: 233 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:8:

Met Ala Trp Ser Leu Gly Ser Trp Leu Gly Gly Cys Leu Leu Val Ser
1               5                   10                  15

Ala Leu Gly Met Val Arg Pro Pro Glu Asn Val Arg Met Asn Ser Val
                20                  25                  30

Asn Phe Lys Asn Ile Leu Gln Trp Glu Ser Pro Ala Phe Ala Lys Gly
            35                  40                  45

Asn Leu Thr Phe Thr Ala Gln Tyr Leu Ser Tyr Arg Ile Phe Gln Asp
        50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
                100                 105                 110

Ile Gly Pro Pro Gly Met Gln Val Glu Val Leu Ala Asp Ser Leu His
            115                 120                 125

Met Arg Phe Leu Ala Pro Lys Ile Glu Asn Glu Tyr Glu Thr Trp Thr
130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Pro Asn Lys Ala Gly Glu Trp Ser Glu Pro Val
        195                 200                 205

Cys Glu Gln Thr Thr His Asp Glu Thr Val Pro Ser Trp Met Val Ala
210                 215                 220
```

```
Val Ile Leu Met Ala Ser Val Phe Met
225                 230
```

(2) INFORMATION FOR SEQ ID NO:9:

(i) SEQUENCE CHARACTERISTICS:
        (A) LENGTH: 224 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:9:

```
Met Met Val Val Leu Leu Gly Ala Thr Thr Leu Val Leu Val Ala Val
1               5                   10                  15

Gly Pro Trp Val Leu Ser Ala Ala Gly Gly Lys Asn Leu Lys Ser
            20                  25                  30

Pro Gln Lys Val Glu Val Asp Ile Ile Asp Asp Asn Phe Ile Leu Arg
            35                  40                  45

Trp Asn Arg Ser Asp Glu Ser Val Gly Asn Val Thr Phe Ser Phe Asp
50                      55                  60

Tyr Gln Lys Thr Gly Met Asp Asn Trp Ile Lys Leu Ser Gly Cys Gln
65                  70                      75                  80

Asn Ile Thr Ser Thr Lys Cys Asn Phe Ser Ser Leu Lys Leu Asn Val
                85                  90                  95

Tyr Glu Glu Ile Lys Leu Arg Ile Arg Ala Glu Lys Glu Asn Thr Ser
                100                 105                 110

Ser Trp Tyr Glu Val Asp Ser Phe Thr Pro Phe Arg Lys Ala Gln Ile
            115                 120                 125

Gly Pro Pro Glu Val His Leu Glu Ala Glu Asp Lys Ala Ile Val Ile
130                 135                 140

His Ile Ser Pro Gly Thr Lys Asp Ser Val Met Trp Ala Leu Asp Gly
145                 150                 155                 160

Leu Ser Phe Thr Tyr Ser Leu Leu Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190

Ser Pro Glu Thr Thr Tyr Cys Leu Lys Val Lys Ala Ala Leu Leu Thr
            195                 200                 205

Ser Trp Lys Ile Gly Val Tyr Ser Pro Val His Cys Ile Lys Thr Thr
210                 215                 220
```

(2) INFORMATION FOR SEQ ID NO:10:

(i) SEQUENCE CHARACTERISTICS:
        (A) LENGTH: 226 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:10:

```
Val Glu Asn Glu Leu Pro Pro Glu Asn Ile Glu Val Ser Val Gln
1               5                   10                  15

Asn Gln Asn Tyr Val Leu Lys Trp Asp Tyr Thr Tyr Ala Asn Met Thr
            20                  25                  30

Phe Gln Val Gln Trp Leu His Ala Phe Leu Lys Arg Asn Pro Gly Asn
        35                  40                  45

His Leu Tyr Lys Trp Lys Gln Ile Pro Asp Cys Glu Asn Val Lys Thr
    50                  55                  60

Thr Gln Cys Val Phe Pro Gln Asn Val Phe Gln Lys Gly Ile Tyr Leu
65                  70                  75                  80

Leu Arg Val Gln Ala Ser Asp Gly Asn Asn Thr Ser Phe Trp Ser Glu
                85                  90                  95

Glu Ile Lys Phe Asp Thr Glu Ile Gln Ala Phe Leu Leu Pro Pro Val
                100                 105                 110

Phe Asn Ile Arg Ser Leu Ser Asp Ser Phe His Ile Tyr Ile Gly Ala
            115                 120                 125

Pro Lys Gln Ser Gly Asn Thr Pro Val Ile Gln Asp Tyr Pro Leu Ile
        130                 135                 140

Tyr Glu Ile Ile Phe Trp Glu Asn Thr Ser Asn Ala Glu Arg Lys Ile
145                 150                 155                 160

Ile Glu Lys Lys Thr Asp Val Thr Val Pro Asn Leu Lys Pro Leu Thr
                165                 170                 175

Val Tyr Cys Val Lys Ala Arg Ala His Thr Met Asp Glu Lys Leu Asn
                180                 185                 190

Lys Ser Ser Val Phe Ser Asp Ala Val Cys Glu Lys Thr Lys Pro Gly
            195                 200                 205

Asn Thr Ser Lys Ile Trp Leu Ile Val Gly Ile Cys Ile Ala Leu Phe
    210                 215                 220

Ala Leu
225

(2) INFORMATION FOR SEQ ID NO:11:

(i) SEQUENCE CHARACTERISTICS:
        (A) LENGTH: 224 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:11:

Met Leu Ala Val Val Gly Ala Ala Ala Leu Val Leu Val Ala Gly Ala
1               5                   10                  15

Pro Trp Val Leu Pro Ser Ala Ala Gly Gly Glu Asn Leu Lys Pro Pro
            20                  25                  30

Glu Asn Ile Asp Val Tyr Ile Ile Asp Asp Asn Tyr Thr Leu Lys Trp
        35                  40                  45

Ser Ser His Gly Glu Ser Met Gly Ser Val Thr Phe Ser Ala Glu Tyr
    50                  55                  60

Arg Thr Lys Asp Glu Ala Lys Trp Leu Lys Val Pro Glu Cys Gln His
65                  70                  75                  80
```

-continued

```
Thr Thr Thr Thr Lys Cys Glu Phe Ser Leu Leu Asp Thr Asn Val Tyr
              85                  90                  95

Ile Lys Thr Gln Phe Arg Val Arg Ala Glu Glu Gly Asn Ser Thr Ser
             100                 105                 110

Ser Trp Asn Glu Val Asp Pro Phe Ile Pro Phe Tyr Thr Ala His Met
             115                 120                 125

Ser Pro Pro Glu Val Arg Leu Glu Ala Glu Asp Lys Ala Ile Leu Val
    130                 135                 140

His Ile Ser Pro Pro Gly Gln Asp Gly Asn Met Trp Ala Leu Glu Lys
145                 150                 155                 160

Pro Ser Phe Ser Tyr Thr Ile Arg Ile Trp Gln Lys Ser Ser Ser Asp
                165                 170                 175

Lys Lys Thr Ile Asn Ser Thr Tyr Tyr Val Glu Lys Ile Pro Glu Leu
                180                 185                 190

Leu Pro Glu Thr Thr Tyr Cys Leu Glu Val Lys Ala Ile His Pro Ser
        195                 200                 205

Leu Lys Lys His Ser Asn Tyr Ser Thr Val Gln Cys Ile Ser Thr Thr
210                 215                 220
```

(2) INFORMATION FOR SEQ ID NO:12:

(i) SEQUENCE CHARACTERISTICS:
        (A) LENGTH: 219 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:12:

```
Val Ala Asn Lys Met Pro Val Pro Gly Asn Leu Gln Val Asp Ala Gln
1               5                  10                  15

Gly Lys Ser Tyr Val Leu Lys Trp Asp Tyr Ile Ala Ser Ala Asp Val
             20                  25                  30

Leu Phe Arg Ala Gln Trp Leu Pro Gly Tyr Ser Lys Ser Ser Ser Gly
         35                  40                  45

Ser His Ser Asp Lys Trp Lys Pro Ile Pro Thr Cys Ala Asn Val Gln
    50                  55                  60

Thr Thr His Cys Val Phe Ser Gln Asp Thr Val Tyr Thr Gly Thr Phe
65                  70                  75                  80

Phe Leu His Val Gln Ala Ser Glu Gly Asn His Thr Ser Phe Trp Ser
                 85                  90                  95

Glu Glu Lys Phe Ile Asp Ser Gln Lys His Ile Leu Pro Pro Pro Pro
             100                 105                 110

Val Ile Thr Val Thr Ala Met Ser Asp Thr Leu Leu Val Tyr Val Asn
             115                 120                 125

Cys Gln Asp Ser Thr Cys Asp Gly Leu Asn Tyr Glu Ile Ile Phe Trp
    130                 135                 140

Glu Asn Thr Ser Asn Thr Lys Ile Ser Met Glu Lys Asp Gly Pro Glu
145                 150                 155                 160

Phe Thr Leu Lys Asn Leu Gln Pro Leu Thr Val Tyr Cys Val Gln Ala
                165                 170                 175

Arg Val Leu Phe Arg Ala Leu Leu Asn Lys Thr Ser Asn Phe Ser Glu
                180                 185                 190
```

```
Lys Leu Cys Glu Lys Thr Arg Pro Gly Ser Phe Ser Thr Ile Trp Ile
    195                 200                 205

Ile Thr Gly Leu Gly Val Val Phe Phe Ser Val
    210                 215
```

(2) INFORMATION FOR SEQ ID NO:13:

(i) SEQUENCE CHARACTERISTICS:
        (A) LENGTH: 224 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:13:

```
Met Leu Ala Leu Leu Gly Ala Thr Thr Leu Met Leu Val Ala Gly Arg
1               5                   10                  15

Trp Val Leu Pro Ala Ala Ser Gly Glu Ala Asn Leu Lys Pro Glu Asn
                20                  25                  30

Val Glu Ile His Ile Ile Asp Asp Asn Phe Phe Leu Lys Trp Asn Ser
            35                  40                  45

Ser Ser Glu Ser Val Lys Asn Val Thr Phe Ser Ala Asp Tyr Gln Ile
50                  55                  60

Leu Gly Thr Asp Asn Trp Lys Lys Leu Ser Gly Cys Gln His Ile Thr
65                  70                  75                  80

Ser Thr Lys Cys Asn Phe Ser Ser Val Glu Leu Glu Asn Val Phe Glu
                85                  90                  95

Lys Ile Glu Leu Arg Ile Arg Ala Glu Glu Gly Asn Asn Thr Ser Thr
            100                 105                 110

Trp Tyr Glu Val Glu Pro Phe Val Pro Phe Leu Glu Ala Gln Ile Gly
        115                 120                 125

Pro Pro Asp Val His Leu Glu Ala Glu Asp Lys Ala Ile Ile Leu Ser
130                 135                 140

Ile Ser Pro Pro Gly Thr Lys Asp Ser Ile Met Trp Ala Met Asp Arg
145                 150                 155                 160

Ser Ser Phe Arg Tyr Ser Val Val Ile Trp Lys Asn Ser Ser Ser Leu
                165                 170                 175

Glu Glu Arg Thr Glu Thr Val Tyr Pro Glu Asp Lys Ile Tyr Lys Leu
            180                 185                 190

Ser Pro Glu Ile Thr Tyr Cys Leu Lys Val Lys Ala Glu Leu Arg Leu
        195                 200                 205

Gln Ser Arg Val Gly Cys Tyr Ser Pro Val Tyr Cys Ile Asn Thr Thr
210                 215                 220
```

(2) INFORMATION FOR SEQ ID NO:14:

(i) SEQUENCE CHARACTERISTICS:
        (A) LENGTH: 227 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:14:

```
Glu Arg His Lys Val Pro Ser Pro Glu Asn Ile Gln Ile Asn Ala Asp
1               5                   10                  15

Asn Gln Ile Tyr Val Leu Lys Trp Asp Tyr Pro Tyr Glu Asn Ala Thr
            20                  25                  30

Phe Gln Ala Gln Trp Leu Arg Ala Phe Phe Lys Lys Ile Pro Gly Asn
        35                  40                  45

His Ser Asp Lys Trp Lys Gln Ile Pro Asn Cys Glu Asn Val Thr Ser
    50                  55                  60

Thr His Cys Val Phe Pro Arg Glu Val Ser Ser Arg Gly Ile Tyr Tyr
65                  70                  75                  80

Val Arg Val Arg Ala Ser Asn Gly Asn Gly Thr Ser Phe Trp Ser Glu
                85                  90                  95

Glu Lys Glu Phe Asn Thr Glu Met Lys Thr Ile Ile Phe Pro Pro Val
            100                 105                 110

Ile Ser Val Lys Ser Val Thr Asp Asp Ser Leu His Val Ser Val Gly
        115                 120                 125

Ala Ser Glu Glu Ser Glu Asn Met Ser Val Asn Gln Leu Tyr Pro Leu
130                 135                 140

Ile Tyr Glu Val Ile Phe Trp Glu Asn Thr Ser Asn Ala Glu Arg Lys
145                 150                 155                 160

Val Leu Glu Lys Arg Thr Asn Phe Ile Phe Pro Asp Leu Lys Pro Leu
                165                 170                 175

Thr Val Tyr Cys Val Lys Ala Arg Ala Leu Ile Glu Asn Asp Arg Arg
            180                 185                 190

Asn Lys Gly Ser Ser Val Ser Asp Thr Val Cys Glu Lys Thr Lys Pro
        195                 200                 205

Gly Asn Thr Ser Lys Thr Trp Leu Ile Val Gly Thr Cys Thr Ala Leu
    210                 215                 220

Phe Ser Ile
225
```

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:15:

GCTCGAAGGC GTAGAGTGAC                          20

(2) INFORMATION FOR SEQ ID NO:16:

(i) SEQUENCE CHARACTERISTICS:
        (A) LENGTH: 6 base pairs
        (B) TYPE: nucleic acid
        (C) STRANDEDNESS: unknown
        (D) TOPOLOGY: unknown (ii) MOLECULE TYPE: DNA (genomic)

-continued (iii) HYPOTHETICAL: NO (iv) ANTI-SENSE: NO (xi) SEQUENCE DESCRIPTION: SEQ ID NO:16:

AATAAA                                                                  6

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:17:

Tyr Asp Lys Pro His
1               5

ACCESSORY FACTORY FUNCTION FOR INTERFERON GAMMA AND ITS RECEPTOR

This is a continuation application of copending patent appplication Ser. No. 08/444,134, filed May 18, 1995, which is a divisional of parent application Ser. No. 08/110,119, filed Aug. 20, 1993.

FIELD OF THE INVENTION

This invention relates (a) to a 540 kb YAC which encodes the necessary species-specific factor(s) and is able to substitute for human Chromosome 21 to reconstitute the Hu-IFN-gamma receptor-mediated induction of class I HLA antigens; (b) to the construction of a plasmid to integrate the selective marker for antibiotic G418 resistance into YACs and to delete some of the human DNA fragments from YACs in order to facilitate the manipulation of human genomic DNA in yeast artificial chromosome (YAC) clones; (c) to two fragmentation vectors, pSE1 and pSE2, which contain a neomycin resistance and URA3 gene, developed for targeting yeast artificial chromosomes (YACs) containing human genomic DNA; (d) to a chromosomal fragmentation procedure employed to produce a deletion set of yeast artificial chromosomes (YACs) from a parental YAC (GART D142H8) known to map to Chromosome 21q and to encode the human interferon-gamma receptor (Hu-IFN-gamma R) accessory factor gene as well as the phosphoribosylglycinamide formyltranisferase (GART) gene; and (e) to the isolation of cDNA clones that encode the necessary species-specific factor and that are able to substitute for human Chromosome 21 to reconstitute the Hu-IFN-gamma receptor-mediated induction of class I HLA antigens.

BACKGROUND OF THE INVENTION

The disclosures referred to herein to illustrate the background of the invention and to provide additional detail with respect to its practice are incorporated herein by reference and, for convenience, are numerically referenced in the following text and respectively grouped in the appended bibliography.

YAC Clone Encoding an Accessory Factor

Human interferon gamma (Hu-IFN-gamma) induces a variety of biological responses such as antiviral, antiproliferative, and immunomodulatory activities in sensitive cells (1–5). Immunoregulatory functions induced by Hu-IFN-gamma such as induction of class I and class II human HLA antigens, activation of macrophages, regulation of Ig class switching, and up-regulation of Fc receptor expression are involved in modulating a variety of other host defense mechanisms (5–10). The first event in inducing these responses is the specific binding of IFN-gamma to its cell surface receptor encoded on human Chromosome 6 (11) or mouse Chromosome 10 (12,64). However, human Chromosomes 6 and 21 (14,15) and mouse Chromosomes 10 and 16 (16) are required for sensitivity to IFN-gamma as measured by the induction of class I MHC antigens, which indicates that the binding of IFN-gamma to the receptor is necessary, but not sufficient to induce these antigens. Interaction between the extracellular domain of the Hu-IFN-gamma receptor and the species-specific accessory factor (AF-1) which leads to class I HLA antigen induction upon treatment with Hu-IFN-gamma was suggested by experiments with chimeric receptors (17-19). A five-amino acid sequence (YDKPH) SEQ ID NO. 17 of the intracellular domain of the Hu-IFN-gamma receptor is required for this activity (20,21). Moreover, at least two additional accessory factors (AF-2 and AF-3) are involved in EMCV and VSV antiviral activity (20,65). However, little is known about how the binding of Hu-IFN-gamma to its receptor initiates this diverse array of functional changes and the nature of the accessory factors.

The region of Chromosome 21 which is necessary for sensitivity to Hu-IFN-gamma as assayed by the expression of class I HLA antigens was localized within a region of about 1–3 mb of Chromosome 21q with irradiation-reduced hamster/human somatic hybrid cells (22). The cloned Hu-IFN-gamma receptor cDNA (23,24) was expressed in hamster/human hybrid cells which have human Chromosome 21q as the sole human Chromosome to reconstitute a biologically-active Hu-IFN-gamma receptor for HLA class I antigen induction (25), and EMCV antiviral protection activity (20). Thus, it appeared that human Chromosome 21q encodes all necessary factors for both activities. This was confirmed by another study with mouse/human hybrid cells transfected with the Hu-IFN-gamma receptor cDNA that showed that human Chromosome 21 is sufficient for induction of class I MHC antigens, EMCV antiviral activity and induction of 2',5'-oligoadenylate synthetase in response to Hu-IFN-gamma (26).

The cloning of DNA into yeast artificial chromosomes (YACs) has allowed isolation of much larger DNA fragments than was previously possible (27). Also, development of polymerase chain reaction (PCR)-based YAC screening methods has facilitated the identification of specific YAC clones (28). These large cloned segments have potential applications for the isolation of functional domains from chromosomes (29). To assay for the biological functions of genes included in YACs, yeast cells can be fused to cultured mammalian cells. Experiments to demonstrate the functional expression of genes carried on YACs have been carried out with G6PD (glucose-6-phosphate dehydrogenase), HPRT (hypoxanthine phosphoribosyltransferase) and GART YAC clones (30–32). To allow selection for fused cells in these cases, a gene cassette that confers resistance to antibiotic G418 on mammalian cells can be introduced into the YAC by homologous recombination targeted to human genomic sequences (33,34).

Alu-targeting YAC Deletion Plasmids

Yeast artificial chromosomes (YACs) provide a system for the cloning of up to one megabase of contiguous DNA (55,56). While the large size of the YAC insert facilitates the isolation of specific large segments of DNA (59), identification and localization of genes within the YAC requires conventional yeast genetic techniques to manipulate the YAC insert (39).

Chromosome fragmentation has been developed for *Saccharomyces cerevisiae* YPH252 with a fragmentation plasmid (48,60). Fragmentation takes advantage of homologous recombination between Alu family sequences or LINE human repetitive DNA elements in the fragmentation plasmid and the YAC insert. The recombination event causes chromosome breakage at the site where homologous integration occurs and deletion of all portions of the YAC distal to the targeted site. Similarly another fragmentation plasid system has been developed for *S. cerevisiae* AB1380 (58). The plasmid developed by Cook et al. contained the gene for neomycin phosphotransferase as a eukaryotic selectable marker. A second type of YAC modification plasmid, an integrating plasmid, has been described (33) for *S. cerevisiae* YPH252. In contrast to the fragmentation plasmid, the integrating plasmid contains two recombinogenic sequences resulting in the insertion of the plasmid into the YAC. The integrating plasmid has been used mainly to insert a neomycin-resistance cassette to be used as a selectable marker following fusion of YAC-containing yeast spheroplasts with mammalian cells (33). Another integrating plasmid containing a DNA fragment derived from the DNA of the YAC insert, not Alu family sequences, has been described (34).

Yeast Artificial Chromosome Fragmentation Vectors

Yeast artificial chromosome vectors have enabled the cloning of up to 1 megabase of DNA (27). In order to reduce YACs to smaller sizes for mapping and manipulation, Reeves et al. (62) and Pavan et al. (48) have developed fragmentation vectors which are capable of producing a set of deletions in a parental YAC containing human genomic DNA. The fragmented YACs obtained by this procedure are useful not only for mapping studies but also for determining the location of genes encoding certain biochemical functions. The vectors which have been reported utilize transformation to a His$^+$ phenotype to select for clones containing fragmented YACs (48,60). While this procedure is applicable to YACs carried in his3$^-$ YPH252 yeast cells, it cannot be used with the AB1380 yeast strain which is the host for many YAC libraries.

Localization of the Human Interferon-gamma Receptor Accessory Factor Gene

The human and murine interferon gamma receptors (IFN-gamma R) have been shown to be homologous to a considerable degree (94). Nevertheless, these receptors are very specific in terms of binding human and murine IFN-gamma, respectively (95). A second level of species specificity involves the IFN-gamma accessory factor. The existence of the IFN-gamma accessory factor was first postulated because experiments with somatic cells hybrids indicated that the chromosome encoding the gene for the human IFN-gamma R (Chromosome 6) is itself not sufficient for biological activity even though human IFN-gamma can bind to the receptor (96–98). Only when human Chromosome 6 is complemented with human Chromosome 21 in somatic cell hamster×human hybrids does Hu-IFN-gamma signal transduction occur (97,98). Similarly, only when murine Chromosome 10 encoding the Mu-IFN-gamma R (99) is accompanied by murine Chromosome 16 (encoding the murine accessory factor) does the Mu-IFN-gamma R become biologically active in hamster×murine somatic cell hybrids (100).

The human Chromosome 21 accessory factor is likely to be a membrane-associated protein as several studies have shown that the accessory factor and the extracellular domain of the IFN-gamma R must be from the same species for signal transduction to occur (101–103). Although interactions with the transmembrane and intracellular domains have not been ruled out, these interactions, if they exist, are not species specific. Use of radiation-reduced somatic cell hybrids has enabled further mapping of the accessory factor gene on Chromosome 21 (104). To date, the most accurate estimate of the chromosomal location of the accessory factor gene as determined in somatic cell hybrids indicates that the gene is located proximal to marker D21S58 (104). More recent data from this laboratory indicate that accessory factor activity is encoded by the yeast artificial chromosome (YAC) whose address on chromosome 21 is D142H8 (105). This YAC, designated GART D142H8 because it also encodes the GART gene, is 540 kb in length and is located proximal to the YAC which encodes the human IFN-α/β receptor (105).

Throughout the specification and claims, the following abbreviations will stand for the words and phrases set out below.

A, Ala; C, Cys; D, Asp; E, Glu; F, Phe, G, Gly; H, His; I, Ile; K, Lys; L, Leu; M, Met; N, Asn; P, Pro; Q, Gln; R, Arg; S, Ser; T, Thr; V, Val; W, Trp; Y, Tyr.

2,5-A$_n$: (2'-5')-oligoadenylate: (2'-5')-oligo(adenylic) acid; oligoadenylic acid with 2',5'-phosphodiester linkages: also abbreviated as (2'-5')-oligio(A), pppA(2'p5' A)n, pppA(2'-5')An, or (2'-5')p$_3$A$_3$; 2–5A is used as well as 2,5-p$_3$A$_n$.

A$_{260}$ unit: The quantity of material that yields an absorbance of 1.0 when measured at 260 nm in a cuvette with a path length of 1.0 cm. Analogously, A$_{600}$ represents measurements at 600 nm, A$_{550}$ at 550 nm, etc. This quantity of material is also sometimes designated as OD$_{260}$, OD$_{550}$, OD$_{600}$, etc.

Act D: Actinomycin D

BES: N,N-bis[2-Hydroxyl]-2-aminoethanesulfonic acid; 2-[bis(2-hydroxyethyl)amino]-ethanesulfonic acid BP: Base pairs; usually used as lower case bp.

Bq: Becquerel; 1 Bq=1 dps or 60dpm; 1 Ci=3.7×10$^{10}$ Bg; TBq=10$^{12}$ Bq

BSA: Bovine serum albumin

Con A: Concanavalin A

CPD: Citrate phosphate dextrose solution

CPE: Cytopathic effect ;

DEAE Cellulose: Diethylaminoethylcellulose

DHFR: Dihydrofolate reductase

DNA: Deoxyribonucleic acid

CDNA: Complementary DNA dsDNA: Double-stranded DNA

DRB: 5,6-Dichloro-1-beta-D-ribofuranosylbenzimidazole dsRNA: Double-stranded RNA DTT: Dithiothreitol EDTA: Ethylenediaminetetraacetic acid EGTA: Ethylene glycol bis(beta-aminoethyl ether)-N,N'-tetraacetic acid EID$_{50}$: Egg infectious dose; concentration at which half the eggs are infected.

EMCV: Encephalomyocarditis virus

EMEM: Eagle's minimal essential medium

ESS: Earle's salt solution

FBS: Fetal bovine serum

FCS: Fetal calf serum

GPT: Guanosine phosphoribosyltransferase (recommended name is guanosine phosphorylase; systematic name is guanosine: orthophosphate ribosyltransferase HBSS: Hanks' balanced salt solution HEPES: N-2-Hydroxethylpiperazine-N'-2-ethanesulfonic acid IU: Units of interferon with respect to the appropriate international reference standard.

KBP: Kilobase pairs; usually used as lower case kbp.

MDMP: 2-(4-Methyl-2,6-dinitroanilino)-N-methyl-propionamide

MEM: Minimal essential medium (EMEM, unless otherwise noted).

Mg(OAc)$_2$: Magnesium acetate

MOI: Multiplicity of infection

NAD: Nicotinamide adenine dinucleotide

NaOAc: Sodium acetate

Natural interferon: This term refers to interferon produced by animal cells after induction in contrast to interferon produced by recombinant DNA technology. In some cases the two (i.e., the interferon produced by animal cells and the same species by recombinant DNA technology) may be chemically identical.

NDV: Newcastle disease virus

PBL: Peripheral blood leukocytes

PBMC: Peripheral blood mononuclear cells

PBS: Phosphate-buffered saline

PFC: Plaque-forming cell

PFU: Plaque-forming unit

PHA: Phytohemagglutinin

Poly(I).poly(C): Polyinosinic acid.polycytidylic acid double stranded synthetic homopolymers [alternatively poly(rI).poly(rC)]

RNA: Ribonucleic acid dsRNA: double-stranded RNA

SDS: Sodium dodecyl sulfate

SDS-Page: SDS-Polyacrylamide gel electrophoresis

SEA: Staphylococcal enterotoxin A

SEB: Staphylococcal enterotoxin B

SSC: Standard saline citrate solution, 0.15 M NaCl/0.015 M sodium citrate, adjusted to pH 7.0 with NaOH.

TCA: Trichloroacetic acid

TCID$_{50}$: Tissue culture infectious dose; concentration at which half the cultures are infected.

TEMED: N,N,N',N'-Tetramethylethylenediamine

TES: N-Tris(hydroxymethyl)methyl-2-aminoethanesulfonic acid

Tricine: N-Tris(hydroxymethyl)methylglycine

TPA: The phorbol ester 12-O-tetradecanoylphorbol-13-acetate.

Tris: Tris(hydroxymethyl)aminomethane

VSV: Vesicular stomatitis virus

Other Abbreviations: YAC, yeast artificial chromosome; PFGE, pulsed-field gel electrophoresis; Hu-IFN-gamma, human interferon gamma; HLA, human leucocyte antigen; CHO, Chinese hamster ovary; GART, phosphoribosylglycinamide formyltransferase; EMCV, encephalomyocarditis virus; VSV, vesicular stomatitis virus.

BRIEF DESCRIPTION OF THE FIGURES

FIG. 1 shows a pulse field gel electrophoresis of various YACs and hybridization to total human DNA.

FIG. 2A illustrates the agarose plugs from neo$^r$ Lys2+ transformants derived from each YAC clone were analyzed by PFGE and the blot was probed with the labelled neo$^r$ gene to determine whether or not the neo$^r$ gene was targeted to the YAC. FIG. 2B shows that yeast chromosomal DNAs from the same YAC clones as in A were digested with BamHI and XhoI to release the neo$^r$ gene cassette and the blot was probed with the labelled neo$^r$ gene.

FIGS. 7 illustrates the localization of integrated plasmid in targeted YAC. FIG. 7A illustrates a quarter of a plug incubated with restriction endonuclease NotI followed by pulsed-field gel electrophoresis. FIG 7B is a schematic diagram showing where the integrated plasmid is located in terms of the two NotI sites.

FIGS. 9 illustrates an agarose gel electrophoresis of DNA and Southern blot analysis. FIG. 9A shows yeast chromosomal DNAs from random internally-deleted YAC clones cut with restriction endonuclease EcoRI, run on a 0.8% agarose gel, and blotted onto a nylon membrane. FIG. 9B shows the blot reprobed with the acentric vector arm.

FIG. 13 is a schemiatic illustration of YACs used to transform 16-9 cells.

FIG. 16 is a gel shift assay for ISGF3-gamma(A) and GAF(B) in selected cell lines.

FIG. 19A shows three micrograms of oligo(dT)-selected mRNA from 3x1S cells fractionated on a 1.0% agarose gel containing 2.2 M formaldehyde and blotted onto a nylon membrane. FIG. 19B shows about one half microgram of oligo(dT)-selected mRNA from Raji and HL60 cells processed and probed with a 1.8 kb insert from plasmid pJS3.

FIG. 21 illustrates human IFN-gamma accessory factor-1 (AF-1) cDNA (plasmid pSK1 and plasmid pJS3) nucleotide and predicted amino acid sequences.

FIG. 23A and FIG. 23B represent 16-9 cells. FIG. 23C and FIG. 23D represent pools of 16-9 cells transfected with plasmid pJS3.

FIG. 24 shows the amino acid sequence alignment of human AF-1 and some members of the class 2 cytokine receptor family.

SUMMARY OF THE INVENTION

This invention relates (a) to a 540 kb YAC which encodes the necessary species-specific factor(s) and is able to substitute for human Chromosome 21 to reconstitute the Hu-IFN-gamma receptor-mediated induction of class I HLA antigens; (b) to the construction of a plasmid to integrate the selective marker for antibiotic G418 resistance into YACs and to delete some of the human DNA fragments from YACs in order to facilitate the manipulation of human genomic DNA in yeast artificial chromosome (YAC) clones; (c) to two fragmentation vectors, pSE1 and pSE2, which contain a neomycin resistance and URA3 gene, developed for targeting yeast artificial chromosomes (YACs) containing human genomic DNA; (d) to a chromosomal fragmentation procedure employed to produce a deletion set of yeast artificial chromosomes (YACs) from a parental YAC (GART D142H8) known to map to Chromosome 21q and to encode the human interferon-gamma receptor (Hu-IFN-gamma R) accessory factor gene as well as the phosphoribosylglycinamide formyltransferase (GART) gene; and (e) to the isolation of cDNA clones that encode the necessary species-specific factor and that are able to substitute for human Chromosome 21 to reconstitute the Hu-IFN-gamma receptor-mediated induction of class I HLA antigens.

DETAILED DESCRIPTION OF THE INVENTION

YAC Clone Encoding an Accessory Factor

Human Chromosomes 6 and 21 are both necessary to confer sensitivity to human interferon gamma (Hu-IFN-gamma) as measured by the induction of human HLA class I antigen. Whereas human Chromosome 6 encodes the receptor for Hu-IFN-gamma, human Chromosome 21 encodes accessory factors for generating biological activity through the Hu-IFN-gamma receptor. A small region of human Chromosome 21 which is responsible for encoding such factors was localized with hamster-human somatic cell hybrids carrying an irradiation-reduced fragment of human Chromosome 21. The cell line with the minimum Chromosome 21-specific DNA is CHO 3x1S. In order to localize the genes further, 10 different YAC (yeast artificial chromosome) clones from 6 different loci in the vicinity of the 3x1S region were fused to a human×hamster hybrid cell line (designated 16-9) which contains human Chromosome 6q (supplying the Hu-IFN-gamma receptor) and the human HLA-B7 gene. These transformed 16-9 cells were assayed for induction of class I HLA antigens upon treatment with Hu-IFN-gamma. It was found that a 540 kb YAC encodes the necessary species-specific factor(s) and is able to substitute for human Chromosome 21 to reconstitute the Hu-IFN-gamma receptor-mediated induction of class I HLA antigens. However, the factor encoded on the YAC does not confer antiviral protection against encephalomyocarditis virus demonstrating that an additional factor encoded on human Chromosome 21 is required for the antiviral activity.

Alu-targeting YAC Deletion Plasmids

Figure 4:
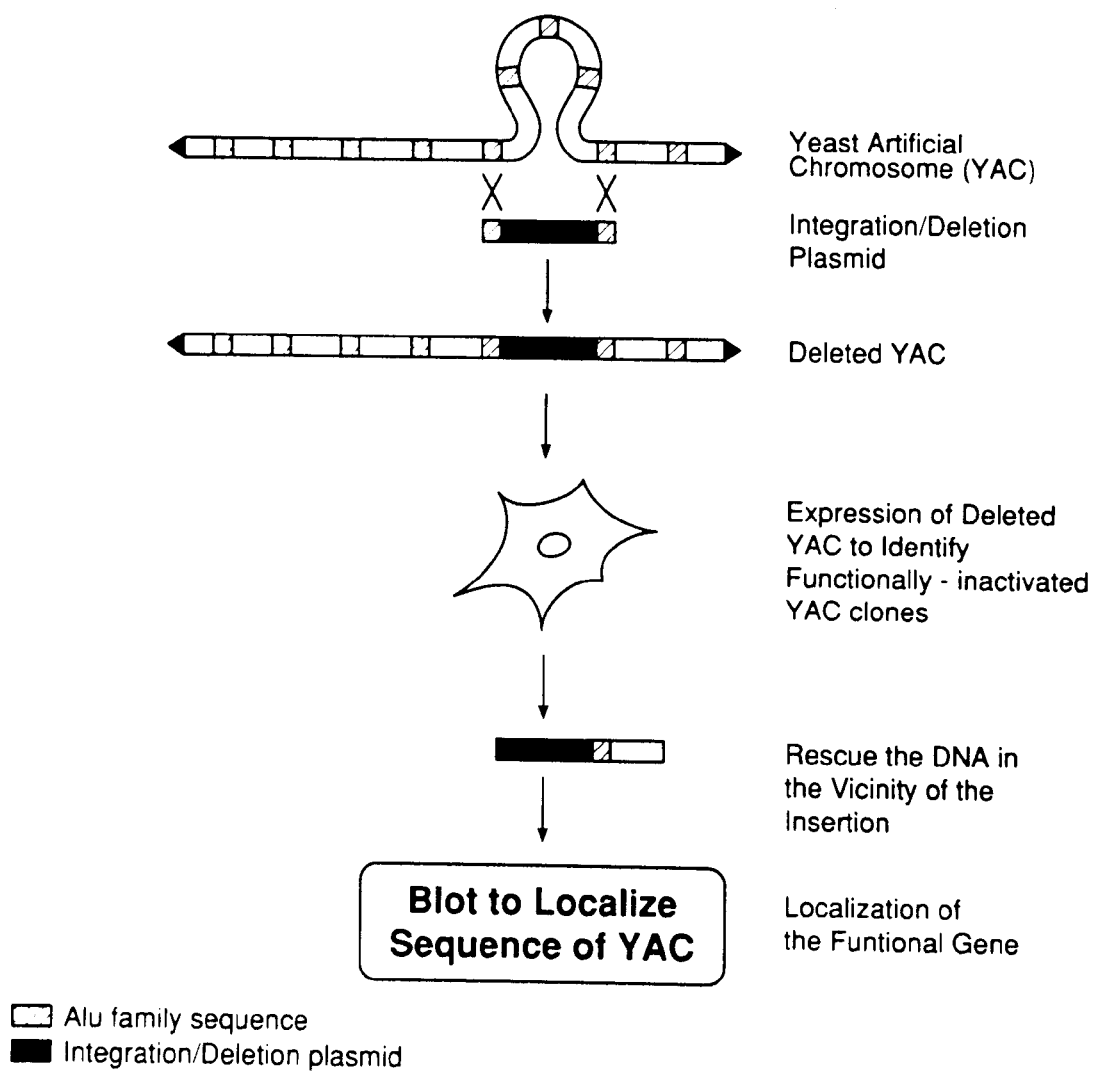
FIG. 4 illustrates the integration/deletion plasmid and its use. The schematic diagram shows two-point recombination between the integration/deletion plasmid and YAC insert that results in internal deletions.

In order to facilitate the manipulation of human genomic DNA in yeast artificial chromosome (YAC) clones, a plasmid to integrate the selective marker for antibiotic G418 resistance into YACs and to delete some of the human DNA fragments from YACs was constructed. The linearized integration/deletion plasmid, which contains Alu family sequences at both ends, can recombine with YACs containing human repetitive sequences via homologous recombination. The homologous recombination results in a random integration of the antibiotic G418 resistant gene into a human genomic Alu sequence, and in most cases, an internal deletion within the YAC. The YACs with internal deletions can be useful to identify the location of the genes if they produce functional knockouts. In those cases when the integration/deletion event disrupts the integrity of the gene so it no longer can produce a viable and functional mRNA in fused eukaryotic cells, the site of integration in the YAC thus serves as a marker for the inactivated gene. In this report we describe a new YAC integration/deletion plasmid for S. cerevisiae AB1380 to locate specific genes in YACs. This plasmid contains a human Alu family sequence (BLUR13) arranged in such a way that the plasmid integrates following two homologous recombination events within the YAC insert. These events result in the integration of the linearized plasmid at two Alu sequences resulting in the deletion of sequences between the sites of recombination (FIG. 4).

Yeast Artificial Chromosome Fragmentation Vectors

Two fragmentation vectors, pSE1 and pSE2, were developed for targeting yeast artificial chromosomes (YACs) containing human genomic DNA. Ura⁻ yeast cells containing YACs with a URA3 marker were selected with 5-fluoroorotic acid. Fragmented YACs were subsequently generated by transformation to a Ura⁺ phenotype. Over eighty percent of the transformants contained YACs of reduced molecular size. These fragmented YACs will prove to be useful in mapping the region of human chromosomes covered by the parental YAC. Fragmentation utilizing URA3 transformation provides a method for producing YAC deletion sets from YACs contained in AB1380 and other Ura3⁻ yeast stains. Linkage of a neomycin resistance gene to the URA3 gene facilitates functional analysis of these YACs in eukaryotic cells.

Localization of the Human Interferon-gamma Receptor Accessory Factor Gene

A chromosomal fragmentation procedure was employed to produce a deletion set of yeast artificial chromosomes (YACs) from a parental YAC (GART D142H8) known to map to Chromosome 21q and to encode the human interferon-gamma receptor (Hu-IFN-gamma R) accessory factor gene as well as the phosphoribosylglycinamide formyltransferase (GART) gene. Activity of the accessory factor gene in cell lines produced from the fusion of fragmented, neo⁺ YACs to CHO cells expressing the Hu-IFN-gamma R was used to localize the accessory factor gene. These deleted YACs retain accessory factor activity in Chinese hamster ovary cells until the deletions from the acentric end exceed 390 kb. Therefore, the accessory factor (AF-1) gene can be localized to a 150 kb region at the left (centric) end of the parental 540 kb GART YAC. Cell lines produced from the fusion of fragmented, neo+ YACs to CHO cells with the Hu-IFN-gamma R stably express this accessory factor. Cells containing functional YACs, as judged by MHC inducibility by IFN-gamma, are also able to induce the ISGF3-gamma and GAF transcription factors. However, cell lines containing the complete AF-1 gene were not protected against encephalomyocarditis virus (EMCV) by Hu-IFN-gamma although antiviral protection induced by IFN-gamma remained intact. Other CHO cell lines containing the Hu-IFN-gamma R and human Chromosome 21q have been shown to be protected against EMC, but not vesiculostomatitis virus (VSV) by Hu-IFN-gamma. Therefore, the Hu-IFN-gamma R and the accessory factor are sufficient for some, but not all, of the actions of the Hu-IFN-gamma. We postulate that an additional accessory factor required for antiviral activity is encoded on Chromosome 21q; and that at least two additional accessory factors are required for generation of antiviral activity against both EMCV and VSV.

cDNA Clone Encoding an Accessory Factor

The gene for one of the accessory factors was localized to a small genomic region (Soh et al., *Proc. Natl. Acad. Sci.*, in press) through the identification of functional YAC clones. With the use of probes isolated from the genomic clone, we identified cDNA clones expressing the accessory factor. Here we report isolation of cDNA clones that encode the necessary species-specific factor and that are able to substitute for human Chromosome 21 to reconstitute the Hu-IFN-gamma receptor-mediated induction of class I HLA antigens. However, the factor encoded by the cDNA does not confer antiviral protection against encephalomyocarditis virus confirming that an additional factor encoded on human Chromosome 21 is required for reconstitution of antiviral activity; and that a family of such accessory factors responsible for different actions of IFN-gamma exist.

As set out above, the present invention pertains to the Accessory Factor-1 (AF-1) for Human Interferon Gamma Function, each of the Variants of AF-1, and all other accessory factors or other factors isolated with the use of AF-1 constructs, transfected cells, etc., to isolate and define the factors. The present invention also pertains to antibodies to AF-1, such as monoclonal and polyclonal antibodies to AF-1. Antibodies to AF-1 may be employed (a) for the diagnosis of AF-1 deficiencies and excesses; (b) for tumor diagnosis (AF-1 in serum and urine); (c) for blocking of AF-1 specific mediated functions of IFN-gamma; and (d) for the treatment of diseases where soluble IFN-gamma receptors or IFN-gamma immunoadhesins are useful to block function of IFN-gamma. The present invention further pertains to soluble AF-1 which may be employed (a) for use a as standard in diagnosis as set out above; (b) for blocking the activity of the IFN-gamma receptor; and (c) for activating the AF-1 receptor with appropriate constructs of AF-1.

The present invention also pertains to (a) the use of AF-1 in gene therapy to reconstitute a defective IFN-gamma (systems defective in AF-1); (b) the use of oligonucleotides from the AF-1 sequence for diagnosis of AF-1 defects in tumors and other diseases; (c) the use of the nucleotide sequence (DNA, RNA) of AF-1 and its genes to use for diagnosis of tumors, other diseases, and defects in AF-1 function and expression; (d) the use of the AF-1 probes to isolate animal correlates of AF-1 so that animal AF-1 sequences will be covered (cat, bovine, dog, horse, mouse, rat, monkey, hamster, rabbit, goat, sheep, all mammals); (e) the nucleotide sequence of AF-1 and all closely related sequences that hybridize to the probes designed from the AF-1 sequence; (f) transgenic mice (animals) containing human AF-1 and the human IFN-gamma receptor of chimeric human/mouse IFN-gamma receptors to construct transgenic animals with a functional human IFN-gamma system (this will allow testing of the species specific IFN-gamma in mice for side effects and efficacy. At the present time, only species-specific cytokines as IFN-gamma can only be tested in humans. This can revolutionize the testing of such human cytokines in animal models); and (f) plasmids designed for Manipulation of YAC'S.

Use of AF-1 to Isolate Other Accessory Factors

The identification of AF-1 and the discovery of at least two other accessory factors provides a methodology for isolation of the other accessory factors and determining if there are more members of this family. The use of AF-1 together with other cosmids, YAC'S, or cDNA clones representing the 3x1S region of Chromosome 21 will permit a determination of whether AF-2 (the accessory factor required for EMCV protection by Hu-IFN-gamma) can function alone or requires AF-1. Furthermore, assay of other activities induced by IFN-gamma can be measured to define whether these are activities mediate through AF-1: these include antiproliferative activity, stimulation of T-cell functions, stimulation of macrophage (and similar cells) functions, other antiviral activities, stimulation of natural killer cells, etc.

AF-1 in Therapy of Cancer, Modulation of Class I Major Histocompatibility (MHC) Antigen Expression on Cells Because the IFN-gamma system is one of the most potent general growth regulators of cells and is also a powerful modulator of the immune system, there will be many uses for these accessory factors. These observations imply that the interferon system in general, and IFN-gamma specifically, is effective tumor suppression through two different avenues: direct action on tumor cells; and modulation of the immune system. Modifications in the level of AF-1 in tumor cells can be used as diagnostic criteria for cancer and prognosis; replacement of missing functions through gene therapy of tumor cells or other somatic cells such as lymphocytes and macrophages. Thus, the AF-1 gene can be used in the preparation of tumor vaccines and other approaches for the gene therapy of cancer. As a diagnostic criteria, AF-1 can be measured in the serum or other body fluids such as urine to determine the level of cell deterioration. IFN-gamma is one of the few cytokines active on virtually all cells in all tissues of the body; and the IFN-gamma receptor and AF-1 is present on virtually all cells as well. General breakdown of cells as occurs in malignancy and other diseases can be measured by studying AF-1 in serum, urine, and other fluids. Gene therapy of immune cells as well as the tumor cells will provide a two-pronged approach to tumor therapy of other diseases.

It is noted that little or no MHC class I antigen expression is often a characteristic of tumor cells that escape immune surveillance. The introduction of AF-1 into the immune and tumor cells can be used to reestablish normal function and elimination of malignant cells.

Antibodies to AF-1

Polyclonal and monoclonal antibodies to AF-1 will provide diagnostic tests to measure AF-1 in fluids and on cells. As noted above, this can be used to establish immunoassays (ELISA, RIA, fluorometric, chemoluminescent, etc.) to measure AF-1. These antibodies may be able to be used directly to inhibit excess IFN-gamma, IFN-gamma receptor and/or AF-1 function in diseases where activation of the IFN-gamma system is causative in the disease process. Diseases in which a hyperactive IFN-gamma system is likely to include Type I diabetes, multiple sclerosis, lupus erythematosus, adjuvant arthritis, Shwartzman reaction, delayed type hypersensitivity and allotransplant rejection [see Garotta, G., Ozmen, L., and Fountoulakis, M. (1989) "Development of Interferon-gamma Antagonists as an Example of Biotechnology Application to Approach New Immunomodulators," *Pharmacological Research* 21 Supplement 2, 5–17].

Soluble Forms of AF-1

Because antibodies can be used directly to block function of proteins, soluble forms of receptors and receptor components can be used to block receptor function and down regulate overactivity as in the diseases noted above. Soluble forms of receptors can be produced in prokaryotic or eukaryotic expression vectors, purified and used to down regulate over expression. If external contact with receptors is all that is required to generate a stimulation, then the soluble form of AF-1 can stimulate IFN-gamma function and serve as an activator directly without the necessity to enter the plasma membrane of the cell. Since the extracellular domain of the IFN-gamma receptor interacts with the extracellular domain of AF-1, the soluble forms may be able to carry out this activation directly. The soluble forms of AF-1 can be used to generate antibodies as could the intact complete molecules.

Generating a Complete Functional Cell-free Receptor

Soluble forms of the IFN-gamma receptor and other receptors have been shown to bind ligand with high affinity [see Fountoulakis, M., Juranville, J.-F., Stuber, D., Weibel, E. K., and Garotta, G. (1990) "Purification and Biochemical Characterization of a Soluble Human Interferon gamma Receptor Expressed in *Escherichia coli,*" *J. Biol. Chem.* 265, 13268–13275; Fountoulakis, M., Juranville, J.-F., Maris, A., Ozmen, L., and Garotta, G. (1990) "One Interferon gamma Receptor Binds One Interferon gamma Dimer," *J. Biol Chem.* 265, 19758–19767].However, it appears that the complete receptor requires AF-1 as well. Thus, an analysis of the structure activity relationships between receptor and ligand IFN-gamma will require AF-1 for refinement of the structural interfaces involved. This will lead to the development of small molecules that can activate the receptor and substitute for the large IFN-gamma protein ligand. Ideally, small molecules will be defined by molecular computer analysis of structure as well as crystallography to fill the interface and stimulate the receptors specifically. Furthermore, such molecules can be given orally in contract to parental injection that is now necessary of IFN-gamma. Small molecules can be designed to be agonists or antagonists of IFN-gamma function and thus can be used to mimic IFN-gamma or antagonize its actions for the syndromes noted above.

Plasmids Manipulating YAC Clones and Their Uses

The variety of plasmids we have developed to introduce markers into YACs, to delete regions of YACs and to fragment YACs provides new ways to manipulate YACs, introduce genes and locate genes within YACs. The plasmids have been designed for use with YAC containing human DNA insertions. Similar plasmids can be designed for manipulation of YACs from other animal species on the basis of the same principles.

Transgenic Mice Containing AF-1 and the IFN-gamma Receptor

Currently there is no way to test species specific human cytokines for true function in animal models. Efficacy and side-effects cannot be properly evaluated except in tedious and potentially hazardous human trials. The use of transgenic animals containing transgenes comprising the Hu-IFN-gamma receptor and AF-1 will provide the first step to generate mice that respond to human interferon just as we have shown than foreign cells expressing these components now respond to Hu-IFN-gammna. Because the other accessory factors are defined fully and isolated, the entire Hu-IFN-gamma system can be established in mice. Side effect and all actions of Hu-IFN-gamma will be able to be assessed in animal models that will increase the safety of the ultimate testing in humans of IFN-gamma. Furthermore, the principles developed permit a basis for establishing procedure to test other species-specific cytokines in animals.

Helper Function of Accessory Factors

The accessory factors serve to assist and enhance functions through the IFN-gamma receptor. AF-1 has specifically defined functions to overcome species specificity in conjunction with the corresponding receptor. Just like other helper proteins, such as B7, AF-1 and the other accessory factors support and enhance IFN-gamma receptor function. The IFN-gamma system has provided many insights into this complex system, but it will be paralleled by the IFN-$\alpha$ system as well. Thus, the IFN-$\alpha$ receptor complex will have multiple components that serve accessory functions for the IFN-$\alpha$ receptor.

The present invention is further illustrated by the following examples which are not intended to limit the effective scope of the claims. All parts and percentages in the examples and throughout the specification and claims are by weight of the final composition unless otherwise specified.

EXPERIMENTAL PROCEDURES

YAC Clone Encoding an Accessory Factor

Cells and Media

The 16-9 cell line is a Chinese hamster ovary (CHO-K1) hybrid containing a translocation of the long arm of human Chromosome 6 and a transfected human HLA-B7 gene (14,15; A. Rashidbaigi, unpublished results). The original parental line, 836-3A (11,14,15), was subcloned to obtain cells which expressed the human IFN-gamma receptor as demonstrated by binding and cross-linking to $^{32}$P-labeled Hu-IFN-gamma. These cells were then transfected with plasmid pJY105R1.1, a genomic clone encoding the human HLA-B7 antigen, obtained from S. Weissman (35,36). The cells were treated with 15,000 units/mL of Hu-IFN-$\alpha$A/D (Bgl), a human interferon active on hamster cells (37), for 2 days at 37° C. Then cells expressing the HLA-B7 antigen were isolated by treatment of cells with anti-HLA monoclonal antibody W6/32 (38) followed by incubation in a plate pre-coated with goat anti-mouse IgG ($F_c$-specific). Unbound cells were removed by washing and the bound cells were pooled and then subcloned as described (15,25). Subclones were analyzed for the presence of the long arm of human Chromosome 6 by binding and cross-linking with

[$^{32}$P]Hu-IFN-gamma and for HLA-B7 by a surface radioimmunoassay with the W6/32 monoclonal antibody (14,15, 25). Clone 16 was positive for human Chromosome 6 and HLA-B7 expression. Clone 16 was then subcloned and retested. Subclone 16-9 was shown to contain human Chromosome 6 and demonstrated the highest level of HLA-B7 induction in response to Hu-IFN-αA/D. These cells were unresponsive to treatment with Hu-IFN-gamma. The 153B7-8 cells are CHO-K1 cells carrying human Chromosome 21q and the human HLA B7 gene (14,15). The 3x1S cells are CHO-K1 cells that contain a small 1–3 kb region of human Chromosome 21 (22). These cells are maintained in F12 (Ham) medium (Sigma) containing 10% heat-inactivated bovine serum (Sigma), and 50 μg/ml gentamicin sulfate (complete F12 medium).

Ten YAC clones were obtained through the "Chromosome 21 Joint YAC Screening Effort" (directed by Dr. David Patterson, Eleanor Roosevelt Institute, Denver, Colo., USA). YAC clones were maintained and grown in AHC media. AHC medium contains 1.7 g of yeast nitrogen base without amino acids, 5 g of $(NH_4)_2SO_4$, 10 g of casein acid hydrolysate, 20 μg of adenine hemi-sulfate, and 20 g of glucose per liter. The addresses of the YAC clones used in this study are 525 B119G7, 525 A165D7, 525 C4C10, 525 C14B2, H8(517) A222A12, GART D142H8, 518 A234B10, 518 B134B9, SOD D112A5, and IFNAR B49F1. All YACs were derived from *Saccharomyces cerevisiae* AB1380 (MATa, ura3, trp1, ade2-1, can1-100, lys2-1 and his5) (27).

Construction of Integrating Plasmid

A 5.4 kb HindII restriction fragment containing the *Saccharomyces cerevisiae* LYS2 gene (a gift from Dr. Jules O'Rear, UMDNJ-Robert Wood Johnson Medical School) was inserted into the HindIII site of pMC1neo polyA (Stratagene, California) to yield the plasmid pMC-LYS2. A 0.3 kb Alu family repeat in plasmid pBP47 (33) (a gift from Dr. Roger H. Reeves, Johns Hopkins University School of Medicine, Baltimore, Md.) was modified by inserting a ClaI linker into the EcoRI site to form plasmid pBP47-ClaI. The modified Alu fragment was cut from plasmid pBP47-ClaI with BamHI, treated with mungbean nuclease, and ligated to the SalI site of pMC-LYS2 after filling-in with the Klenow fragment of DNA polymerase I, yielding plasmid pJS 1, the integrating plasmid.

Construction of YACs Containing the Antibiotic G418 Resistance Marker

Transformation was carried out as described (39) with the following modifications. Fifty milliliters of each YAC clone were grown to an absorption of 1.0 unit/mL at 600 nm in AHC liquid medium, harvested, and suspended in 5 mL of 1 M sorbitol. Fifty microliters of 10 mg/mL Zymolyase 20T (ICN) were added to the cell suspension, which was then incubated at 37° C. for 15–30 minutes to obtain greater than 95% conversion to spheroplasts. The spheroplasts were washed three times with 1 M sorbitol, collected by centrifugation (500×g, 5 minutes) and resuspended in STC medium (1 M sorbitol, 10 mM Tris/Cl pH 7.5, 10 mM $CaCl_2$) at a density of $5 \times 10^8$ spheroplasts/mL. Five micrograms of linearized plasmid pJS1 and 10 μg of salmon testes DNA as a carrier were put into 100 μL of the spheroplast suspension in a polypropylene tube, and the mixture incubated for 5 minutes at room temperature. After addition of 4 mL of polyethylene glycol (PEG) solution (20% w/v PEG 8000, 10 mM $CaCl_2$, 10 mM Tris/Cl, pH 7.5), the mixture was incubated for 10 minutes at room temperature, then centrifuged (500×g, 5 minutes) to pellet the spheroplasts. The mL of SOS medium (1 M sorbitol, 5 mM $CaCl_2$ in YPD medium consisting of 10 g of yeast extract, 20 g of peptone, and 20 g of glucose per liter), then incubated for 20 minutes at 30° C. with shaking. Finally, the spheroplasts were mixed with 6 mL of top agar and the mixture was overlaid on a synthetic dextrose minimal medium plate supplemented with adenine sulfate (10 μg/mL) and histidine (20 μg/mL) to select Lys$^+$ transformants.

Fusion

Each of the YAC clones containing the neo$^r$ gene was fused to 16-9 cells by a modification of a procedure already described (33). Thirty-five milliliters of each clone were grown in AHC media to stationary phase. After being washed twice with 20 mL of 1 M sorbitol, cells were resuspended in 5 mL of a solution which contained 1 M sorbitol, 100 mM sodium citrate (pH 5.8), 10 mM EDTA, and 30 mM β-mercaptoethanol. Eighty microliters of a Zymolyase 20T stock solution (10 mg/mL) were added, and the mixture was incubated at 37° C. for 20 minutes until 95% of the cells were spheroplasts. The spheroplasts were pelleted and washed twice in 5 mL of a solution of 1 M sorbitol in 10 mM Tris/Cl (pH 7.5), resuspended in 5 mL of the same solution, and counted. While the spheroplasts were being washed, the 16-9 cells were harvested by trypsinization, resuspended in serum free F-12 (Ham) medium (Sigma), and counted. Aliquots containing $4 \times 10^7$ spheroplasts were placed in 15-mL tubes and centrifuged at 500×g for 5 minutes. The supernatant was removed from the spheroplast pellet and 5 mL of the cell suspension containing $2 \times 10^6$ 16-9 cells was added carefully. The cells were then centrifuged at 500×μg for 5 minutes. The supernatant was removed and 50 μL of serum-free F12 medium was added to resuspend the pellets. Five hundred microliters of 45% PEG 1500 solution (Boehringer Mannheim Biochemicals) containing 5% DMSO, 10 μM β-mercaptoethanol, and 5 mM $CaCl_2$ were added to the mixed cell suspension. The cells were mixed by tapping the tube briefly, incubated for 2 minutes at room temperature, and diluted with 5 mL of serum-free F12 medium. This cell suspension was left at room temperature for 20 minutes, then centrifuged at 600×g for 6 minutes. The resulting pellet was resuspended in 5 mL of complete F12 medium and plated at $10^6$ 16-9 cells per 100 mm plate. Thirty-six hours later, plates were washed with phosphate-buffered saline (PBS) to remove dead cells and yeast, then referred with complete F12 medium containing 450 μg/mL of G418 (Gibco). Cells were fed as necessary, and resistant colonies typically appeared after 10 to 14 days. The G418-resistant colonies were pooled and expanded for further analysis.

Electrophoresis and Hybridization Procedures

Agarose plugs were prepared as described (40). Yeast cells were grown to stationary phase at 30° C. in 50 mL of AHC media, washed twice with 25 mL of 50 mM EDTA (pH 8.0) by centrifugation at 3500×g for 5 minutes, followed by resuspension at a density of $1 \times 10^{10}$ cells/ml in 50 mM EDTA. An equal volume of 1% (w/v) InCert agarose (FMC BioProducts) in 50 mM EDTA (pH 8.0) and 20 μL of 10 mg/mL Zymolyase 20T per milliliter of agarose solution were added to the cell suspension and the mixture was put into the plug mould. Spheroplasts were made by pushing plugs out of the mould into 1 mL of 0.5 M EDTA (pH 8.0) containing 7.5% β-mercaptoethanol per plug and incubating overnight at 37° C. with gentle shaking. The solution was removed and the plugs were rinsed twice with 50 mM EDTA (pH 9.25). The spheroplasts were lysed by transferring to Solution ESP [0.5 M of EDTA (pH 9.25), 1% Sarkosyl (IBI), and 1 mg/mL proteinase K (Sigma)] and incubating for 24 hr at 50° C. The agarose plugs were analyzed by pulsed-field gel electrophoresis (PFGE) (CHEF, OWL Scientific Plastics, Inc). The gels measured 13 cm×13 cm, consisted of 120 mL of 1% agarose in TBE (0.045 M Tris/borate, pH 8.0, 2.5 mM EDTA), and were run at 170 V for 24 hr at 15° C. with a pulse time of 70 seconds. The DNAs were blotted onto Nytran (Schleicher & Schuell) by standard Southern blot procedures (24,25). DNA probes were labeled with [$\alpha$-$^{32}$P] dCTP (NEN, 3000 Ci/mmol) with random hexadeoxynucleotides as primers (41).

Yeast Colony Hybridization

Colony hybridization of yeast cells was carried out as described (39). Briefly, the strains to be tested were streaked onto Nytran membrane filters on AHC plates. The plates were incubated for 2 days, and the filters were removed, air-dried and placed onto Whatman 3 MM paper sequentially saturated with the following solutions; Solution A (1 M sorbitol, 20 mM EDTA, 50 mM dithiothreitol) for 15 minutes, Solution B (1 M sorbitol, 20 2mM EDTA, 15 mg/mL Zymolyase 20T) for 2 hr at 37° C., Solution C (0.5 N NaOH) for 7 minutes, Solution D (0.5 M Tris.Cl, pH 7.5, 10×SSC) twice for 4 minutes each, and Solution E (2×SSC) for 2 minutes (1×SSC consists of 0.15 M NaCl and 0.015 M sodium citrate, adjusted to pH 7.0 with NaOH). The filter was baked and hybridized with the probe by standard procedures (24,25).

Cytofluorographic Analysis of Cells for Expression of the HLA-B7 Surface Antigen Cells were seeded in 24-well plates at a density of about 25,000 cells/well (0.5–1 mL/well) and were treated with 1,000 units/mL of the appropriate IFNs for about 72 hr by which time the cells were nearly confluent. These HLA assays were performed in the absence of antibiotic G418 as it was found the presence of this antibiotic inhibited MHC induction (T. M. Mariano, unpublished observation). Cells were trypsinized, transferred to 1.5 mL tubes, and washed with complete F12 medium. HLA-B7 antigen was detected by incubating the cells with 15 µL of culture supernatant containing a saturating concentration of mouse anti-HLA antibody, W6/32 (38), for 30 minutes at 4° C. Cells were washed with complete medium and resuspended in 15 µL of fluorescein isothiocyanate-conjugated (FITC-conjugated) sheep anti-mouse IgG diluted to 80 µg/mL and incubated for 30 minutes at 4° C., after which they were washed with complete medium and resuspended in 200 µL of cold complete medium for the immediate analysis of live cells. If cells had to be fixed for future analysis, they were washed once with PBS, resuspended in 15 µL of 3% (w/v) paraformaldehyde in PBS, and incubated 1 to 16 hrs at 4° C. The fixed cells were washed with PBS and finally resuspended in 200 µL PBS. Samples were analyzed on a Coulter Epics Profile Cytofluorograph with a 15-milliwatt Argon laser turned to 488 nm. Forward and 90° angle light scatter as well as integrated log green fluorescence signals (with a 488 nm long-pass laser blocking filter and 525 nm band-pass filter in place) were collected and analyzed. For each analysis, 10,000 events were accumulated and analyzed on the CytoLogic software as described (15,25).

Antiviral Assay

Transfected cells were assayed for resistance to encephalomyocarditis virus (EMCV) by a cytopathic effect inhibition assay (42).

Alu-targeting YAC Deletion Plasmids

Materials and Methods

Strains

GART YAC D142H8 was obtained from Dr. David Patterson (Eleanor Roosevelt Institute, Denver, Colo. USA, Chromosome 21 Joint YAC Screening Effort), and propagated in AHC medium. AHC medium contains 1.7 g of yeast nitrogen base without amino acids and ammonium sulfate, 5.0 g of $(NH_4)_2SO_4$, 10 g of casein acid hydrolysate, 20 µg of adenine hemi-sulfate and 20 g of glucose per liter. The human/hamster somatic cell hybrid line, 16-9, which contains human chromosome 6q and the human HLA B7 gene (14,57), was used for fusion with the YAC clones. The YAC clone is derived from *S. cerevisiae* AB1380 (MATa, ade2-1, can1-100, trp1, ura3, his5, [psi+]).

Construction of Integrating Plasmid

A 5.4 kb HindIII restriction fragment containing the *S. cerevisiae* LYS2 gene (a gift from Dr. Jules O'Rear, UMDNJ-Robert Wood Johnson Medical School) was inserted into the HindIII site of pMC1neo polyA (Stratagene, California) to yield the plasmid pMC-LYS2. A 0.3 kb BLUR13 Alu family repeat in plasmid pBP47 (33) (a gift from Dr. R. H. Reeves, Johns Hopkins University School of Medicine, Baltimore, Md.) was modified by inserting a ClaI linker into the EcoRI site to form plasmid pBP47-ClaI. The modified Alu fragment was cut from plasmid pBP47-ClaI with BamHI, treated with mungbean nuclease, and ligated to the SalI site of pMC-LYS2 after filling-in with the Kienow fragment of DNA polymerase I, yielding plasmid pJS1, the integration/deletion plasmid.

Transformation of YAC Clones with the Integration/Deletion Plasmid

Transformation was carried out as described (39) with the following modifications. Fifty milliliters of each YAC clone were grown to an absorption of 1.0 unit/ml at 600 nm in AHC liquid media, harvested, and suspended in 5 mL of 1 M sorbitol. Fifty microliters of 10 mg/ml Zymolyase 20T (ICN) were added to the cell suspension followed by a 15–30 minutes incubation at 37° C. to get more than 95% conversion to spheroplasts. The spheroplasts were washed three times with 1 M sorbitol, collected by centrifugation (500×g, 5 minutes) and resuspended in STC medium (1 M sorbitol, 10 mM Tris/Cl pH 7.5, 10 mM $CaCl_2$) at a density of 5×10$^8$ spheroplasts/mL. Five micrograms of ClaI-linearized plasmid pJS1 and 10 µg of salmon testes DNA as a carrier were put into 100 µL of the spheroplast suspension in a polypropylene tube, after which the mixture was incubated for 5 minutes at room temperature. Four milliliters of polyethylene glycol (PEG) solution (20% w/v PEG 8000, 10 mM $CaCl_2$, 10 mM Tris/Cl, pH 7.5) were added and the mixture was incubated for 10 minutes at room temperature, centrifuged (500×g, 5 minutes), resuspended in 300 mL of SOS medium (1 M sorbitol, 5 mM $CaCl_2$ in YPD medium consisting of 10 g of yeast extract, 20 g of peptone, and 20 g of glucose per liter), then incubated for 20 minutes at 30° C. with shaking. Finally, the spheroplasts were mixed with 6 mL of top agar and the mixture was overlaid on a plate of synthetic dextrose minimal medium supplemented with 10 µg/ml adenine sulfate and 20 µg/ml histidine to select Lys$^+$ transformants.

Fusion of Mammalian Cells with Yeast Spheroplasts

Each of the YAC clones containing the neo$^r$ gene was fused to 16-9 cells by a modification of a procedure already described (54,33,48). Twenty milliliters of each clone were grown in AHC media to stationary phase. Four milliliters of the culture was diluted four times into YPD medium and grown at 30° C. for one hour. After being washed twice with 10 mL of 1 M sorbitol, cells were resuspended in 3 mL of a solution which contains 1 M sorbitol, 100 µM sodium citrate (pH 5.8), 10 mM EDTA, and 30 mM β-mercaptoethanol. Forty microliters of a 10 mg/mL Zymolyase 20T stock solution was added, and the mixture was incubated at 37° C. for 20 minutes until 95% of the cells were spheroplasts. The spheroplasts were pelleted and washed twice in 5 mL of a solution of 1 M sorbitol in 10 mM Tris/Cl (pH 7.5), resuspended in 3 mL of the same solution, and counted. While the spheroplasts were being washed, the 16-9 cells were harvested by trypsinization, resuspended in serum free F-12 (Ham) medium (Sigma), and counted. Aliquots containing $6 \times 10^7$ spheroplasts were placed in 15-mL tubes and centrifuged at 500×g for 5 minutes. The supernatant was removed from the protoplast pellet and 5 ml of the cell suspension containing $3 \times 10^6$ 16-9 cells was added carefully. The cells were then centrifuged at 500×g for 5 minutes. The supernatant was removed and 50 µL of serum-free F12 medium was added to resuspend the pellets. Five hundred microliters of 45% (w/v) PEG 1500 solution (Boehringer Mannheim Biochemicals) containing 5% (v/v) DMSO, 10 µM β-mercaptoethanol, and 5 mM $CaCl_2$ were added to the mixed cell suspension. The cells were mixed by tapping the tube briefly, incubated for 2 minutes at room temperature, then diluted with 5 mL of serum-free F12 medium. This cell suspension was left at room temperature for 20 minutes, then centrifuged at 600×g for 6 minutes. The resulting pellet was resuspended in 5 mL of complete F12 medium and plated at $1.5 \times 10^6$ eukaryotic cells per 150 mm plate. Thirty six hours later, plates were washed with phosphate-buffered saline (PBS) to remove dead cells and yeast, then refed with complete F12 medium containing 450 µg/mL of antibiotic G418 (Gibco). Cells were refed as necessary, and resistant colonies typically appeared after 14 to 18 days.

Electrophoresis and Hybirdization Procedures

Agarose plugs were prepared as described (40). Yeast cells were grown to stationary phase at 30° C. in 50 mL of AHC media, washed twice with 25 mL of 50 mM EDTA (pH 8.0) by centrifugation at 3500×g for 5 minutes, followed by resuspension at a density of $1 \times 10^{10}$ cells/ml in 50 mM EDTA. An equal volume of 1% (w/v) Incert agarose (FMC BioProducts) in 50 mM EDTA (pH 8.0) and 20 µL of 10 mg/mL Zymolyase 20T per milliliter of agarose solution was added to the cell suspension and eighty microliters of the mixture was put into the plug mould. Spheroplasts were made by pushing plugs out of the mould into 1 mL of 0.5 M EDTA (pH 8.0) containing 7.5% β-mercaptoethanol per plug and incubating overnight at 37° C. with gentle shaking. The solution was removed and the plugs were rinsed twice with 50 mM EDTA (pH 9.25). The spheroplasts were lysed by transferring to Solution ESP [0.5 M EDTA (pH 9.25), 1% Sarkosyl (IBI), and 1 mg/mL proteinase K (Sigma)] and incubating for 94 hr at 50° C. For restriction enzyme digestion one quarter of a plug was treated twice with one milliliter of 1 mM phenylmethylsulfonyl fluoride (PMSF) in TE [10 mM Tris/Cl (pH 7.5), 0.1 mM EDTA] at room temperature to inactivate proteinase K. Then the plug was washed three times with the same TE buffer for 2 hour each and put into a 1.5 milliliter microtube along with reaction buffer and 5 units of NotI restriction endonuclease (New England Biolabs) in a volume of 100 µl. The mixture was incubated at 37° C. overnight. The agarose plugs were analyzed by pulsed field gel electrophoresis (PFGE) (CHEF, OWL Scientific Plastics, Inc). The gels measured 13 cm×13 cm, consisted of 120 mL of 1% agarose in TBE (0.045 M Tris/borate, pH 8.0, 2.5 mM EDTA), and were run at 170 V for 24 hr at 15° C. with a pulse time of 35 seconds. The DNAs were blotted onto Nytran (Schleicher & Schuell) with standard Southern blot procedures. DNA probes were labeled with [α-$^{32}$P]dCTP (NEN, 3000 Ci/mmol) with random hexadeoxynucleotides as primers (41).

Rescue of DNA Fragments Containing Alu Targeted Sites

Chromosomal DNA was prepared from the transformed YAC clones as described (39). The DNA was digested with restriction endonuclease XhoI, separated on a 0.8% agarose gel, blotted onto a nylon membrane, and probed with a radiolabeled neo gene fragment in order to identify the size of XhoI fragment containing the neo gene. The appropriate DNA band was excised from the agarose gel and purified with Geneclean (Bio101, La Jolla, Calif.). The DNA fragments were ligated to XhoI-digested, and alkaline phosphatase-treated pBluescript KS+/± (Stratagene). The resulting plasmids were transformed into *E. coli* INV/ which were then plated at a density of about 300 colonies per 150 mm Petri dish containing LB medium and 50 µg/ml ampicillin. The colonies were blotted onto nylon membranes and probed with the radiolabeled neo gene fragment to identify clones having one end of the integration site.

Construction of Cosmid Library from YAC Clones

A high molecular weight chromosomal DNA was made from YAC D142H8 as described (39). Ten micrograms of the DNA were incubated with 0.5 unit of restriction endonuclease MboI (BRL) in a 100 µl volume. After 1, 5, 10, 20, and 30 minutes incubation, 20 µl of the mixture was taken and run on field inversion gel electrophoresis (FIGE) with standard program No. 3 (PPI-200, M. J. Research Inc.) which is suitable to resolve DNA up to 200 kb. A ten minute digestion was chosen since it yielded a 50 to 100 kb size distribution. Then 10 µg of the DNA was digested with MboI restriction endonuclease as described above for 10 minutes, extracted with phenol and phenol/chloroform (1:1), treated with alkaline phosphatase, and precipitated with ethanol. Five µg of the cosmid vector SuperCos1 (Stratagene) was cut with endonuclease XbaI, treated with alkaline phosphatase, and cut again with endonuclease BamHI to get two fragments (1.1 kb and 6.5 kb). Then 2.5 µg of digested chromosomal DNA and 1 µg of digested SuperCos1 were ligated in a 20 µl volume. After ligation, 2 µl of the DNA mixture was packaged with extract (Gigapack II plus, Stratagene) according to the manufacturer's procedure. The infected *E. coli* AG1 cells were plated onto LB plates containing 50 µg/ml of ampicillin at a density of about 300 colonies per 150 mm Petri dish for screening.

Yeast Artificial Chromosome Fragmentation Vectors

Materials and Methods

Yeast Strains

Yeast host strain AB1380 containing a 540 kb YAC ('B8') and was grown in AHC medium (1.7 g yeast nitrogen base without amino acids, 5.0 g of $(NH_4)_2SO_4$, 10 g of casein hydrolysate, 20 µg adenine hemisulfate and 2% (w/v) glucose per liter). This host strain was transformed to a Trp$^+$, Ura+phenotype by introduction of the GART YAC. The compound 5-fluoro-orotic acid (5-FOA, obtained from PCR, Inc., Gainesville, Fla.) was used to obtain Ura− clones according to the method of McCusker and Davis (63). The Ura+ strain containing the B8 YAC was plated on 2% agar plates containing 0.17% yeast nitrogen base without amino acids and ammonium sulfate, 0.1% proline, 2% glucose, 10 µg/ml uracil, 50 µg/ml 5-FOA, 10 µg/ml adenine sulfate, 50 µg/ml lysine and 20 µg/ml histidine to obtain URA3− cells. Potential ura3− mutants were picked, streaked for single colonies, and characterized with regard to growth without uracil. A clone containing the B8.ura.2 YAC was selected for further use.

Vector Construction

Figure 10:
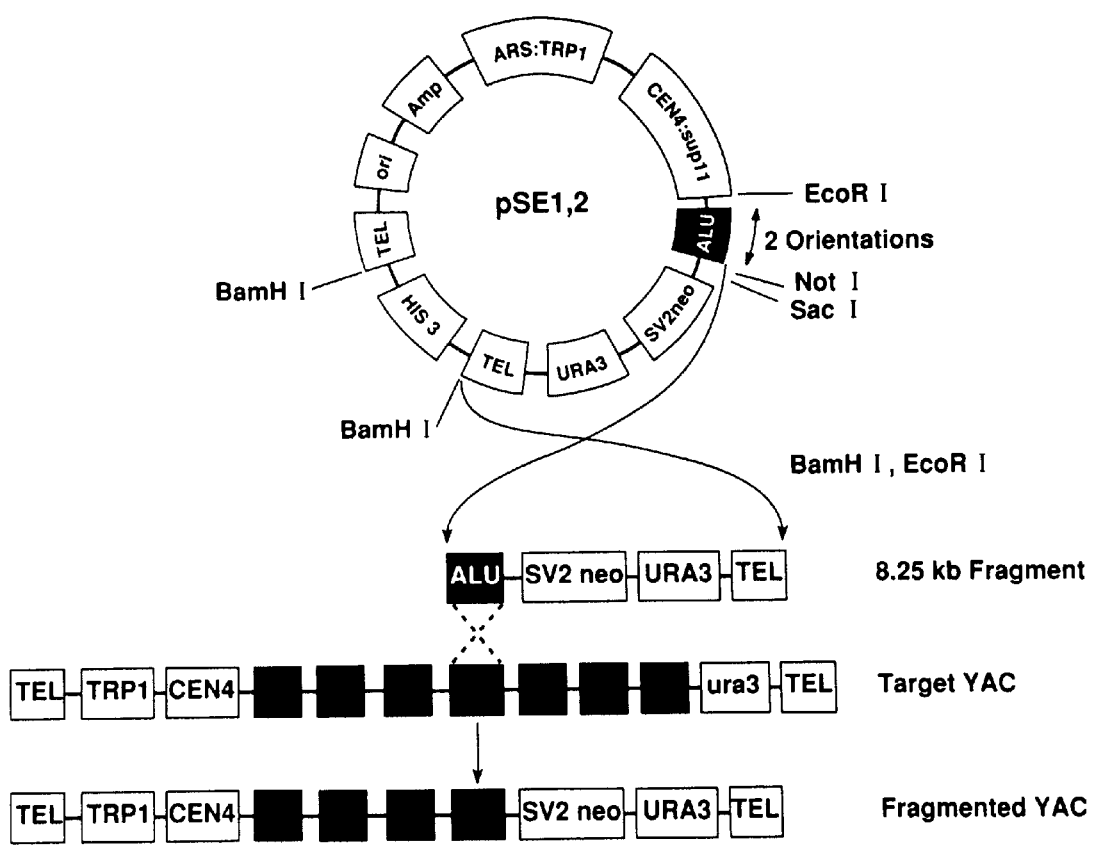
FIG. 10 illustrates a schematic map of fragmentation vectors pSE1 and pSE2, and the procedure used for fragmentation of the parental GARTD142H8.ura.2 YAC. TEL=telomere; CEN=centromere.

A plasmid containing the human repetitive Alu sequence Blur-13 (pBP47, obtained from Dr. Roger H. Reeves, Johns Hopkins Univ.) was modified by removal of the EcoRI site. After digestion with restriction endonuclease EcoRI, the ends were filled in with the Klenow fragment of DNA polymerase I. An 8 bp ClaI linker was then inserted at this location, adding a total of 12 bp to the Alu sequence. This modified Blur-13 fragment of about 300 bp was released with restriction endonuclease BamHI, made built-ended with the Klenow fragment of *E. coli* DNA polymerase I and isolated with Geneclean Plus (Bio 101, La Jolla, Calif.). This fragment was ligated into the SmaI site of pBluescript KS+ and clones containing the Blur-13 fragment in both orientations were selected. The orientation of the Blur-13 fragment was determined by using an asymmetric BglI site located at position 109 in the Blur-13 fragment. Following this, the BamHI site was removed from the polylinker in these clones by digesting with the restriction endonuclease BamHI and filling in the 5'-overhang with the Kienow fragment of *E. coli* DNA polymerase I. The Blur-13 fragments were released from these modified Bluescript vectors with EcoRI and NotI restriction endonucleases. The EcoRI-NotI fragments, containing Blur fragments in both orientations, were then cloned into the plasmid pYAC4DRI+Sup11, SV2NEO (a gift from Dr. Jules O'Rear, Robert Wood Johnson Medical School, UMDNJ) to form pSE1 and pSE2, differing only in the orientation of the Blur sequence (FIG. 10).

Yeast Transformation

The yeast strain containing the YAC B8.ura.2 was transformed to Ura+ with the fragmentation vectors pSE1 and pSE2. First, DNA was prepared from each of these vectors by digestion with EcoRI and BamHI restriction enzymes. The DNA fragments were then dephosphorylated with calf intestinal alkaline phosphatase. The protein was denatured with phenol/chloroform/isoamyl alcohol (25:24:1) extraction three times, and the DNA was precipitated with ethanol. Twenty-five µg of DNA (a mixture of 12.5 µg of each plasmid) was used to transform $5 \times 10^7$ yeast cells containing YAC B8.ura.2 as reported (39). Ura+ transformants were selected on uracil-deficient plates and 27 clones were chosen for analysis.

Transformation of Mammalian Cells

Chinese hamster ovary (CHO) cells were transformed by neo+ yeast according to Pavan et al. (33). Briefly, approximately $2 \times 10^7$ CHO cells were fused to 5 ml of a confluent yeast culture as described (33). After 24–36 hr in F-12 medium plus 10% fetal bovine serum, the cells were washed twice with PBS. Transformants were selected by 450 µg/ml of G418.

Localization of the Human Interferon-gamma Receptor Accessory Factor Gene

Cells

The hamster/human somatic cell hybrid 16-9 which contains human Chromosome 6q was maintained in F-12 medium containing 10% fetal bovine serum. These cells had been transfected with a genomic clone for the class I HLA-B7 antigen (98,105). The cell lines which were transformed by fragmented YACs were maintained in the same medium plus 400 µg/ml G418. The 153B7-8 cell line, defined previously (98) is a Chinese hamster ovary (CHO-K1) cell line which contains human Chromosome 21q, and the HLA-B7 antigen gene; 153B7-8[HHH] refers to the same cell line which has been transfected with the Hu-IFN-gamma R cDNA. Both of these cell lines were maintained as described earlier (101,107). The 3x1S cell line is a CHO-K1 cell line which contains 1–3 MBA of human Chromosome 21 (104).

Reagents, Restriction Endonucleases and Other Enzymes

Human IFN-gamma, with a specific activity of $1.3 \times 10^7$ units/mg, was isolated from *Escherichia coli* as described (108). Human IFN-α/A/D(Bgl) was prepared as reported (109,110) and had a specific activity of $6.0 \times 10^7$ units/mg. Human IFN-gamma was isolated as described (111,112) and had a specific activity of $3.5 \times 10^7$ units/mg. Restriction endonucleases were obtained from New England Biolabs and Boehringer Mannerism.

Construction of Fragmented YACs

The parental GART YAC (GART D142H8) was obtained through the "chromosome 21 joint YAC screening effort" (directed by Dr. David Patterson, Eleanor Roosevelt Institute, Denver, Colo.). The plasmids pSE1 and pSE2 were constructed in such a way that BamH1 and EcoRI digestion releases an 8.4 kb fragment containing an Alu sequence, an SV2neo gene, a URA3 gene and a yeast telomere, in that order (106,113). The plasmids pSE1 and pSE2 (12.5 µg of each) were so digested and the 8.4 kb fragment was isolated and used to transform the yeast strain GART D142H8.ura.2 which contains the parental GART YAC and had been converted to a Ura− phenotype by 5-fluoroorotic acid selection (106). Transformations were performed as described (113) and Ura+ transformants were obtained on uracil-deficient plates.

Fusion of Fragmented YACs to Mammalian Cells

Approximately $2 \times 10^7$ 16-9 cells were fused to 10 ml of a 5% confluent yeast culture with PEG (113). After 24–36 hours in F-12 medium plus 10% fetal bovine serum and 50 µg/ml gentamycin, the cells were washed twice with phosphate-buffered saline (PBS) and the transformants were selected in the same medium containing 450 µg/ml antibiotic G418.

MHC Analysis

Induction of MHC class I antigens by IFN was assayed as reported (101,110). For each sample, 10,000 cells were analyzed with a Coulter Epics Profile cytofluorograph and Cytologic software.

Assay of the Transcription Factors ISGF3-gamma and GAF

For factor ISGF3-gamma, cells transformed by fragmented YACs were incubated with or without 100 units/ml IFN-gamma, for 18 hours. The cells were harvested by trypsin-EDTA treatment, washed once in F-12 plus 10% fetal bovine serum and once in PBS. Lysates were prepared from the cell pellets and gel shift assays were conducted as described (114). GAF was assayed as described (115) after cells had been incubated with or without 100 units/ml IFN-gamma for 30 minutes.

Antiviral Assays

The cell lines 16-9, J18/16-9, J29/16-9 and 153B7-8 [HHH] were assayed for resistance to encephalomyocarditis virus (EMCV) as detailed previously (110,116). Forty thousand cells were plated per well and EMCV was present at 4,000 pfu/well.

cDNA Clone Encoding an Accessory Factor

Reagents, Restriction Endonucleases and Other Enzymes

All restriction endonucleases were purchased from New England Biolabs; DNase I was from Worthington Biochemicals; Sequenase was from United States Biochemical Corporation; T4 DNA ligase was from Boehringer Mannerism. [$\alpha$-$^{32}$P]dCTP and [gamma-$^{32}$P]ATP were from New England Nuclear. Acrylamide, formamide and all other reagents were analytical grade and purchased from United States Biochemical Corp.

Cells and Media

The 16-9 hamster/human somatic cell hybrid line is a Chinese hamster ovary (CHO-K1) hybrid containing a translocation of the long arm of human Chromosome 6 and a transfected human HLA-B7 gene (14,15,65). These cells are unresponsive to treatment with Hu-IFN-gamma. The 3x1S cells are CHO-K1 cells that contain a small 1–3 MBA region of human Chromosome 21 (65,22,46). The 16-9 cells were maintained in F12 (Ham) medium (Gibco) containing 10% heat-inactivated fetal bovine serum (Sigma), and 50 µg/ml gentamicin sulfate (complete F12 medium). The 3x1S cells were maintained in F12D (Ham) medium (Gibco) containing 10% dialyzed heat-inactivated fetal bovine serum (Sigma), and 50 µg/ml gentamicin sulfate (complete F12D medium). YACs were obtained, maintained and grown in AHC media as reported (65).

Isolation of RNA and DNA

Total polyadenylated RNA was isolated from Raji, HL60 and 3x1S cells as described (66). DNA was prepared by minor modification of previously reported procedures (24, 67–69). High molecular weight DNA was prepared from Daudi cells and human placenta by the procedure of Blin and Stafford (69)

Construction of Cosmid Library from YAC Clones and Genomic Walking

Figure 12:
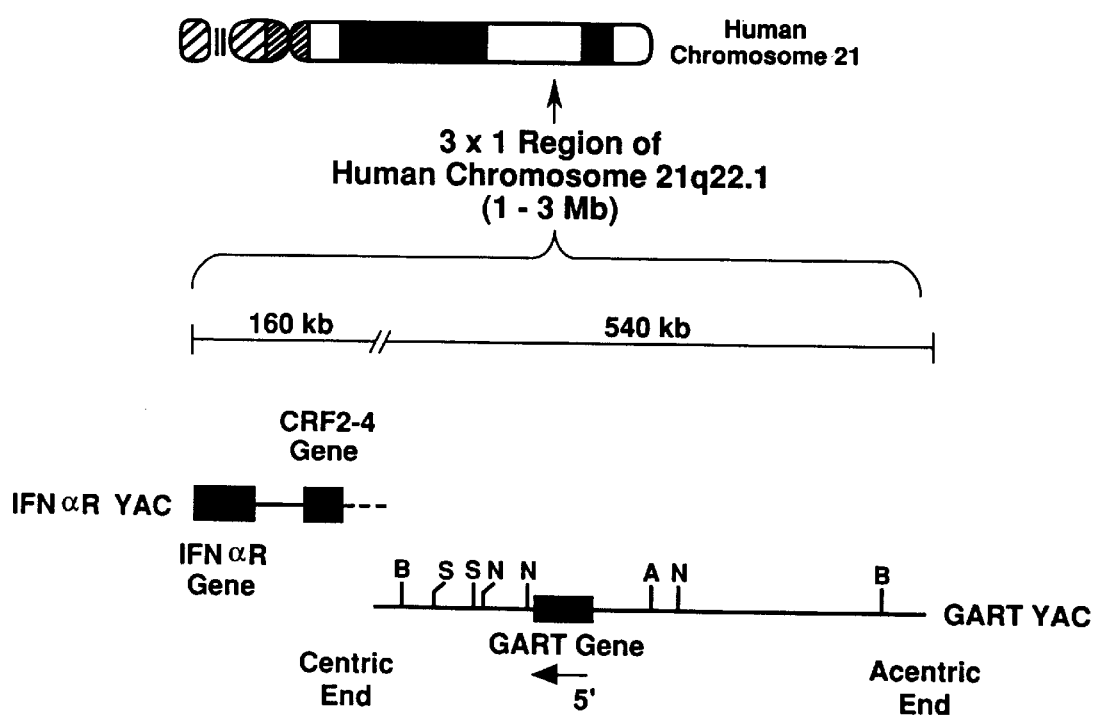
FIG. 12 shows the accessory factor and interferon α/βreceptor region of chromosome 21q.

Genomic cosmid libraries from 3x1S cells and human cells were prepared as described (46). A high molecular weight chromosomal DNA was made from YAC D142H8 (65) or J18 (70,71) as described (39). Ten micrograms of the DNA was incubated with 0.5 unit of restriction endonuclease MboI (BRL) in a 100 µl volume. After 1, 5, 10, 20, and 30 minutes incubation, 20 µl of the mixture was taken and run on field inversion gel electrophoresis (FIGE) with standard program No. 3 (PPI-200, M. J. Research Inc.) which is suitable to resolve DNA up to 200 kb. A ten minute digestion was chosen since it yielded a 50 to 100 kb size distribution. Then 10 µg of the DNA was digested with MboI restriction endonuclease as described above for 10 minutes, extracted with phenol and phenol/chloroform (1:1), treated with alkaline phosphatase, and precipitated with ethanol. Five µg of the cosmid vector SuperCos1 (Stratagene) was cut with endonuclease XbaI, treated with alkaline phosphatase, and cut again with endonuclease BamHI to get two fragments (1.1 kb and 6.5 kb). Then 2.5 µg of digested chromosomal DNA and 1 µg of digested StiperCos1 were ligated in a 20 µl volume; two µl of the ligated DNA mixture was packaged with extract (Gigapack II plus, Stratagene) according to the manufacturer's procedure. The infected *E. coli* AGI cells were plated onto LB plates containing 50 µg/ml of ampicillin to a density of about 300 colonies per 150 mm Petri dish for screening. About 150 cosmid clones which were positive to human Cot 1 DNA (BRL) were selected. Then Cot 1 positive cosmids were screened with the radiolabeled TRP1 and URA3 gene fragments to identify the cosmids GC3-59 and JC8 corresponding to YAC centric and acentric arms, respectively. A 1.5 kb fragment from the T3 RNA polymerase end of the cosmid GC3-59 free of repetitive human DNA was used to identify the overlapping cosmids GC8-3 and GC8-10. A 700 bp fragment free of repetitive human DNA from the T7 end of the cosmid GC8-10 was used to identify the cosmid JC35 (FIG. 12).

Preparation and Screening of cDNA Libraries; Sequencing of DNA

A cDNA library from 3x1S cells was constructed in phage lambda pCEV27 (72) by the automatic directional clonig method (73). The library consisted of $1.5 \times 10^7$ independent clones and nearly all phages contained cDNA inserts. A part of the library was amplified and used for screening. Previously prepared libraries from mRNA from M426 human cells in lambda pCEV15 (73) and from mRNA from human Daudi lymphoblastoid cells (plasmid pCDNA1 custom library prepared by Invitrogen; a gift from J. A. Langer) were used as well. Screening of cDNA and genomic libraries with DNA probes was performed as described previously (24). The cDNA clones were sequenced by a modification of the dideoxy chain termination method (74,75). SP6, T7 and internal primers generated from the sequence were used to prime the sequencing reactions with double-stranded templates.

Hybridization Procedures

DNA used as probes in the hybridization reactions represented the entire insert of the cDNA clones unless otherwise noted and was labeled by the random oligonucleotide primer labeling method according to standard techniques (68,41). All hybridization reactions were carried out in 50% formamide, 5xSSC, 5xDenhardt's reagent, 0.1% SDS, 100 µg/ml yeast tRNA and 0.1 µg/ml of poly(A) (Collaborative Research, Inc.) overnight (about 16 hours) at 42° C. The hybridization blots were washed stringently with 0.1xSSC, 0.1% SDS at 65° C.

In order to determine the size of the accessory factor mRNA, 1 µg of polyadenylated RNA from various cells was fractionated on a 1.2% agarose formaldehyde gel and blotted onto a nylon membrane (Nytran, Schleicher and Schuell. For Southern blots, DNA (10 µg) was digested with EcoRI and HindIII restriction endonucleases. The restriction digests were electrophoresed on a 20 cm 0.8% agarose gel and blotted onto the nylon membrane.

The Northern and Southern blots were hybridized with $^{32}$P-labeled DNA under conditions described above. The blots were washed stringently, as described above, then autoradiographed with Kodak XAR-5 film and a Cronex Lightning Plus intensifying screen (DuPont) at −70° C. for 48 hours.

To suppress signals from repetitive human sequences, 25 ng of the genomic DNA fragment was labeled by random priming (41) to high specific activity ($10^9$ cpm/μg) followed by denaturation of the probe in a large excess of sheared human DNA (1 mg/ml) (human Cot1 DNA, GibeoBRL), and pre-annealing at 68° C. in 6×SSC for 10 minutes to Cot 10 (76).

Computer Analysis of Sequence Data

The Wisconsin GCG software package (77) was used to assemble a composite sequence from the sequences of the various fragments and for other computer analyses of the data. Optimal alignments between the sequences were made by the algorithm of Needleman and Wunsch (78). The hydrophobicity plot of the deduced amino acid sequence was done according to the method of Kyte and Doolittle (79).

Transfection of 16-9 Cells

Transfections were performed as previously described (17,25,68). After transfection, the cells were incubated for 20 hours at 35° C. in a 3% $CO_2$ atmosphere, after which the medium was removed, the cells were washed twice with phosphate-buffered saline, and incubated in fresh medium in 5% $CO_2$ at 37° C. for 20 hours. The cells were then trypsinized, split at a ratio of 1:10, and incubated in medium under the same conditions for 20 hours before selection by resistance to antibiotic G418 (450 μg/ml).

Cytofluorographic Analysis of Cells for Expression of the HLA-B7 Surface Antigen Cytofluorographic analysis of cells for expression of the HLA-B7 surface antigen was performed as described in detail previously (17,20,65,25). Clones or pools of cells were analyzed as noted. Samples were analyzed on a Coulter Epics Profile Cytofluorograph with a 15-milliwatt Argon laser tuned to 488 nm. Forward and 90° angle light scatter as well as integrated log green fluorescence signals (with a 488 nm long-pass laser blocking filter and 525 nm band-pass filter in place) were collected and analyzed. For each analysis, 10,000 events were accumulated and analyzed on the CytoLogic software as described (80,25). Hu-IFN-αA/D, a human interferon active on hamster cells (80), was used as a control to demonstrate the integrity of the HLA-B7 gene in the hamster cells.

Antiviral Assay

Transfected cells were assayed for resistance to encephalomyocarditis virus (EMCV) and vesicular stomatitis virus (VSV) by a cytopathic effect inhibition assay (42).

TABLE 1

Functional Assay of YAC Clones

| Locus | Probe Name | Address of YAC | Size of YAC(kb) | YAC.neo$^r$ | No of G418 Resistant Colonies | NHC Response |
|---|---|---|---|---|---|---|
| D21S65 | 525 | 8119G7 | 1200 | 525 B119G7.neo.1 | 2 | − |
|  |  |  |  | 525 B119G7.neo.18 | 0 | NA |
|  |  | D165D7 | 210 | 525 A165D7.neo.12 | 0 | NA |
|  |  |  |  | 525 A165D7.neo.16 | 0 | NA |
|  |  | C4C10 | 220 | 525 C4C10.neo.3 | 0 | NA |
|  |  |  |  | 525 C4C10.neo.20 | 0 | NA |
|  |  | C14B2 | 450 | 525 C14B2.neo.2 | 0 | NA |
|  |  |  |  | 525 C14B2.neo.19 | 0 | NA |
| D21S17 | H8 (517) | A222A12 | 220 | H8(517)A222A12.neo.6 | 0 | NA |
|  |  |  |  | H8(517)A222A12.neo.13 | 3 | − |
| D21PFGS | GART | D142H8 | 540 | GARTD142H8.neo.3 | 4 | + |
|  |  |  |  | GARTD142H8.neo.16 | 1 | − |
|  |  |  |  | GARTD142H8.neo.18 | many | + |
| D21S55 | 518 | A234B10 | 210 | 518A234B10.neo.2 | 0 | NA |
|  |  |  |  | 518A234B10.neo.15 | 0 | NA |
|  |  | B134B9 | 225 | 518B134B9.neo.8 | 0 | NA |
| D21SOD1 | SOD | D112A5 | 180 |  | 0 | NA |
|  |  |  | 120 |  | 0 | NA |
| D21IFNAR | IFNAR | B49F1 | 150 | IFNARB49F1.neo.32 | 5 | − |
|  |  |  |  | IFNARB49F1.neo.35 | 0 | NA |

The "MHC Response" of the last column represents Human class I HLA antigen induction upon treatment with Hu-IFN-gamma: − represents no response; + represents a positive response; NA, not applicable. Transfected cells were tested as pools of G418-resistant colonies. The SOD D112A5 YAC was not tested for HLA induction since a neo$^r$-positive YAC was not obtained from the transformation. The dish of transformants with GARTD142H8.neo.18 (YAC-JS2) contained many small colonies.

TABLE 2

Antiviral Effects of Hu-IFN-gamma on Transfected CHO cells

| Cell Line | DNA Transfected | IFN | ED$_{50}$ (units/ml) |
|---|---|---|---|
| 153B7-8 | Hu-IFN-gamma R cDNA | Hu-IFN-gamma | 2 |
| 3x1S | Hu-IFN-gamma R cDNA | Hu-IFN-gamma | 14 |
| 16-9 | YAC-JS2 | Hu-IFN-gamma | >10000 |

Transfected cells were assayed for resistance to EMCV by a cytopathic effect inhibition assay (42). The 153B7-8 cells are CHO-K1 cells containing a transfected HLA-B7 gene and human Chromosome 21q (15, 25). Irradiation-reduced somatic cell hybrid 3x1S cells containing a 1–3 MBA fragment of human Chromosome 21q were described (22). The somatic cell hybrid 16-9 cells contain human HLA-B7 gene and human Chromosome 6q encoding the Hu-IFN-gamma receptor. The $ED_{50}$ represents the concentration of IFN-gamma (units/ml) which provided 50% protection of cells against EMCV. All the cells were protected from EMCV infection by Hu-IFN-αA/D(Bgl) in control experiments. Each of these cell lines were derived from the same parental CHO-K1 cells.

TABLE 3

Distribution of the Size of Deletions.

| Size of Deletion (kb) | No. of Deleted Clones (%) |
| --- | --- |
| 0–20 | 38 (63.3%) |
| 20–100 | 17 (28.3%) |
| >100 | 5 (8.3%) |

TABLE 4

Characteristics of fragmented YACs produced by URA3 transformation

| YAC Characteristics | Percentage | Fraction |
| --- | --- | --- |
| YACs < 540 kb78% | 78% | (21/27) |
| YACs > 540 kb | 11% | (3/27) |
| URA+ clones with no apparent YAC | 11% | (3/27) |
| 80 kb ≦ YACs < 150 kb | 48% | (13/27) |
| 150 kb ≦ YACs < 350 kb | 7% | (2/27) |
| 350 kb ≦ YACs < 540 kb | 22% | (6/27) |
| YACs positive for GART gene | 59% | (16/27) |
| YACs positive for GC8.10E6 | 89% | (24/27) |

YACs were analyzed by pulsed-fuel gel electrophoresis at a field strength of 170 V. Their size was determined relative to *Saccharomyces cerevisiae* chromosomal DNA standards. YACs selected for further mapping include J29 (500 kb), J28 (475 kb), J16 (350 kb), and J18 (150 kb). The genotype of these YAC strains is neo+, TRP1, URA3.

TABLE 5

Amino Acid Composition of Human Interferon gamma Accessory Factor-1

| | Complete Protein | | Mature Protein | |
| --- | --- | --- | --- | --- |
| Residue | Number Percent | Mole | Number Percent | Mole |
| Ala | 25 | 7.4 | 19 | 6.1 |
| Cys | 6 | 1.8 | 6 | 1.9 |
| Asp | 16 | 4.7 | 15 | 4.8 |
| Glu | 16 | 4.7 | 16 | 5.2 |
| Phe | 18 | 5.3 | 17 | 5.5 |
| Gly | 14 | 4.1 | 13 | 4.2 |
| His | 6 | 1.8 | 6 | 1.9 |
| Ile | 20 | 5.9 | 20 | 6.5 |
| Lys | 13 | 3.9 | 13 | 4.2 |
| Leu | 37 | 11.0 | 29 | 9.4 |
| Met | 5 | 1.5 | 4 | 1.3 |
| Asn | 11 | 3.3 | 11 | 3.5 |
| Pro | 25 | 7.4 | 21 | 6.8 |
| Gln | 17 | 5.0 | 17 | 5.5 |
| Arg | 12 | 3.6 | 11 | 3.5 |
| Ser | 31 | 9.2 | 30 | 9.7 |
| Thr | 20 | 5.9 | 19 | 6.1 |
| Val | 24 | 7.1 | 23 | 7.4 |
| Trp | 9 | 2.7 | 8 | 2.6 |
| Tyr | 12 | 3.6 | 12 | 3.9 |
| Total | 337 | 100 | 310 | 100 |

TABLE 5-continued

Amino Acid Composition of Human Interferon gamma Accessory Factor-1

| | Complete Protein | | Mature Protein | |
| --- | --- | --- | --- | --- |
| Residue | Number Percent | Mole | Number Percent | Mole |
| Ala + Gly | 39 | 11.6 | 32 | 10.3 |
| Ser + Thr | 51 | 15.1 | 49 | 15.8 |
| Asp + Glu | 32 | 9.5 | 31 | 10.0 |
| Asp + Glu + Asn + Gln | 60 | 17.8 | 59 | 19.0 |
| His + Lys + Arg | 31 | 9.2 | 30 | 9.7 |
| Asp + Glu + His + Lys + Arg | 63 | 18.7 | 61 | 19.7 |
| Ile + Leu + Met + Val | 86 | 25.5 | 76 | 24.5 |
| Phe + Trp + Tyr | 39 | 11.6 | 37 | 11.9 |

The amino acid composition of the coding sequence of human IFN-gamma AF-1 from positions 1–337 (complete pre-protein) and 28–337 (the estimated mature protein) are given. The molecular weight of the polypeptide including the signal peptide is 37,834; the mature protein, 35,034. The isoelectric point of the mature protein is calculated to be pH 5.42. The analysis presents the coding sequence of plasmid pSK1.

TABLE 6

Homology of the Class 2 Receptor Family to Human AF-1

| Receptor | Amino Acids in Domain | % Identity | % Similarity |
| --- | --- | --- | --- |
| Human CRF2-4 | 201 | 29.6 | 48.7 |
| Human IFN-gamma R | 228 | 21.0 | 42.9 |
| Murine IFN-gamma R | 227 | 25.8 | 46.4 |
| Human IFN-gamma R | | | |
| N-term | 197 | 25.0 | 50.0 |
| C-term | 212 | 24.9 | 49.2 |
| Murine IFN-gamma R | | | |
| N-term | 198 | 22.4 | 48.4 |
| C-term | 220 | 23.5 | 42.6 |
| Bovine IFN-gamma R | | | |
| N-term | 200 | 25.8 | 46.8 |
| C-term | 200 | 22.7 | 40.1 |

Percent homology to the extracellular domain of the human IFN-gamma AF-1 mature protein as determined by the alignment method of Gribskov and Burgess (93) as written for the GCG Sequence Analysis Software Package (Madison, Wis.).

TABLE 7

Antiviral (EMCV) Activity of Interferons in Cell Lines Stably Fused with YACs Containing the Human Chromosome 21 Accessory Factor Gene

| | IFN Concentration (units/ml) Providing Half-maximal Protection | | | |
| --- | --- | --- | --- | --- |
| Interferon | 16-9 Cells | J18/16-9 Cells | J29/16-9 Cells | 153B7-8 Cells [HHH] |
| Hu-IFN-αA/D(Bgl) | 528 | 264 | 378 | N.D. |
| Hu-IFN-β | 700 | 172 | 112 | N.D. |
| Hu-IFN-gamma | (>3,250) N.P. | (>3,290) N.P. | (>13,000) N.P. | 3.2 |

Interferons were tested over the following concentration ranges: For 16-9 cells (the untransfected host) and J-18/16-9 cells, all interferons were tested from 0.06 to 250 ng/ml. For J29/16-9 cells, the interferons were tested from 0.24 to 1,000 ng/ml. Specific activity of the interferons used was: Hu-IFN-αA/D(Bgl), $6.0 \times 10^7$ units/mg; Hu-IFN-β, $3.5 \times 10^7$ units/mg; Hu-IFN-gamma, $1.3 \times 10^7$ units/mg. N.P. designates no protection observed at maximal Hu-IFN-gamma concentration tested; N.D., not done. HHH indicates that the Hu-IFN-gamma receptor cDNA was transfected into the cell.

Figure 1A:
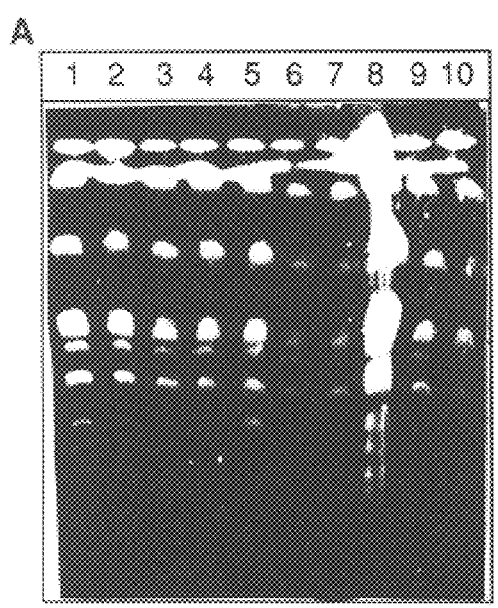
FIG. 1A shows a pulse field gel electrophoresis of nine YAC clones from the 3x1S region of human chromosone 21q.
Figure 1B:
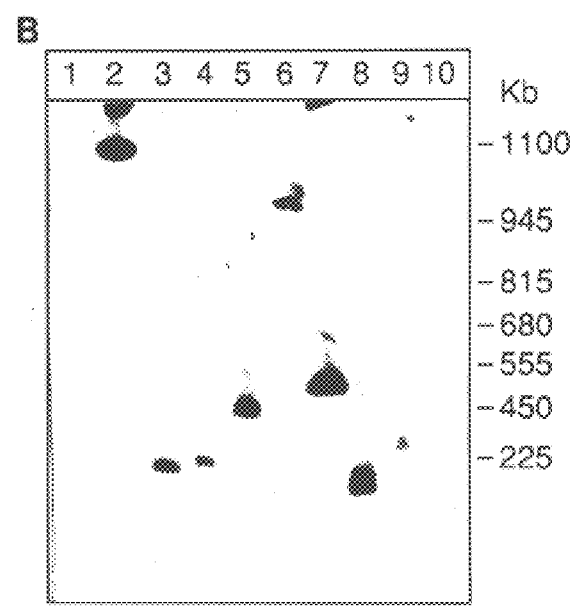
FIG. 1B shows Southern hybridization of the pulse field gel electrophoresis gel.

FIG. 1 shows a pulse field gel electrophoresis of various YACs and hybridization to total human DNA. Panel A: PFGE analysis of 9 YAC clones from the 3x1S region of human Chromosome 21q. Lane 1, *S. cerevisiae* AB1380; lane 2, 525 B119G7 (1200 kb); lane 3, 525 A165D7 (210 kb); lane 4, 525 C4C10 (220 kb); lane 5, 525 C14B2 (450 kb), lane 6, H8(517) A222A12 (220 kb); lane 7, GART D142H8 (540 kb); lane 8, 518 A234B10 (210 kb); lane 9, 518 B134B9 (225 kb); lane 10, SOD D112A5 (180 kb, 120 kb). IFNAR B49F1 (150 kb) is not shown here. Panel B: Southern hybridization of the PFGE gel. The blot from Panel A was probed with total human DNA labeled by random priming. The size of each YAC is shown above in parentheses. The numbers to the right of the blot indicate the size of various fragments in kilobase pairs (kb).

Figure 2:
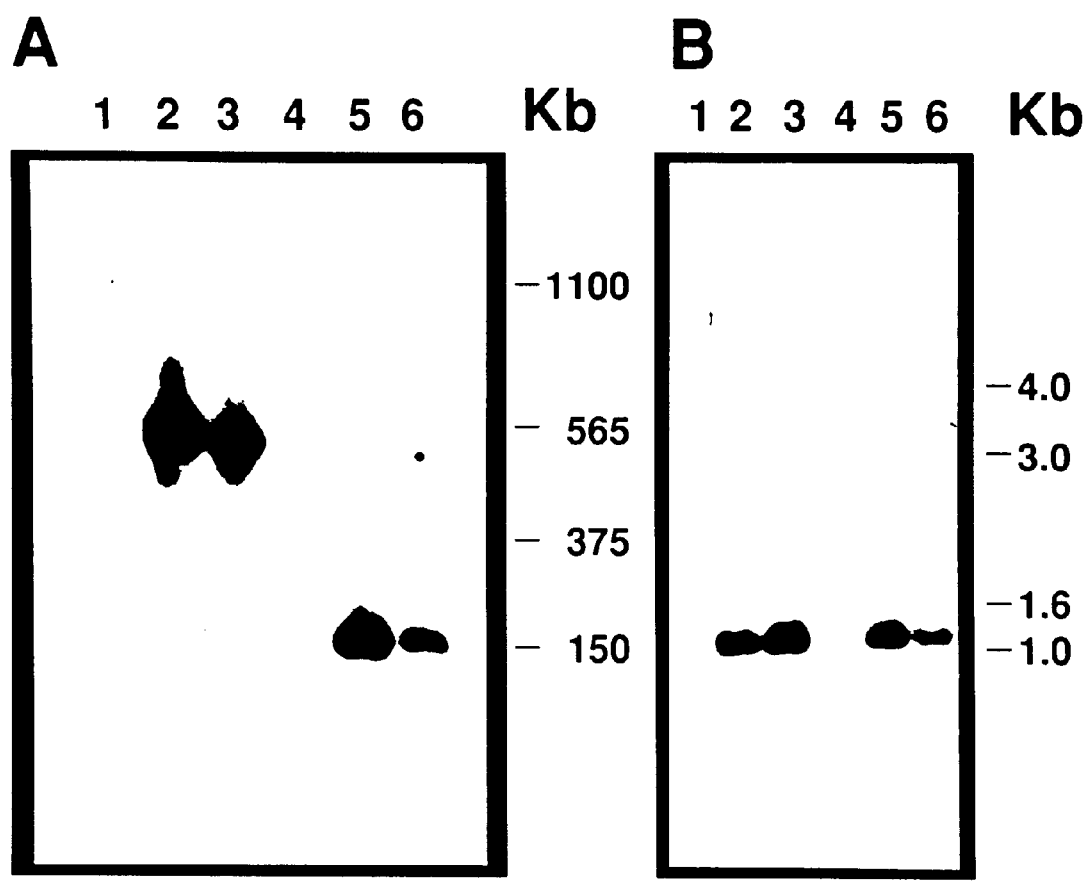
FIG. 2 illustrates a Southern hybridization.

FIGS. 2A–2B illustrates a Southern hybridization.

A: The agarose plugs from neo$^r$ Lys$^{2+}$ transformants derived from each YAC clone were analyzed by PFGE and the blot was probed with the labelled neo$^r$ gene to determine whether or not the neo$^r$ gene was targeted to the YAC. Lane 1, GART D142H8; lane 2, GART D142H8.neo.16; lane 3, GART D142H8.neo.18; lane 4, IFNAR B49F1; lane 5, IFNAR B49F1.neo.32; lane 6, IFNAR B49F1.neo.35 YACs are shown here as example. The GART D142H8.neo.18 (lane 3) clone contains smaller YACs than the original one (GART D142H8), possibly resulting from deletions generated by homologous recombination between two Alu sequences on the original YAC during the integration process.

B: Yeast chromosomal DNAs from the same YAC clones as in A were digested with BamHI and XhoI to release the neo$^r$ gene cassette and the blot was probed with the labelled neo$^r$ gene. Each targeted YAC clone shows a 1.1 kb fragment hybridizing to the probe suggesting that the neo$^r$ gene cassette was integrated intact into the YAC.

Figures 3, 3A, 3B, 3C, 3D:
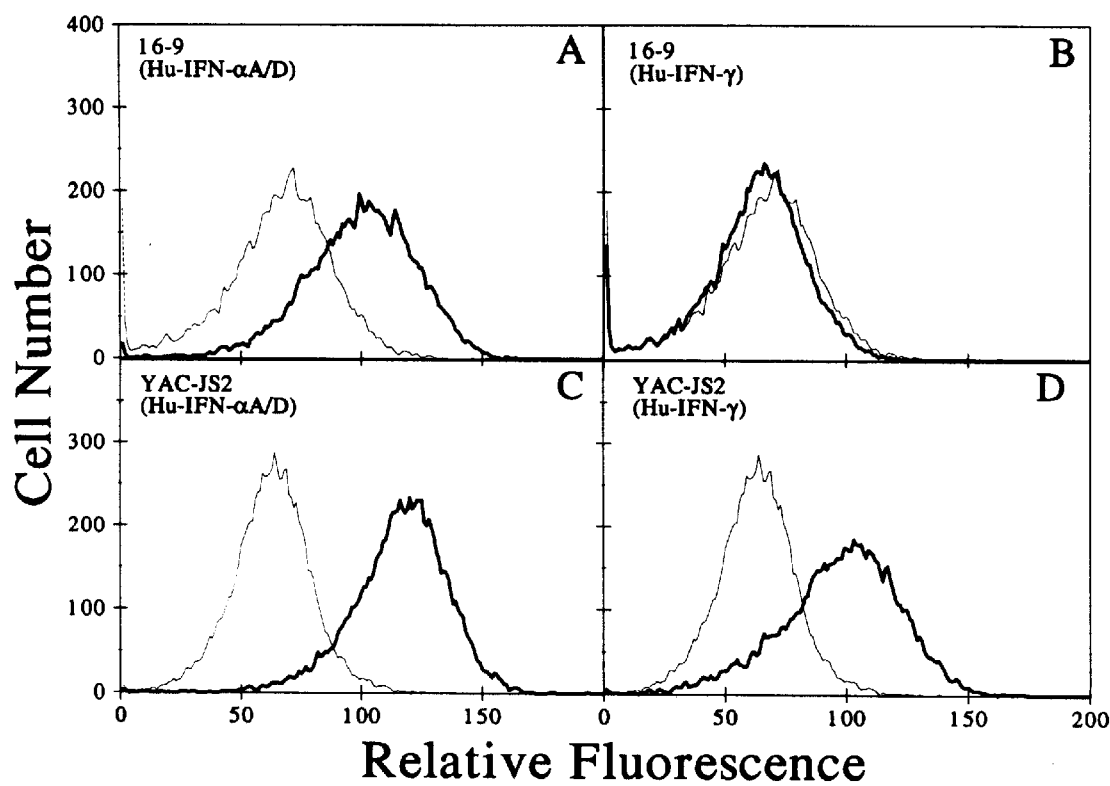
FIG. 3 shows the induction of HLA-B7 surface antigen in 16-9 cells fused with the YAC-JS2.
FIG. 3A and FIG. 3B represent 16-9 cells.
FIG. 3C and FIG. 3D represent pools of 16-9 fused to YAC-JS2, the GART D142H8.neo.18 YAC clone.

FIG. 3 shows the induction of HLA-B7 surface antigen in 16-9 cells fused with the YAC-JS2. The HLA- B7 antigen was detected by treatment of cells with mouse anti-HLA monoclonal antibody (W6/32) followed by treatment with FITC-conjugated anti-mouse IgG. The cells were analyzed by cytofluorography. Panels A and B represent 16-9 cells and panels C and D pools of 16-9 cells fused to YAC-JS2, the GART D142H8.neo.18 YAC clone. The thin line indicates cells not treated with IFN and the heavy line indicates treatment with 1,000 units/mL of the indicated Hu-IFN. Panels A and C show treatment with Hu-IFN-αA/D and panels B and D treatment with Hu-IFN-gamma. Fluorescence values shown are not linear but represent the fluorescence detection channels (of which there are 256) of the cytofluorograph. The real value of the x axis shown spans approximately three decades on the log scale.

FIG. 4 illustrates the integration/deletion plasmid and its use. The schematic diagram shows two-point recombination between the integration/deletion plasmid and YAC insert that results in internal deletions. Moreover, genes with known phenotypes contained within the YAC insert can be localized by expressing the deleted YACs in eukaryotic cells. DNA in the vicinity of the insertion can be rescued and identified, then used to isolate the corresponding cDNA clones. Disruption of gene structure and/or function can provide definitive relationships between the cDNA clones isolated and genes into which the integration/deletion plasmid has inserted.

Figure 5:
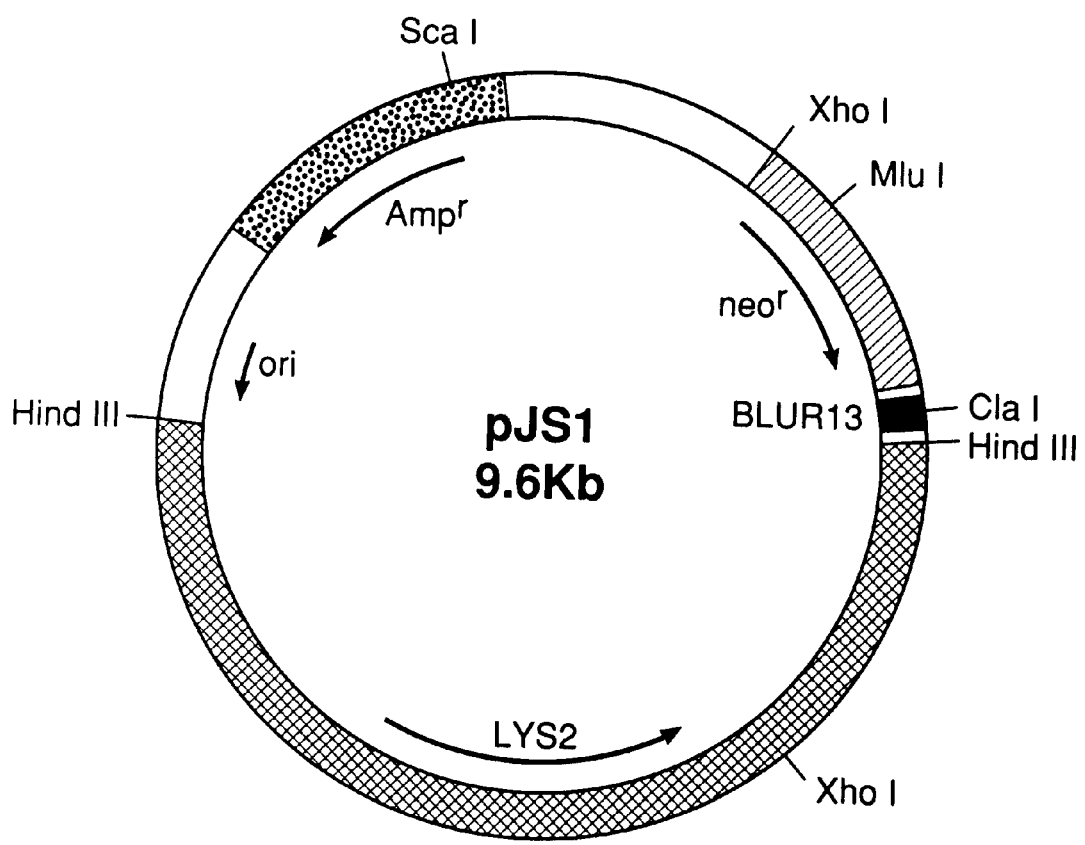
FIG. 5 illustrates a restriction map of the integration/deletion plasmid. The plasmid contains the antibiotic G418 resistance gene cassette under control of the thymidine kinase promoter and the LYS2 gene as a yeast selectable marker.

FIG. 5 illustrates a restriction map of the integration/deletion plasmid. The plasmid contains the antibiotic G418 resistance gene cassette under control of the thymidine kinase promoter and the LYS2 gene as a yeast selectable marker. The ClaI site introduced into the BLUR13 element was used to linearize the plasmid with Alu sequences at each end. This yielded linear DNA that provided a high frequency of recombination with the human-derived YAC insert.

Figure 6:
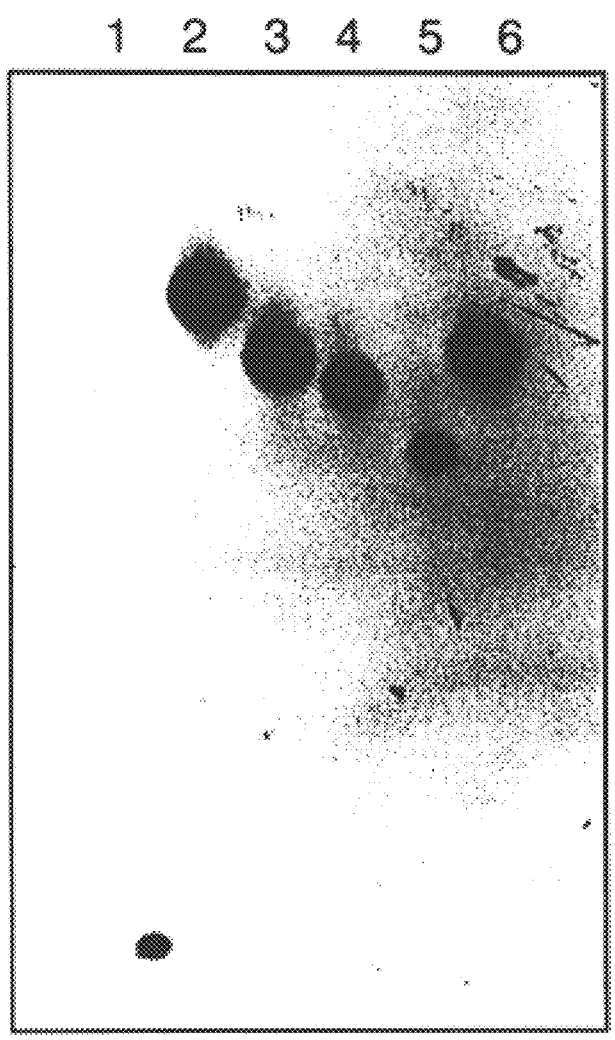
FIG. 6 illustrates a Southern blot of PFGE from the deleted YACs.

FIG. 6 illustrates a Southern blot of PFGE from the deleted YACs. Five Lys2+ transformants were chosen to prepare agarose plugs. The plugs were run on PFGE (0.5× TBE, 35 second pulse, 170 volts, 15° C.). The blot was probed with the radiolabeled neo gene to identify the chromosome into which the plasmid was integrated. GART D142H8.neo.23 (lane 1), neo.24 (lane 2), neo.25 (lane 3), neo.32 (lane 4), and neo.35 (lane 5).

FIG. 7 illustrates the localization of integrated plasmid in targeted YAC. A) A quarter of a plug was incubated with restriction endonuclease NotI as described in "Experimental Procedures" followed by pulsed-field gel electrophoresis (0.5×TBE, 35 second pulse, 170 volts, 15° C.). The Southern blot was hybridized with three probes separately: a) neo, b) centric vector arm (2.7 kb PvuII and BamHI cut of pBR322), and c) acentric vector arm (1.7 kb PvuII and BamHI cut of pBR322). GART D142H8.neo.1 (lane 1), neo.16 (lane 2), neo.17 (lane 3), neo.29 (lane 4), neo.122 (lane 5), and neo.125 (lane 6). B) Schematic diagram showing where the integrated plasmid is located in terms of the two NotI sites.

Figure 8:
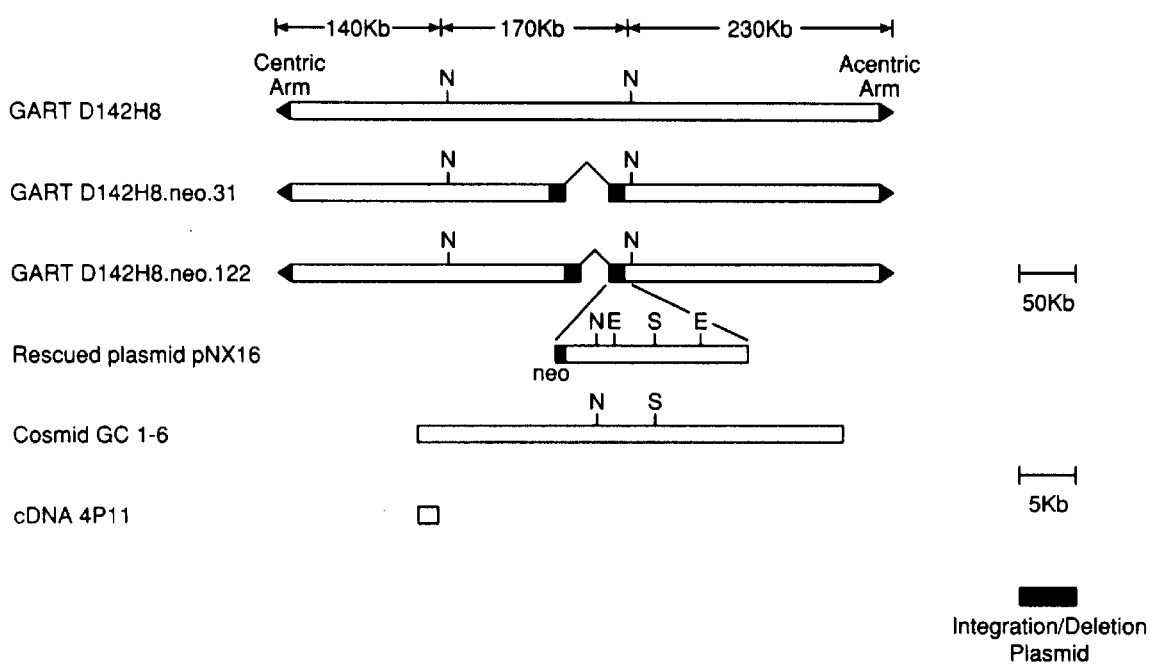
FIG. 8 illustrates the use of deleted YAC to identify specific genes and cDNA clones.

FIG. 8 illustrates the use of deleted YAC to identify specific genes and cDNA clones. The schematic diagram outlines how the specific gene or its cDNA can be isolated with the deleted YAC. YAC D142H8.neo.31 and neo.122 have 50 kb and 20 kb deletions, respectively, and share the targeted site which contains the neo gene. A 16 kb XhoI fragment containing the neo gene was rescued as described in "Experimental Procedures." The 600 bp HindIII fragment around the SalI site of the rescued DNA was used to isolate cosmid clone GC1-6. Then a 3 kb EcoRI-ClaI fragment from the cosmid insert was utilized to isolate the corresponding cDNA, 4p11. E: EcoRI, N: NotI, S: SalI.

FIG. 9 illustrates an agarose gel electrophoresis of DNA and Southern blot analysis. A) Yeast chromosomal DNAs from random internally-deleted YAC clones were cut with restriction endonuclease EcoRI, run on a 0.8% agarose gel, and blotted onto a nylon membrane. The blot was probed with the radiolabeled cDNA, 4p11, derived from the NotI site close to the acentric vector arm (FIG. 8). B) The blot was reprobed with the acentric vector arm. GART D142H8 (lane 1), GART D142H8.neo.1 (lane 2), neo.4 (lane 3), neo.5 (lane 4), neo.31 (lane 5), neo.35 (lane 6), neo.51 (lane 7), neo.83 (lane 8), neo.100 (lane 9), neo.104 (lane 10) and neo.122 (lane 11).

FIG. 10 illustrates a schematic map of fragmentation vectors pSE1 and pSE2, and the procedure used for fragmentation of the parental GARTD142H8.ura.2 YAC. TEL= telomere; CEN=centromere. Size of BamHI-BamHI fragment is 1.7 kb. The BamHI-EcoRI fragment containing the Alu sequence is 8.25 kb; the second BamHI-EcoRI fragment is 9.3 kb. The NotI and SacI sites are unique and may be used to rescue the right end of the YAC.

Figure 11:
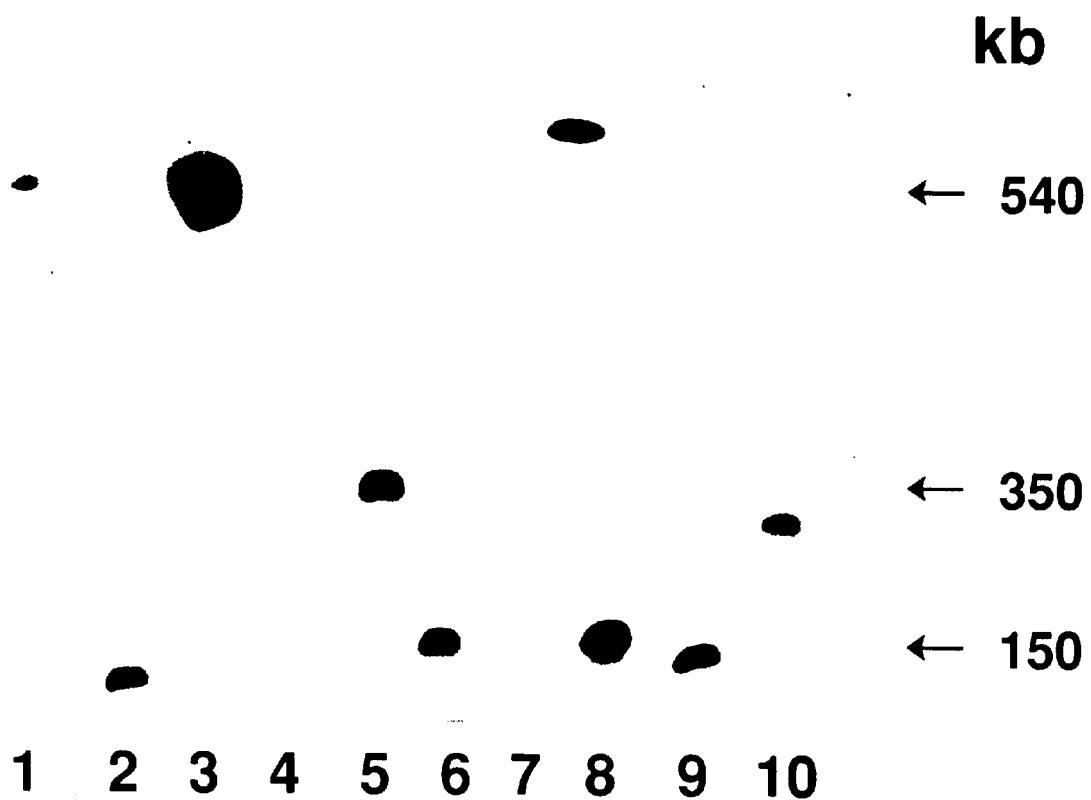
FIG. 11 shows a Southern blot of YACs to demonstrate the presence of the unique pGC8.10E6 sequence.

FIG. 11 shows a Southern blot of YACs to demonstrate the presence of the unique pGC8.10E6 sequence. YACs were analyzed by pulsed-field gel electrophoresis. After blotting to nitrocellulose, the filters were hybridized under standard conditions to either a $^{32}$P-labeled 3.0 kb EcoRI fragment of $^{32}$P-labeled pGC8. 10E6. The pGC8.10E6 contains 6.0 kb of unique DNA mapping to the leftmost end of GARTD142H8 and was provided by Dr. Robert Donnelly. Filters were washed under stringent conditions. Lane 1 is the B8 YAC. Lanes 2–10 show YACs obtained after fragmentation. YAC in lane 3 is the same approximate size as B8. Lane 7 illustrates one of the two YACs whose size increased. Variations in hybridization intensity reflect the amount of DNA loaded.

Figure 18:
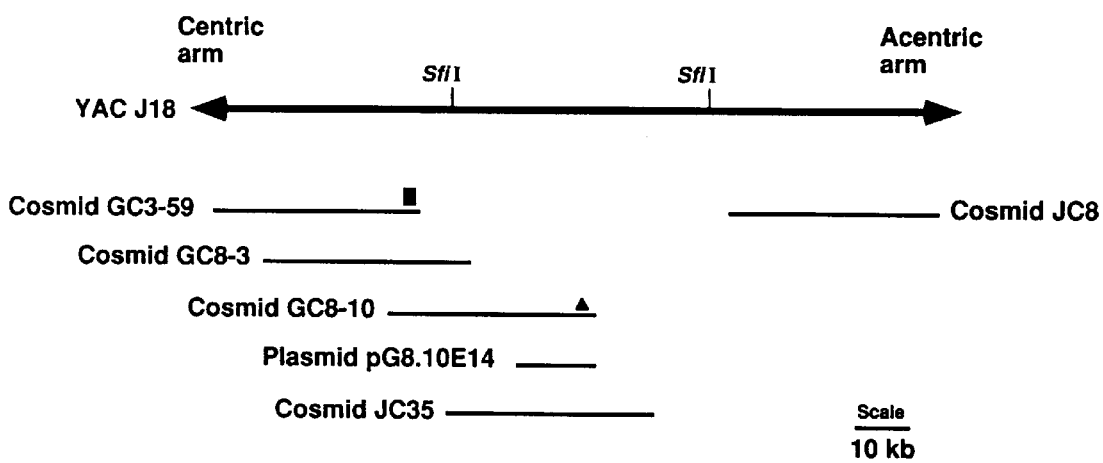
FIG. 18 illustrates YAC J18 and overlapping cosmids.

FIG. 18 YAC J18 and overlapping cosmids. Fragmented YAC J18 (150 kb) which encodes the accessory factor-1 (AF-1) for the Hu-IFN-gamma R was described (70,71). The cosmid libraries were made from the YACs GART D142H8 and J18 as described under "Experimental Procedures" and elsewhere (92). The cosmid libraries were screened with human Cot-1 DNA (BRL) as a probe. The Cot 1 positive cosmids were screened with the TRP1 and URA3 gene fragments to identify the cosmids corresponding to the YAC ends. The cosmid GC3-59 and JC8 were identified by hybridization to the TRPi and URA3 gene fragments, respectively. Thus, these cosmids corresponded to the respective ends of YAC J18. Gene walking procedures were then used to identify adjacent cosmids. The DNA fragment (/) without human repetitive sequence derived from one end of the GC3-59 cosmid was used to identify the overlapping cosmids GC8-3 and GC8-10. Similarly the terminal fragment (/) from cosmid GC8-10 was used to identify cosmid JC35. The 14 kb EcoRI subfragment from cosmid GC8-10 (pG8. 10E14) was used to identify the transcript from 3x1S polyA$^+$ mRNA.

Figure 19:
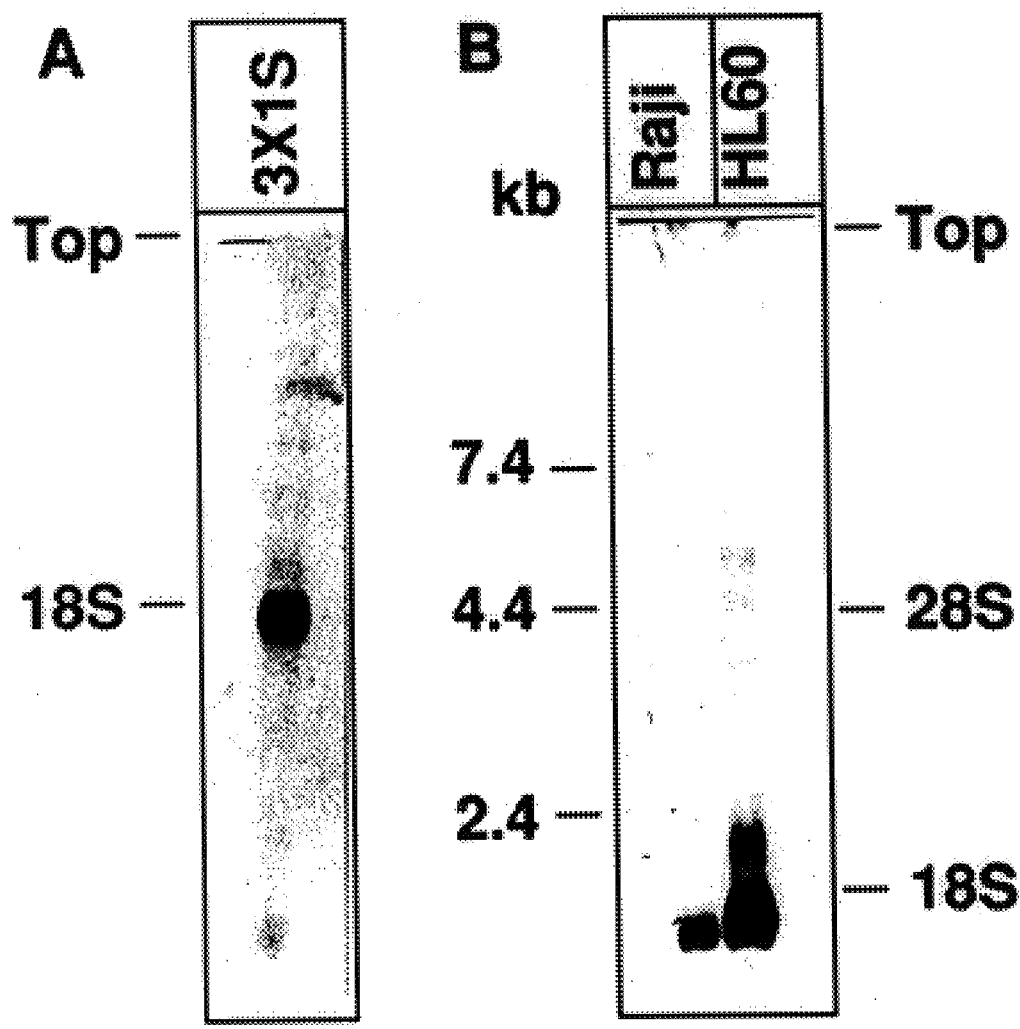
FIG. 19 shows a Northern blot analysis of RNA isolated from human Raji, HL60 and 3x1S cells.

FIG. 19. Northern blot analysis of RNA isolated from human Raji, HL60 and 3x1S cells. (A) Three micrograms of oligo(dT)-selected mRNA from 3x1S cells was fractionated on a 1.0% agarose gel containing 2.2 M formaldehyde and blotted onto a nylon membrane. The blot was hybridized with the 14 kb EcoRI fragment (pG8. 10E14) derived from cosmid GC8-10 preassociated to Cot 10 with sonicated human DNA. A single transcript of 1.8 kb was detected. (B) About one half microgram of oligo(dT)-selected mRNA from Raji and HL60 cells were processed as described above and probed with a 1.8 kb insert from plasmid pJS3. The same size of transcript (1.8 kb) from human cells was detected.

Figure 20:
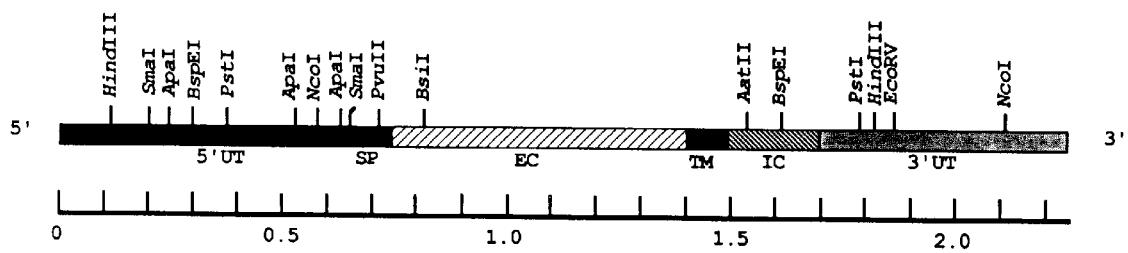
FIG. 20 is a schemiatic representation and restriction map of the human IFN-gamma Accessory Factor-1 (AF-1) cDNA clones pSK1 and pJS3.

FIG. 20. Schematic representation and restriction map of the human IFN-gamma Accessory Factor-1 (AF-1) cDNA clones pSK1 and pJS3. The dark stippled box indicates the location of the putative coding regions for the signal peptide (SP); the black dark crosshatched box, the transmembrane region (TM); the light stippled boxes, 3' and 5' untranslated regions (3'UT and 5'UT); the extracellular (EC) and intracellular (IC) domains as shown. The restriction endonuclease recognition sites are shown on the diagram.

FIG. 21. Human IFN-gamma accessory factor-1 (AF-1) cDNA (pSK1 and pJS3) nucleotide and predicted amino acid sequences.

FIG. 21A shows the sequence of the cDNA insert in plasmid pSK1. Hydrophobic putative leader and transmembrane regions are highlighted by rectangular boxes. Sites of putative asparagine-linked glycosylation are highlighted by heavy overlining of the amino acids involved. The molecular weight of the putative receptor polypeptide from amino acids 28–337 (310 residues) without consideration of post-translational modification is 35,034; from amino acids 1 to 337, the molecular weight is 37,834.

FIG. 21B shows the sequence of the cDNA insert in plasmid pJS3. Details are similar to those described for FIG. 15A. The amino acid sequence differs from that in pSK1 by a single amino acid substitution: Arg 64 (pSK1) Gln64 (pJS3).

Figure 22:
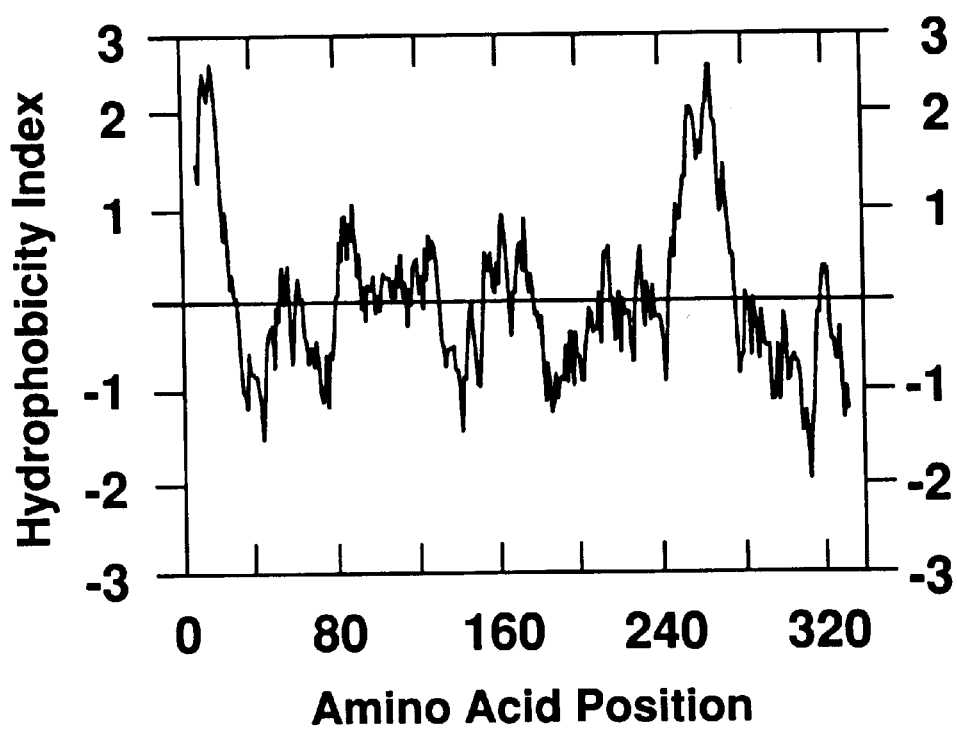
FIG. 22 is a hydropathy plot of the predicted human IFN-gamma accessory factor-1 amino acid sequence.

FIG. 22. Hydropathy plot of the predicted human IFN-gamma accessory factor-1 amino acid sequence. Positive values indicate increasing hydrophobicity. The hydropathic values represent an average obtained from 13 amino acids.

Figure 23:
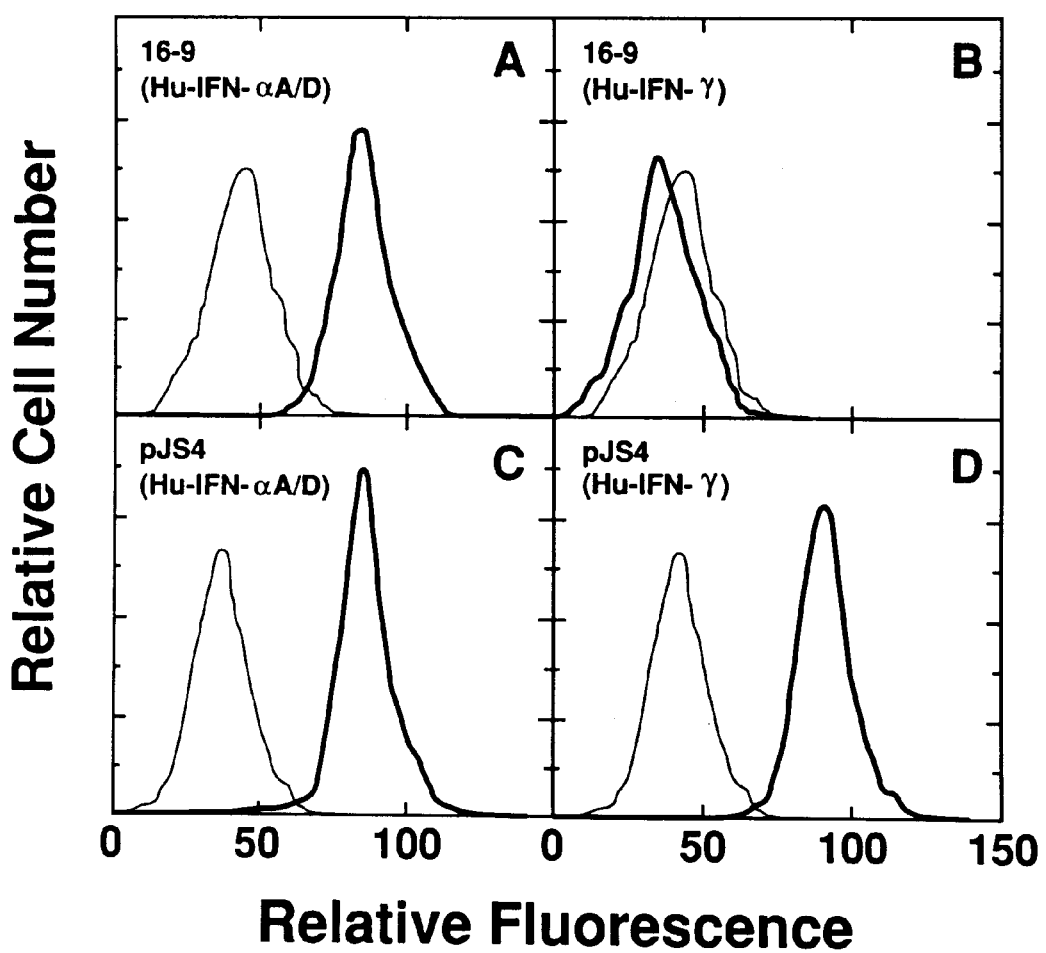
FIG. 23 shows the induction of HLA-B7 surface antigen.

FIG. 23. Induction of HLA-B7 surface antigen. A. The HLA-B7 antigen was detected by treatment of cells with mouse anti-HLA monoclonal antibody (W6/32) followed by treatment with FITC-conjugated anti-mouse IgG. The cells were analyzed by cytofluorography. Panels A and B represent 16-9 cells and panels C and D pools of 16-9 cells transfected with plasmid pJS3. The thin line indicates cells not treated with IFN and the heavy line indicates treatment with 1,000 units/mL of Hu-IFN-αA/D or 100 units/ml of Hu-IFN-gamma. Panels A and C show treatment with Hu-IFN-αA/D and panels B and D treatment with Hu-IFN-gamma. Fluorescence values shown are not linear but represent the fluorescence detection channels (of which there are 256) of the cytofluorogph. The real value of the x axis shown spans approximately three decades on the log scale. B. This represents the results with 16-9 cells transfected with plasmid pJS4 instead of pJS3, but otherwise the experiment was similar to that of part A.

C. This represents the results with 16-9 cells transfected with plasmid pSK1 instead of pJS3, but otherwise the experiment was similar to that of part A, panels C and D, except that 500 units/mL of Hu-IFN-gamma were used (Panel B). These experiments with plasmid pSK1 were performed with a population of transfected cells that were selected with a fluorescence-activated cell sorter for high class I MHC induction in response to Hu-IFN-gamma.

Figure 24:
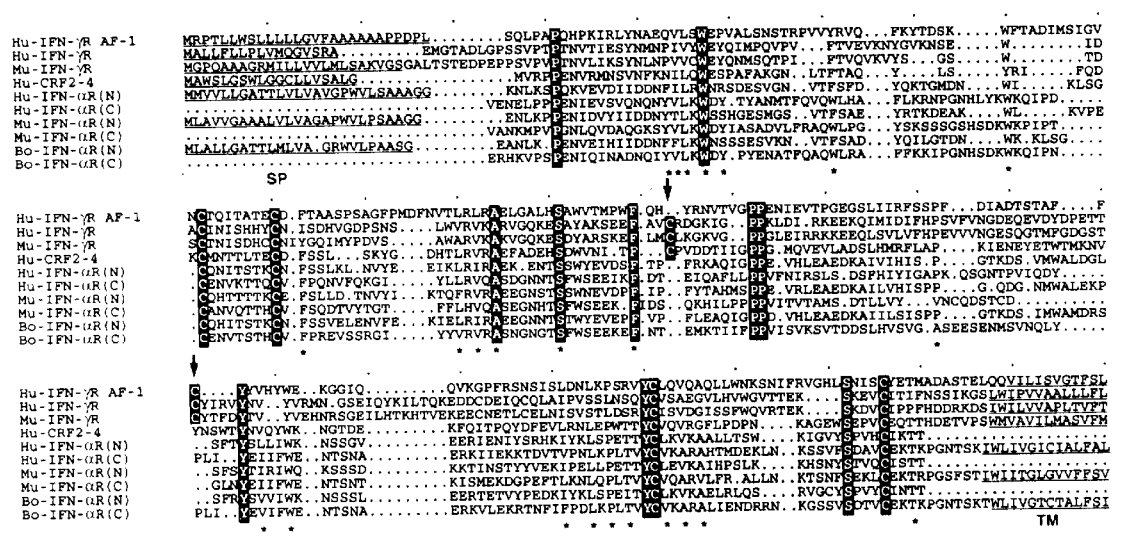

FIG. 24. Amino acid sequence alignment of human AF-1 and some members of the class 2 cytokine receptor family. Alignments were made by the algorithm of Needleman and Wunsch (78) with a gap weight of 5.0 and length weight of 0.3 for the parameters used in the computations. The single extracellular domains of the human AF-1, human (23) and mouse (24) IFN-gamma receptors, the human CRF2-4 (90) and the N- and C-terminal repeated domains of the human (87), mouse (86), and bovine (88,89) IFN-gamma receptors are aligned. The following are the abbreviations of the sequences aligned with the AF-1 protein (Hu-IFN-gamma R AF-1): Hu-IFN-gamma R (23), Mu-IFN-gamma R (24), CRF2-4 (90), Hu-IFN-αR(N) and Hu-IFN-αR(C) (87), Mu-IFN-αR(N) and Mu-IFN-αR(C) (86) and Bo-IFN-αR (N) and Bo-IFN-αR(C) (88,89). The αR(N) and αR(C) designate amino and carboxy terminal domains of the extracellular region, respectively. The highly conserved cysteines, prolines, charged and aromatic amino acids are boxed. The conserved aromatic and hydrophobic clusters are indicated by an asterisk. The putative signal peptide (SP) and transmembrane domains (TM) are underlined. The conserved cysteine residues in the AF-1, CRF2-4 and IFN-gamma Rs are indicated by an arrow over the box of the third alignment section; conserved cysteines in CRF2-4 and IFN-gamma Rs, but not AF-1 are indicated by an arrow over the box of the second alignment section.

FIG. 12. The accessory factor and interferon α/β receptor region of Chromosome 21q. The IFN-α/⊕ receptor gene and the CRF2-4 gene have been localized to one end of the IFN-α receptor YAC. The GART gene is located in the position indicated on the GART YAC. Dotted lines indicate region of possible overlap between the GART YAC and the IFN-α receptor YAC. The orientation of the GART YAC is known to be as shown, with the centromere to the left and the acentric end toward the telomere of Chromosome 21q. The orientation of the IFN-α receptor YAC relative to the GART YAC has not been determined; however, the centromere is to the left and proximal to the IFN-α receptor gene. A=AscI; B=BssH II; N=NotI; S=SfiI.

FIG. 13. Schematic illustration of YACs used to transform 16-9 cells. The phenotype of all the yeast strains containing the YACS shown is Ura+, Trp+, neo+. Hybridization to a probe ($^{32}$P-labelled by random priming) specific to the left (centric) end of the GART YAC (pGC8. 10E6) indicated that all YACs shown contained an intact centric end. Fusion of yeast containing YACs to 16-9 cells was performed as described under "Experimental Procedures." A '+' indicates that MHC class I induction with IFN-gamma was observed; '−' indicates no observed induction. Sizes of YACs were determined by pulsed-field gel electrophoresis (PFGE) with yeast DNA PFGE markers. Small circles represent telomeres; ovals indicate location of centromeres.

Figure 14:
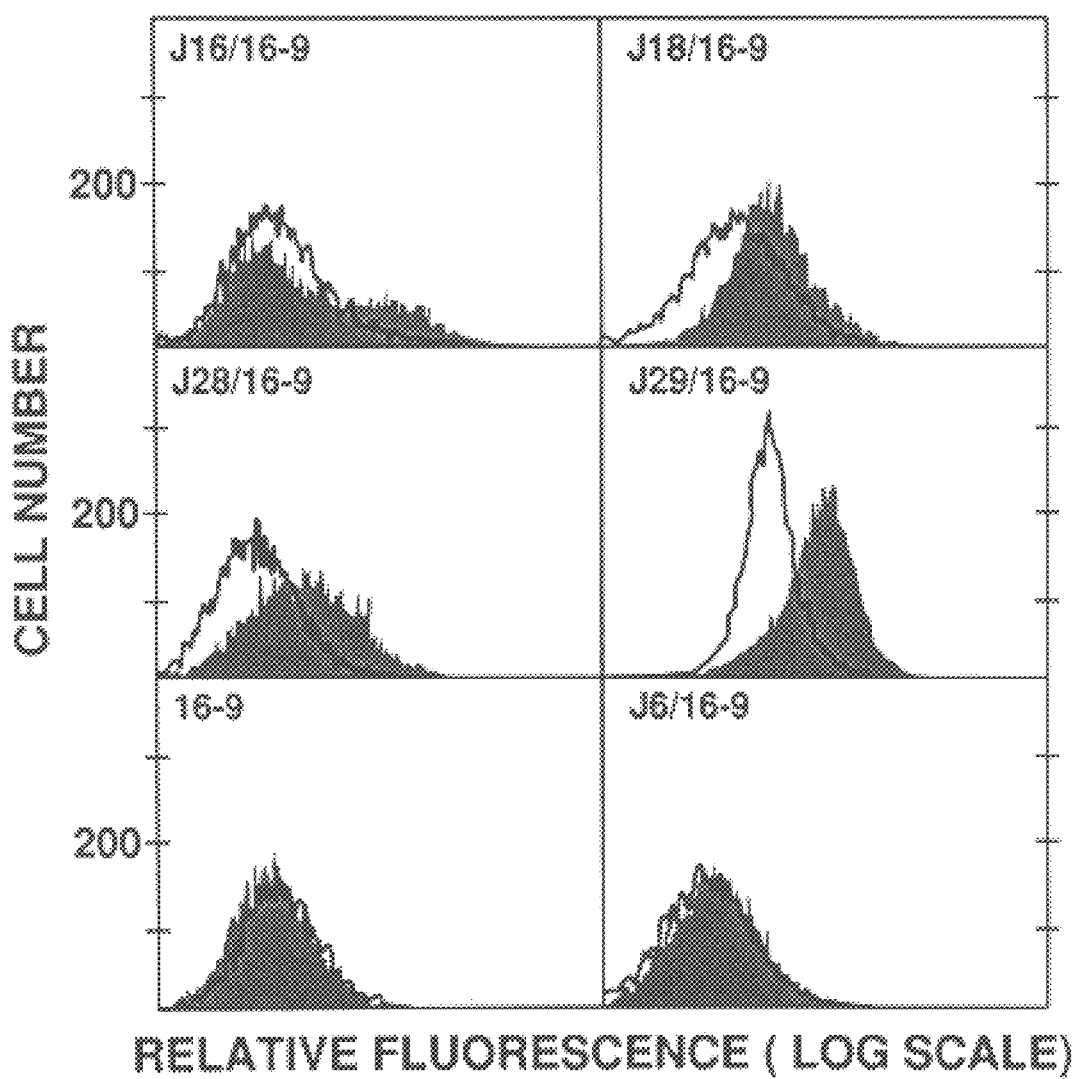
FIG. 14 is a cytofluorographic analysis of MHC class I induction in cells transformed by yeast containing Ura+ YACs.

FIG. 14. Cytofluorographic analysis of MHC class I induction in cells transformed by yeast containing Ura+ YACs. Hu-IFN-gamma was present at 125 units/ml for 48 hrs in all cases. Solid line, no interferon; stippled area, cells treated with Hu-IFN-gamma. Double peaks were observed in the J16/16-9 cell line. This phenomenon may be attributable to loss of the Hu-IFN-gamma R or the HLA-B7 gene. In the case of J29/16-9 cells, the original transformants also displayed two peaks but subsequent cloning produced the J29/16-9 cell line exhibiting a single peak after IFN-gamma induction.

Figure 15:
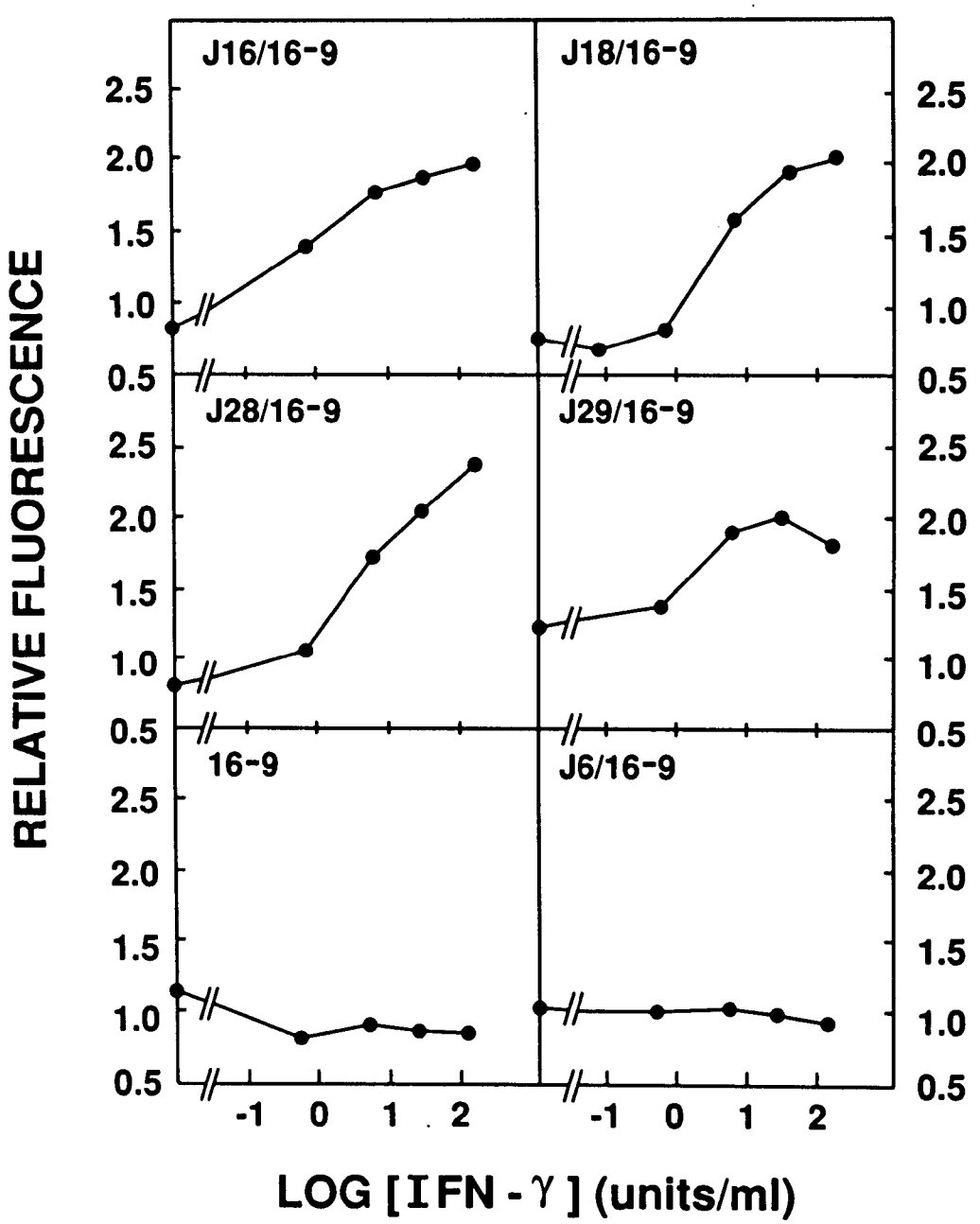
FIG. 15 shows the responsiveness of cell lines to various concentrations of Hu-IFN-gamma.

FIG. 15. Responsiveness of cell lines to various concentrations of Hu-IFN-gamma. Cells were incubated with or without Hu-IFN-gamma at the indicated concentrations for 48 hrs. In each section, points to the left are controls incubated without Hu-IFN-gamma. All fluorescence values are based upon the mean fluorescence of the cell population (N=10,000).

FIG. 16. Gel shift assay for ISGF3-gamma(A) and GAF (B) in selected cell lines. For ISGF3-gamma, cells were treated with IFN-gamma at 100 units/ml for 18 hours and then assayed for ISGF3-gamma as described under "Experimental Procedures" with an oligonucleotide corresponding to the ISRE (114). For GAF, cells were treated with IFN-gamma at 100 units/ml for 30 minutes and assayed as described ( ). C=control; /=IFN-gamma treated. GART refers to the cell line which was transformed by the parental GART YAC.

Figure 17:
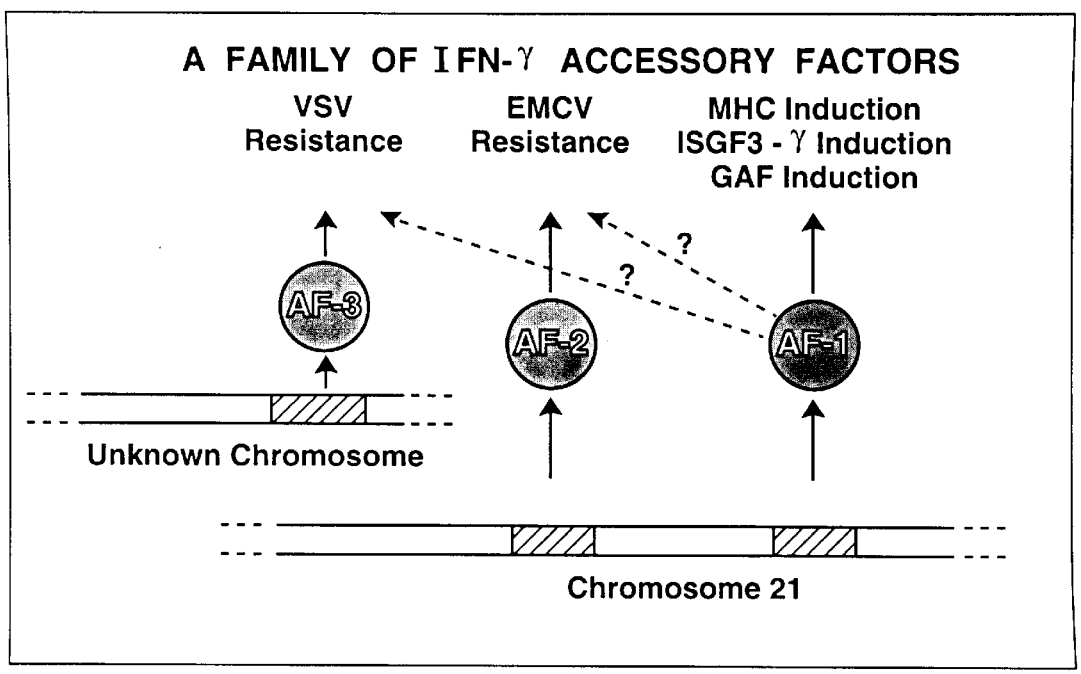
FIG. 17 is a diagrammatic representation of the location and interaction of the Hu-IFN-gamma receptor accessory factors located on Chromosome 21q and elsewhere.

FIG. 17. Diagrammatic representation of the location and interaction of the Hu-IFN-gamma receptor accessory factors located on Chromosome 21q and elsewhere. AF-1 refers to the Chromosome 21 accessory factor whose activity and location have been previously described (97,98,101,107, 117). AF-2 is an accessory factor which is also located on Chromosome 21q and which confers EMCV resistance to cells in response to Hu-IFN-gamma. AF-3 is an accessory factor which is required for VSV resistance (110) in response to Hu-IFN-gamma, but not located on Chromosome 21q. Dashed arrows indicate potential cooperative interactions between accessory factors.

RESULTS AND DISCUSSION

YAC Clone Encoding an Accessory Factor

3x1S Region YACs

The 3x1S somatic cell hybrid contains DNA that encodes one component of the human type I interferon receptor (22,43–45) as well as the accessory factors responsible for class I HLA antigen induction upon binding of Hu-IFN-gamma to its receptor (14,15,22,46). The segment of human Chromosome 21 in 3x1S cells is referred to as the 3x1S region, whose size is about 1–3 MBA depending on the estimation method (46; R. J. Donnelly, unpublished data). In order to identify the gene(s) for accessory factor(s) for the Hu-IFN-gamma receptor system, Jung (46) prepared a cosmid library from 3x1S DNA and screened the library with labeled total human DNA so that cosmid clones containing highly repetitive human sequences (Alu, Kpn etc.) could be selected. More than 200 cosmid clones were isolated which theoretically covered the 3x1S region 2 to 6 times. The resultant cosmids were transfected into CHO cells which had been stably transfected with both the HLA-B7 gene and Hu-IFN-gamma receptor cDNA in an attempt to reconstitute a biologically active Hu-IFN-gamma receptor system capable of inducing human class I HLA antigen expression. This approach was not successful, possibly because this region may contain several genes necessary for activity which cannot be cloned into a single cosmid, the gene is too large to be accommodated in a single cosmid vector, or there was a bias during screening with human repetitive DNA so that the particular region of DNA was not represented in the cosmid clones positive for human DNA. For these reasons, YAC clones were chosen to carry out a similar experiment to that described above since YAC clones can maintain more than 1 MBA of DNA as an exogenous fragment (27,47). Through the Chromosome 21 Joint YAC Screening Effort, 10 YAC clones were obtained screened with various primer pairs derived from six different loci which are scattered in the vicinity of the 3x1S region. As shown in FIG. 1 and Table I, there were four YAC clones [525 B119G7 (1200 kb), 525 A165D7 (210 kb), 525 C4C10 (220 kb), and 525 C14B2 (450 kb)] derived from the D21S65 locus; one YAC clone [H8(517) A222A12 (220 kb)] from the D21S17 locus; one YAC clone [GART D142H8 (540 kb)] from the D21PFGS locus; two YAC clones [518 A234B10 (210 kb) and 518 B134B9 (225 kb)] from the D21S55 locus; one YAC clone [SOD D112A5 (180 kb, 120 kb)] from the 1)21SOD1 locus; and one YAC clone [IFNAR B49FI (150 kb)] from the D21IFNAR locus (Table I). The SOD, D21S58, GART, D21S65, H8, and IFNAR loci were known to be in the 3x1S region (22). Although the D21S55 locus was not in the 3x1S region, it was close enough to the 3x1S region to be tested. The YAC derived from the D21S58 locus was not available in time to be included in this study. The 525 B119G7 YAC and IFNAR B49F1 YAC are chimeric YACs which have non-contiguous human DNA fragments (Dr. David Patterson, personal communication). The SOD D112A5 YAC clone contains two different YACs, yet it is not known which one is the SOD YAC. Until it is known how the clones overlap, it is difficult to estimate how much of the 3x1S region is covered by these YAC clones. However, if it is assumed that there is no overlap between the YACs from different loci, except the chimeric 525 B119G7 and IFNAR B49FI YACs, then 5 different YAC clones (525 C14B2, 517 A222A12, GART D142H8, 518 B134B9, SOD D112A5) may cover about 1.5 mb of the 3x1S region, which represents at least 50% of the region.

Integration of the Neo$^r$ Gene into YACs

In order to test the function of these YACs, the neo$^r$ gene was introduced into the YACs by targeting homologous recombination to Alu repeat sequences. A similar procedure was described (33) for *S. cerevisiae* YPH252. Since all of the 3x1S region YACs were derived from *S. cerevisiae*

AB1380 which has a genotype different from that of *S. cerevisiae* YPH252, a new integrating plasmid, pJS1, containing a modified human Alu family member BLUR13/ClaI, the yeast LYS2 gene, and the neo$^r$ gene was designed as described under "Experimental Procedures." Digestion of pJS1 with ClaI produces a linear 10 Kb molecule with two free ends homologous to Alu sequences. The ClaI-linearized plasmid should then target integration to Alu sequences on the YAC by homologous recombination. This event introduces the Lys2 gene (and neo$^r$ gene) into the YAC clones so that Lys2$^+$ transformants can be selected on yeast minimal medium lacking lysine. Twenty Lys2$^+$ transformants were selected from each of ten different YAC clones transformed with integrating plasmid pJS1. To check for integration of the neo$^r$ gene into yeast DNA, each of the twenty Lys2$^+$ transformants was screened by colony hybridization with the neo$^r$ gene as a probe (data not shown). The frequency of a neo$^r$ gene in the Lys2$^+$ transformants varied from 5% to 80%. It seems that in some cases only the LYS2 gene was selectively integrated during recombination. To confirm that the neo$^r$ gene was integrated into the YAC rather than the endogenous yeast chromosomes, two neo$^r$ positive clones from each YAC were selected for analysis by PFGE and hybridization with probes for the neo$^r$ gene (FIG. 2A). About 76% of the neo$^r$-positive clones were targeted to the YAC rather than yeast chromosome II which contains a mutated LYS2 gene (data not shown). Since the LYS2 gene in *S. cerevisiae* AB1380 is almost intact, it is possible that the LYS2 gene in the integrating plasmid was targeted to the endogenous yeast LYS2 sequence in some cases. It is also worth noting that the GART D142H8.neo.18 clone turned out to have a smaller YAC than the original one (FIG. 2A). In this case, it is possible that two distant Alu sequences were targeted and the internal DNA fragments between them were lost during recombination (48). To test whether the neo$^r$ gene cassette is integrated into the YAC intact, total yeast chromosomal DNA from targeted YAC clones were digested with BamHI and XhoI and the blot was probed with labeled neo$^r$ gene. As shown in FIG. 2B, 1.1 kb fragments corresponding to the neo$^r$ gene were apparent indicating that the neo$^r$ gene was targeted without disruption of the coding sequence. In some cases (one out of five), DNA fragments of a different size were detected.

Fusion and Cytofluorographic Analysis

Spheroplasts from the neo$^r$ gene-containing YAC clones were fused to 16-9 cells. After selection with G418 for two weeks, resistant colonies were obtained from several of the YACs (Table 1). Not all fusions generated G418 resistant colonies possibly due to disruption of the neo$^r$ gene during the targeting process. Colonies from the individual fusions were pooled and analyzed for IFN-dependent class I HLA antigen induction by cytofluorography. The parental 16-9 cells displayed very good class I HLA induction upon treatment with Hu-IFN-αA/D (FIG. 3, Panel A) and a slight reduction in HLA expression in response to 1,000 units/mL Hu-IFN-gamma (FIG. 3, Panel B). The 16-9 cells transformed by fusion with GART D142H8.neo.18 (henceforth called YAC-JS2) also exhibited a good response to Hu-IFN-αA/D (FIG. 3, Panel C). In addition, they also showed good HLA induction upon treatment with 1,000 units/mL Hu-IFN-gamma (FIG. 3, Panel D). Treatment of these transformed 16-9 cells with 200 units/mL of Hu-IFN-gamma also gave a response similar to that for treatment with 1,000 units/mL (data not shown). The results shown in FIG. 3 with 16-9 cells fused to YAC-JS2 were performed on several occasions with pools of clones and with individual clones and gave similar results. It is interesting to note that a colony derived from the GART 142H8.neo. 16 YAC was negative for HLA induction by Hu-IFN-gamma. This YAC clone may have a deletion of approximately 10 kb since the apparent YAC size is similar to the original GART YAC even after the integration of the 10 kb plasmid (FIG. 2A, lane 2). It is difficult to conclude definitively that the negative response resulted from the deletion of a portion of the gene(s) which encodes the Hu-IFN-gamma accessory factor(s) because only one colony, which may not have incorporated the entire YAC (31), was assayed. However, if a sufficient number of neo$^r$-positive YACs are screened which do not respond to Hu-IFN-gamma, it may be possible to identify the gene(s) disrupted during integration of the pJS1 plasmid.

Antiviral Activity of 16-9 Cells Transformed with YAC-JS2

It was reported that hamster/human somatic hybrid 153B7-8 cells (carrying chromosome 21q as its sole human chromosome) transfected with the Hu-IFN-gamma receptor cDNA are protected against EMCV infection and display an increase in class I HLA antigen expression upon treatment with Hu-IFN-gamma (20,25). Furthermore, since the 3x1S region of Chromosome 21q is sufficient to complement the Hu-IFN-gamma receptor for class I HLA induction (22,46), we tested whether this region also encodes the accessory factor which confers protection against EMCV infection in response to Hu-IFN-gamma. The results indicate that the 3x1S region of chromosome 21 q encodes the accessory factors for EMCV antiviral protection (Table 2). However, 16-9 cells transformed with YAC-JS2 (expressing the accessory factors for class I HLA antigen induction) do not show any protection against EMCV. This indicates that there are at least two accessory factors on human Chromosome 21q: one is required for induction of MHC class I antigens and a second is required for protection against EMCV.

Although expression of proteins has been demonstrated with YACs containing known genes (30–32), this is the first study which demonstrates a specific biological function from an undefined gene in a YAC expressed in eukaryotic cells. In order to introduce the G418 antibiotic resistance gene into the YACs used in this study, a new integrating plasmid (pJS1) was constructed for *S. cerevisiae* strain AB1380 which has been widely used for construction of YAC libraries. In conjunction with yeast and eukaryotic cell-fusion techniques, the integrating plasmid was used to introduce the neo$^r$ gene into the YACs so that the functional activity of the YACs could be determined. Furthermore, the integrating plasmid can also be used to localize the region of the YAC responsible for functional activity through its ability to produce insertional inactivation of genes and deletions. Recombination with plasmid pJS1 can produce deletions of various size within a YAC. We have observed deletions of up to 350 kb in the case of the GART D142H8 YAC (49).

This study demonstrated that the Chromosome 21 accessory factor gene necessary for class I HLA antigen induction by Hu-IFN-gamma is located in the 540 kb of human DNA in the GART D142H8 YAC. This observation is consistent with data which indicated that the gene for the accessory factor is located in the distal portion of band 21q22.1, near the markers D21S58 and GART (21,45).

We previously demonstrated that the accessory factors required for VSV protection are different from those leading to EMCV protection after Hu-IFN-gamma treatment (20).

The observation that a small segment of human chromosome 21q (3x1S region) was sufficient to induce class I HLA antigen expression and EMCV protection with Hu-IFN-gamma suggested that the same accessory factor was involved in both activities (20). However, the observation that 16-9 cells transformed with YAC-JS2 were not protected against EMCV challenge is evidence that another accessory factor is necessary for this antiviral activity, or that both the antiviral factor and the class I MHC induction factor are required for this antiviral activity. Thus our data indicate that the distinct additional factor responsible for the EMCV antiviral effect present in the 3x1S region is not included in the GART D142H8 YAC. One might argue that the factor for antiviral activity is in the GART D142H8 YAC but the gene was disrupted due to targeting of the integration plasmid. However, because two separate pools of 16-9 cells fused with different $neo^r$-gene targeted YACs (GARTD142H8.neo.3; and YAC-JS2; Table 1) showed MHC class I induction but no protection against EMCV when treated with Hu-IFN-gamma, the argument for disruption of the same gene is less convincing.

The identification of a YAC which encodes the species-specific accessory factor for class I HLA induction by Hu-IFN-gamma should eventually lead to identification of the cDNA for the protein. This information will help us to understand the interactions between the Hu-IFN-gamma receptor and the accessory factors. In order to locate the genes and to find cDNAs for the accessory factors, various approaches such as YAC fragmentation (49), exon-trapping (50), hybrid selection of cDNA with the YAC (51), and direct screening of the cDNA library with the YAC (52) can be carried out. We have mapped the GART D142H8 YAC with some restriction endonucleases (NotI and AscI). The mapping data suggest that the GART D142H8 YAC is similar to yGART2 (600 kb) described by Girke et al. (32) since both YACs have two NotI sites and the GART gene is located between two NotI sites (170 Kb). Our results are consistent with and extend the results of Chumekov et al. (53) who reported a physical map of human Chromosome 21 constructed with the use of overlapping YACs. Our current efforts are directed at defining the specific gene or genes on the GART D142H8.neo.18 YAC that contribute the Chromosome 21 accessory function required for activity of the human IFN-gamma receptor. This study and our previous studies (20,46) demonstrate that accessory factor functions for class I MHC induction, protection of cells against EMCV infection and protection against VSV infection are mediated by different factors or a different combination of factors. We thus conclude that a family of accessory factors that mediate unique intracellular signals is associated with the IFN-gamma receptor. It is likely that these factors are qualitatively and quantitatively different in various tissues, a hypothesis that explains the individual responses of different cells and tissues to IFN-gamma.

Alu-targeting YAC Deletion Plasmids

Integration/Deletion Plasmid Construction

The parental plasmid for construction of the integration/deletion plasmid was pMClneo polyA which has an antibiotic G418 resistance gene cassette. The EcoRI site in the BLUR13 fragment from the pBP47 integrating plasmid (33) was modified to a ClaI site so that the integration/deletion plasmid could be linearized with ClaIresulting in an Alu sequence at both ends. The LYS2 gene was used in the integration/deletion plasmid to introduce a selectable marker into yeast after transformation. The ADE2 gene had previously been utilized to create an integrating plasmid with a selectable marker (34). However, a single copy of the ADE2 gene was not sufficient to confer adenine prototropy so that about 20 copies of the plasmid were necessary for selection. A partial restriction map of the integration/deletion plasmid pJS1 is shown in FIG. 5. The plasmid pJS1 was transfected into NIH3T3 cells and antibiotic G418-resistant colonies appeared after 14 days of selection. This confirmed the presence of a functional $neo^r$ gene.

Two-point recombination of the pJS1 plasmid into the YAC insert can delete the DNA between two separate Alu integration sites. Since Alu family sequences are known to be distributed at an average of 2 to 10 kb apart (61), deletions of various sizes at random positions can be introduced into the YAC insert as well as simple integration into single Alu sequences (FIG. 4).

Transformation of Yeast and Integration of Plasmid into the YAC Because linear DNA provides greater recombinogenic activity in yeast than circular DNA, plasmid pJS1 was linearized with ClaI restriction endonuclease and then introduced into GART YAC D142H8 via a PEG-mediated transformation procedure. Twenty $Lys2^+$ transformants were analyzed by colony hybridization with the neo gene as a probe to determine if this gene was integrated into the YAC clones. Sixteen clones out of the twenty $Lys2^+$ transformants showed the presence of a neo gene fragment (data not shown). The frequency of introducing the neo gene into the YAC clones along with the LYS2 gene (16/20) is higher than the results of Pachinis et al. (34) where only 1 out of 10 $Ade^+$ transformants was shown to have a neo gene. However, we found that the frequency varies from clone to clone. Neo-negative, $Lys2^+$ transformants might result from the loss of the neo fragment during recombination and/or from reversion of the chromosomal $Lys2^-$ to $Lys2^+$.

Internally-Deleted YACs

One hundred twenty-eight $Lys2^+$ transformants were analyzed to determine the size of the deletion in the YAC. While fifteen clones of one hundred twenty-eight (about 11%) were shown to have the plasmid integrated into yeast chromosome III which contains the endogenous LYS2 gene, sixty clones of the $Lys2^+$ transformants (about 47%) showed the presence of the neo gene in the YAC when analyzed by Southern hybridization of PFGE gels probed with a radiolabeled neo gene fragment. As shown in FIG. 6, YACs D142H8.neo23, neo.24 and neo.25 have less than 20 kb deletions, and YAC D142H8.neo.32 and neo.35 have a deletion of about 350 kb and 50 kb, respectively. The size of the deletion in sixty neo targeted YACs was determined (Table 3). The high number of clones having deletions of 0 to 20 kb (38 out of 60) suggests that the Alu sequences at the ends of the integration/deletion plasmid may have topological constraints which limit the targeted sequences to two relatively close Alu sequences in the YAC insert.

In order to determine where the recombination occurred, agarose plugs were made from six clones, and the DNAs were cut with endonuclease NotI and analyzed by Southern hybridization with a neo gene probe or probes derived from the centric or acentric YAC vector arms. As shown in FIG. 7, YAC D142H8.neo.1 was shown to contain the integration/deletion plasmid in a 230 kb NotI fragment close to the acentric vector arm since both the neo and the acentric probe hybridized to the same 230 kb fragment, while the centric probe hybridized to 140 kb NotI fragment close to the centric vector arm. The centric vector arm probe hybridized to the 230 kb right NotI fragment which contains the integration/deletion plasmid as well as the 140 kb NotI fragment because the targeting plasmid has part of the centric vector sequences (ampicillin resistance gene). YACs D142H8.neo.16, neo.29, neo.122, and neo.125 were targeted to the middle 170 kb NotI fragment and YAC D142H8.neo.17 to the 140 kb NotI fragment close to the centric vector arm (FIG. 7B). These data suggest that integrations and deletions occurred into Alu sequences throughout the YAC. A few clones were found to have two YACs, one with an integrated plasmid and one without. In those cases, the integrated YAC has a deletion and is positive for the neo gene.

Fusion of Yeast Spheroplasts to Mammalian Cells

Since the integration/deletion plasmid introduces the antibiotic G418-resistance selectable marker into the YAC, the functional activity of the deleted YAC can be tested following fusion to appropriate mammalian cells (30,32,31). However, when two-point targeting deletes part of the gene, eliminating its functional activity by disrupting the gene, eukaryotic cells with a negative phenotype will be obtained. Based on the location of the deletions in the YAC clones which have lost a functional activity, the specific gene can be precisely located (FIG. 4). Since recipient cells do not take up all of the YAC DNA after spheroplast fusion (32), it is important to assay several antibiotic G418-resistant colonies in order to ascertain that the negative phenotype was derived from a deletion or insertion, not from integration of only a portion of the YAC DNA into the eukaryotic genome. The fusion efficiency ranged from $3 \times 10^{-5}$ to $1 \times 10^{-6}$ (G418 resistant colonies/input cells). In some cases, no G418 resistant colonies appeared partly because the $neo^r$ gene was disrupted during the integration process.

Isolation of DNA Fragments Adjacent to the Integration Sites

After identifying the deleted YAC clones which exhibit a lack of functional activity, localization of the inactivated gene can be carried out by rescuing the DNA fragment adjacent to the targeted site. Before rescuing the DNA fragments it should be determined whether or not a single plasmid was integrated into the YAC. If more than one copy of the plasmid was integrated, it would not be possible to assign the site responsible for functional inactivation unambiguously.

Chromosomal DNA from YAC D142H8.neo.122 was digested with restriction endonuclease XhoI, separated on a 0.8% agarose gel, transferred to a nylon membrane, and probed with a radiolabeled neo gene fragment. One band at approximately 16 kb hybridized to the probe indicating that only one plasmid was integrated. The 16 kb XhoI fragment containing the integration sites was isolated from a plasmid library constructed with DNA from YAC D142H8.neo.122 DNA with a neo gene as the probe. The map of the 16 kb rescued plasmid (pNX16) is shown in FIG. 8. The insert DNA contains part of the neo gene and human DNA sequences derived from the vicinity of the NotI site close to the acentric vector arm. We also found that YAC D142H8.neo.31 has the same 16 kb XhoI fragment hybridizing to the neo gene (data not shown), suggesting that one of the two targeted Alu sites in these two deleted YAC clones occurred at about the same position. The other targeted Alu site of these YAC clones must be different because YAC D142H8.neo.122 and neo.31 have a 20 kb and a 50 kb deletion, respectively (FIG. 8).

In order to isolate a large intact piece of DNA encompassing the targeted site, a HindIII fragment (0.6 kb; free of human repetitive DNA) from the 16 kb rescued DNA was used to screen a cosmid library made from the original GART D142H8 YAC clone. A cosmid clone, GC1-6, was isolated. A 3 kb EcoRI-ClaI fragment from the insert of cosmid GC1-6 which is free of human repetitive sequences was used in turn to screen a cDNA library made from 3x1S human/hamster irradiation reduced hybrid cells (22). A cDNA clone, 4p11, was obtained (1.5 kb in size). Thus the rescued plasmid was used to locate the gene and isolate its cDNA (FIG. 8). Northern hybridization showed that the mRNA corresponding to the cDNA 4p11 is expressed in 3x1S cells (data not shown).

Disruption of a Gene by Deletion

In order to confirm that the random deletion event causes a deletion of the specific gene, ten deleted YACs were selected randomly for analysis of disruption of the gene. A Southern blot made from EcoRI-digested yeast DNAs was probed with cDNA 4p11 (FIG. 9). The intact gene hybridizing to the cDNA contains seven EcoRI fragments (FIG. 9, lane 1). However, YACs D142H8.neo.5 (lane 4), neo.31 (lane 5), neo.51 (lane 7), and neo.122 (lane 11) exhibited smaller fragments than the original 14 Kb EcoRI fragment. YAC D142H8.neo.35 (lane 6) is missing all seven EcoRI fragments. Although YAC D142H8.neo.83 (lane 8) has a 350 kb deletion, the gene corresponding to the cDNA 4p11 appears to be intact since all seven EcoRI fragments are present.

In this report we describe the construction of an integration/deletion plasmid for introduction of the antibiotic G418-resistance gene cassette into YAC inserts while at the same time producing deletions of various sizes during the insertion process. The $neo^r$ gene in the YAC is necessary to select mammalian cells with YACs integrated into the nuclear DNA following fusion between yeast and mammalian cells. The integrating plasmid previously described (34) for S. cerevisiae AB1380 does not have the versatility of our approach because it requires a specific DNA fragment derived from the YAC insert to be used as the targeting sequence, and about 20 copies of the plasmid must be integrated in order to convert the yeast cells from Ade⁻ to Ade⁺.

The GART YAC D142H8 used here is similar to the yGART2 clone described (32; 600 kb YAC) since both clones have two NotI sites yielding a 170 kb NotI fragment that encompasses the GART gene.

YAC clones screened from the YAC libraries constructed in S. cerevisiae AB1380 have been used to prepare contigs of this region (53). The plasmid described here can facilitate the characterization of the YACs and the identification of the genes on the basis of their function; and can provide another genetic approach for manipulating and modifying the YAC insert in addition to the integration and fragmentation procedures described previously since it produces random internal deletions of various size.

Furthermore, in this study we used a model system to develop a method for locating a functional segment within a YAC by gene disruption and isolating its cDNA. The cDNA, 4p11, isolated with the DNA fragment adjacent to the targeted site (neo side of the targeted site from YAC D142H8.neo.122 or neo.31) was used to demonstrate the disruption of its gene structure based on the disappearance of the 14 kb EcoRI fragment. The combination of structural analysis (DNA mapping) with functional activity provides definitive procedures to locate genes on YACs and to isolate the cDNAs involved.

Yeast Artificial Chromosome Fragmentation Vectors

Of the 27 Ura$^+$ clones analyzed 21 were found to contain fragmented YACs of molecular sizes ranging from 80 to 500 Kb (Table 4). Two of the YACs were of higher molecular size than the parental YAC (540 kb) and one YAC was approximately equal to 540 kb) in size Three Ura$^+$ clones did not contain any discernable YAC, either because of very small YAC size, low copy number, or gene conversion. As is shown in Table 4, the fragmented YACs were mostly 80 to 150 kb in size, but larger YACs were produced as well. To characterize further the YACs produced by this procedure, a 6 kb EcoRI fragment subcloned in plasmid pGC8.10E6 was used as a probe to blot the fragmented YACs. These results indicate that a high percentage (89%) of fragmented YACs contain this segment (Table 4, FIG. 11). Since pGC8.10E6 maps to the leftmost 50 kb of the B8 YAC, fragmentation must have occurred from the right end. (Deletion from the left end of the YAC would also be expected to produce acentromeric, Trp$^-$cells.) Nine of 10 yeast strains containing fragmented neo$^+$ YACs were fused to CHO cells and produced G418-resistant cell lines.

The fragmented YACs produced by this procedure have been mapped with restriction enzymes and have been used to align cosmid clones covering this region of Chromosome 21. The frequency of fragmentation obtained by this procedure is significantly higher than that originally reported (48) and is comparable to the high-efficiency YAC fragmentation vectors more recently described (60,58). Although selection of Ura$^-$ mutants is a precondition for use of these vectors, it is anticipated that the Ura3$^+$ selection procedure will be useful in that it is applicable to both AB1380 and YPH252 yeast strains. In addition, incorporation of a neomycin resistance gene into the fragmented Ura3$^+$ YACs will enable the localization of functional genes on the parental YAC after fusion of yeast spheroplasts to appropriate mammalian cells.

Localization of the Human Interferon-gamma Receptor Accessory Factor Gene

Gene Mapping

Using hamster×human somatic cell hybrids, we determined that accessory factor activity is located on human Chromosome 21q (97,98) and on mouse Chromosome 16 (100). Further cytogenetic evidence indicates that the Chromosome 21 accessory factor gene resides within the 1–3 Mb of Chromosome 21q which is contained in the 3x1S somatic cell hybrid (104,117). In addition, the Chromosome 21 accessory factor gene co-segregates with the IFN-α/β receptor gene and is also located near the GART gene (104,105). These relationships are diagrammed in FIG. 19. To map more precisely the location of the human Chromosome 21 accessory factor gene, we obtained a series of YACs specific to Chromosome 21 into which we introduced a neomycin resistance gene in order to determine their biological activity by fusion to mammalian cells (105). These experiments indicated that the gene encoding the Chromosome 21 accessory factor activity is located within a 540 kb YAC which also encodes the GART gene and whose address is D142H8. A second YAC, which is 160 kb in length and may partially overlap the GART YAC (FIG. 12), encodes a human IFN-α/β receptor gene (118) and is located at address B49F1 (105).

Although the GART YAC is known to the oriented as shown in FIG. 12, the orientation of the IFN-α receptor YAC has not been established. In addition, the overlap (if any) between the IFN-α receptor YAC and the GART YAC (dotted lines, FIG. 19) has not been defined. To date, no IFN-α receptor probe has hybridized to the GART YAC (R. Donnelly, J. Soh, S. Pestka, unpublished results). This may indicate that the IFN-α receptor YAC is oriented as shown in FIG. 19, or that the IFN-α receptor gene is proximal to the GART YAC but there is a gap between these two YACs. If there is such a gap, it is likely to be less than 50 kb in size. Based on digests of human DNA Cheng et al. (119) have shown that the IFN-gamma receptor gene, the CRF2-4 gene (120) and the GART genes are all contained within a 400 kb MluI restriction endonuclease fragment. These data are consistent with our map shown in FIG. 19. The 3' end of the GART gene has been found to be close to 150 kb from the left (centric) end of the GART YAC. The GART gene itself is 40 kb in length (119); and the IFN-α receptor YAC is 160 kb. These numbers account for 350 kb of the 400 kb MluI fragment.

MHC Induction in Cell Lines Transformed by Fragmented YACs

To map more closely the location of the human Chromosome 21 accessory factor gene on the GART YAC and to facilitate its identification, a method was devised to fragment the GART YAC from its acentric end (105,106,113, 121). Briefly, a fragmentation vector was constructed which contains a BamHI-EcoRI fragment including an Alu sequence, a neo gene, a URA3 gene and a telomere. Recombination of the Alu sequence with homologous sequences in the parental GART YAC produced truncated YACs which were selected on uracil-deficient plates. DNA was isolated and was characterized by pulsed-field gel electrophoresis. YAC size was generally found to range from 80 to 500 kb (FIG. 20). Several YACs were shown to contain the GART gene based upon hybridization to a $^{32}$P-labelled GART gene fragment (obtained from Dr. David Patterson). Virtually all of the fragmented YACs hybridized to pGC8. 10E6, a plasmid containing a unique 6.0 kb EcoRI fragment which maps to the 50 kb centric end of the parental GART YAC. Therefore, fragmentation occurred from the acentric end. The phenotype of the yeast transformants was determined to be Ura3$^+$, neo$^+$, Trp$^+$. These transformants were next fused to recipient 16-9 somatic cell hybrids which contained the human IFN-gamma receptor as well as the HLA-B7 gene. Antibiotic G418-resistant cells were assayed for Chromosome 21 accessory factor activity as previously described (110). As is shown in FIG. 20 and FIG. 21, cell lines J29/16-9, J28/16-9, J16/16-9 and J18/16-9 were responsive to Hu-IFN-gamma as seen by induction of MHC gene expression. However, cell lines J20/16-9 and J6/16-9 did not respond to IFN-gamma. These results indicate that the Chromosome 21 accessory factor gene is located within 150 kb from the centric end of the GART YAC. Restriction mapping of the YACs J20 and J18, both approximately 150 kb in size, indicated that these YACs are virtually identical in size (data not shown). However, two additional fusions of yeast cells containing YAC J20 have not produced IFN-gamma responsive cells. We therefore conclude that YAC J20 contains a small deletion relative to YAC J18 which inactivated the accessory factor gene. Yeast cells containing YAC J6 have been fused twice to 16-9 cells without isolation of any IFN-gamma responsive cells. In addition, one other 80 kb YAC was found to be inactive (data not shown). YACs less than 150 kb in size (i.e., with more than 390 kb of the acentric end deleted) were inactive. YAC J18 is the smallest YAC that retained accessory factor activity.

MHC class I induction as a function of IFN-gamma concentration with the cell lines produced by the fusions was examined. As shown in FIG. 22, half-maximal induction of MHC class I gene expression was elicited at IFN-gamma concentrations between 1 to 10 units/ml. Significant increases in MHC expression could be detected at 1 unit/ml. These responses are similar to those observed in human cells and hamster×human somatic cell hybrids containing human Chromosomes 21 (or 21q) and 6 (or the cloned Hu-IFN-gamma R) (97,98,107,117).

Transcriptional Activation

Because hamster interferon-induced genes have not been isolated, we next examined the induction of two transcription factors whose sequence is conserved in the hamster. The transcriptional activation of interferon-inducible genes has been shown to be stimulated by transcription factors which accumulate in the cytoplasm and migrate to the nucleus (114,122–124). Levels of transcription factor ISGF3-gamma have been shown to increase in the cytoplasm after IFN-gamma treatment (125). To determine how much of the IFN-gamma pathway is functional in the YAC cell lines, we measured ISGF3-gamma in IFN-gamma treated and untreated cells by gel retardation assays with labeled ISRE (114,122–124). As is shown in FIG. 23, ISGF3-gamma levels are not induced in J6/16-9 and 16-9 cells treated with IFN-gamma. However, IFN-gamma induced ISGF3-gamma in J18/16-9 cells. The reason for the high background in J6/16-9 cells is not clear. The unlabeled ISRE competitor oligonucleotide effectively competed out the ISGF3-gamma signal. We also examined the induction of GAF, which is induced much more rapidly than ISGF3-gamma. Incubation of 16-9, J6/16-9 and J 18/16-9 cells with IFN-gamma for 30 minutes induced GAF in the J18/16-9 cells but not in 16-9 and J6/16-9 cells. This is consistent with the ISGF3-gamma data. We also tested the cell line transformed by the parental GART YAC and found GAF induction in this case as well.

Antiviral Activity

The Hu-IFN-gamma receptor and Chromosome 21q have been shown to be sufficient for an antiviral (EMCV) response in CHO cells (110). In addition, the 3x1S cell line, containing only 1–3 Mb of Chromosome 21q, is also protected by Hu-IFN-gamma when challenged by EMCV (105). To determine whether the receptor and the accessory factor encoded on the YACs are sufficient to produce antiviral effects in CHO 16-9, J18/16-9 and J29/16-9 cells, the cells were challenged with EMCV after treatment with various interferons. Human IFN-β and IFN-αA/D(Bgl), were active in protecting the 16-9, J18/16-9 and J29/16-9 cells against EMCV (Table 7). However, even at >3250 units/ml, Hu-IFN-gamma was unable to induce any protection against EMCV on 16-9 and J18/16-9 lines (Table 7); at >13,000 units/ml, Hu-IFN-gamma was unable to induce any protection against EMCV on J29/16-9 cells. The 153B7-8 cell line transfected with the Hu-IFN-gamma R was found to have high antiviral activity against EMCV with half-maximal protection at 3 units/ml of IFN-gamma. This value closely agrees with the dose-response data for MHC induction in the 16-9 cell lines containing the YAC clones (FIG. 22). These data indicate that anti-EMCV responsiveness must require another human gene which is not present on either the J18 or J29 YAC. This gene is, however, located within the 1–3 Mb of Chromosome 21 since the 3x1S and 153B7-8 cells transfected with the human IFN-gamma receptor cDNA are protected from EMCV infection at similar levels of Hu-IFN-gamma (105). The 16-9 cells containing YACs J18 and J29 exhibited a slight increased sensitivity compared to parental 16-9 cells to both Hu-IFN-αA/D and Hu-IFN-β of about 2-fold and 4- to 6-fold, respectively. The significance of this increased sensitivity remains to be determined.

The present study localizes the human Chromosome 21 accessory factor to a position which is within 310 kb of the human IFN-α/β receptor gene. This estimate is derived from the fact that the YAC containing the IFN-α/β receptor gene is 160 kb in size and the J18 fragmented YAC, which encodes accessory factor activity, is 150 kb in size. The relationship between the accessory factor gene and the GART gene has not been established with precision; however, the GART gene is not encoded by J18 (data not shown). Precise localization of the accessory factor gene is not yet possible since we do not have any YACs which are larger than J6 (80 kb) and smaller than J18 (150 kb). J20, which is also 150 kb in size was negative for MHC induction in several assays. If these data result from the fact that YAC J20 is actually slightly more truncated than YAC J18, the accessory factor gene would have to be bounded by the right end of YAC J18. On the other hand, we cannot exclude that the inactivity of YAC J20 is due to a small internal deletion, undetectable by our gross restriction mapping analyses. We have assayed an additional small YAC which is the same size as J6 (J9, 80 kb). This YAC was also negative. Our present data indicate that the accessory factor gene could be located somewhere between 80 and 150 kb from the left (centric) end of the GART YAC.

Rather than examine a number of hamster interferon-induced genes (which have not been isolated) in this study, we examined two transcription factors which have been shown to be induced by IFN-gamma. ISGF3-gamma is a 48 kb protein which is the DNA binding component of ISGF3 ( ). Three other proteins associate with ISGF3-gamma to form ISGF3. The other transcription factor, gamma-activated factor (or GAF), is rapidly induced by IFN-gamma and binds to a DNA sequence different from that of ISGF3-gamma ( ). We found that there is a correlation between MHC class I inducibility and induction of ISGF3-gamma and GAF in the cell lines transformed by the fragmented YACs: the cell lines in which Hu-IFN-gamma can induce MHC class I surface antigens are also capable of inducing ISGF3-gamma and GAF in response to Hu-IFN-gamma (FIG. 23). This indicates that the Chromosome 21 accessory factor is required for ISGF3-gamma and GAF induction. The role of the accessory factor in this process may be direct or indirect. The accessory factor may be involved only in ligand binding and/or receptor internalization; alternatively, the accessory factor may interact directly with the interferon stimulated gene factors during signal transduction.

The observation that cells J18/16-9 and J29/16-9 are not protected from EMCV infection even in the presence of very high (>3,000 units/ml) IFN-gamma concentrations indicates that, although the accessory factor and the Hu-IFN-gamma R are adequate to induce MHC class I antigens and to activate the ISGF3-gamma and GAF pathways, an additional factor is required to generate resistance to EMCV. This factor is clearly not located within the J29 YAC. Examination of the parental GART YAC has also shown that this YAC is not sufficient to produce anti-EMCV activity when expressed in CHO cells (105). As is illustrated in FIG. 24, we have designated this Chromosome 21 accessory factor that induces MHC class I antigens and transcription factor ISGF3-gamma as AF-1. The factor which is also encoded on Chromosome 21q and is required for EMCV resistance has been designated AF-2. AF-1 is clearly sufficient for ISGF3-gamma and MHC induction in J18/16-9 cells (FIGS. 20–23). Although AF-2 is required for the antiviral EMCV activity in response to Hu-IFN-gamma, it may function alone or together with AF-1. This will be clarified when the gene or cDNA for AF-2 is isolated. The accessory factor designated AF-3 was defined in a previous study (110) in which it was shown that CHO cells containing Chromosome 21q (and expressing both AF-1 and AF-2) are incapable of generating full VSV resistance in response to Hu-IFN-gamma. AF-3 is therefore located on a chromosome other than 21q. As with AF-2, although AF-3 is required for the antiviral VSV activity in response to Hu-IFN-gamma, AF-3 may function alone or together with AF-1 and/or AF-2. As is the case for AF-1, AF-2 and AF-3 are species-specific.

The conclusions obtained in this study with fragmented YACs which map to human Chromosome 21 should be compared with those recently reported by Kalina et al. (126) using human-mouse hybrid fibroblasts. These Chromosome 21-containing mouse fibroblasts transfected with Hu-IFN-gamma R cDNA were found to induce 2', 5'-oligoadenylate-synthetase, resist EMCV, and induce MHC class I antigens upon IFN-gamma treatment. However, when individual clones were examined it was found that EMCV protection was absent in 67% of the cloned cell lines. Therefore, the genes present on human Chromosome 21 are insufficient to produce EMCV protection and other unidentified genes are postulated to be involved. Our experiments with WA17 (a mouse×human somatic hybrid cell line which is trisomic for human Chromosome 21; reference 127) transfected with the Hu-IFN-gamma R failed to show anti-EMCV activity in response to human IFN-gamma (Y. Hibino, T. Mariano, B. Schwartz and S. Pestka, unpublished results). We have not succeeded in expressing the fragmented YACs in murine cells. Hence, we are not able so far to recreate the cellular assay systems employed in the present study in mouse cells. In any case, while the data of Kalina et al. (126) support the hypothesis that other species-specific proteins besides AF-1 are required for anti-EMCV activity, the present study identifies a factor (AF-2) encoded by Chromosome 21 which complements AF-1 to produce EMCV resistance. The species-specific proteins required for anti-EMCV activity in the mouse system cannot be AF-2 since they are not on Chromosome 21.

In summary, the fact that a specific chromosomal fragment containing a gene for AF-1, which is functional in CHO cells (as judged by MHC class I induction), is not sufficient for either anti-EMCV or anti-VSV activities demonstrates that other factors are required in order to produce the full spectrum of IFN-gamma activities. Our results define the existence of at least three accessory factors AF-1, AF-2 and AF-3 which are required for functional activity in response to Hu-IFN-gamma and its receptor, including MHC class I ISGF3-gamma and GAF induction, as well as anti-EMCV and anti-VSV activity. The full identification and characterization of these accessory factors will be necessary in order to understand how the IFN-gamma R signal transduction mechanism is regulated.

cDNA Clone Encoding an Accessory Factor

Screening of cDNA Libraries

The fragmented YAC clone J18 (150 kb) which was derived from YAC GART D142H8 (540 kb) by chromosomal fragmentation was shown to contain the gene encoding the accessory factor (65,70,71). Overlapping cosmid clones derived from GART D142H8 and J18 YACs were aligned as shown in FIG. 12 with a small gap of about 10 kb around the SfiI site proximal to the acentric vector arm. These cosmid clones were transfected into 16-9 cells in order to locate the gene more precisely. However, no transformants responding to Hu-IFN-gamma were observed.

In order to identify any transcripts encoded from the region of Chromosome 21 encompassed by the J18 YAC, Northern blots of polyA+ mRNA from 3x1S cells were probed with five individual cosmid inserts and each EcoRI subfragment of more than 6 kb from these cosmids. Suppression of hybridization to human repetitive sequences was accomplished with an excess of total human placental DNA as described under "Experimental Procedures." As shown in FIG. 13, we were able to identify one major transcript whose size is 1.8 kb with the 14 kb EcoRI fragment from cosmid GC8-10. The 14 kb DNA fragment was further digested with restriction endonuclease HindIII into 6 kb, 5 kb and 3 kb fragments each of which was used to probe the 3x1S polyA+ mRNA in a Northern blot. All three probes hybridized to the same transcript as did the 14 kb fragment but at different intensities, suggesting that coding sequences are scattered throughout the 14 kb fragment. Since the 5 kb fragment produced the strongest signal in the Northern blot hybridization, this fragment was chosen to screen the cDNA gamma library prepared from polyA+ RNA from 3x1S cells (73). Ten positive signals from 250,000 plaques were obtained by screening with the same hybridization conditions as used for Northern hybridization and each was isolated after plaque purification. Clones gamma 33-1 and gamma 42-2 contained the largest inserts and were used in subsequent experiments. Clone gamma 42-2 with a 1.6 kb insert was the longest clone. However, as the insert of this clone did not appear to have the beginning of an open reading frame and was shorter than the 1.8 kb size expected from the transcript, a 300 bp fragment (StiI and EspI) from the 5' end of clone gamma 42-2 was used to screen the Daudi plasmid pCDNA1 library. Nine positive clones were identified, purified and characterized. Clones pJS3 and pJS4 were found to have a 1.8 kb insert which is about the same size as the transcript identified.

In parallel experiments an oligonucleotide (5' GCTC-GAAGGCGTAGAGTGAC 3' SEQ ID No:15) homologous to the 5' end of clone 33-1 was synthesized and labeled with [$\alpha$-$^{32}$P]dATP with terminal deoxynucleotide transferase to a specific activity of $5 \times 10^9$ cpm/μg. It was used to screen about one million phages from the human M426 cell library (73). Six positive clones were identified and purified. The largest clone, gamma pCEV15-11, contained a 2.3 kbp insert, was sequenced and evaluated further for biological function. The plasmid rescued from phage gamma pCEV 15-11 was designated pSK1.

Sequencing of Hu-IFN-gamma AF-1 cDNA Clones

Both strands of the entire cDNA insert of plasmid pSK1 were sequenced as described under "Experimental Procedures." Since the sequences of the plasmids pJS3 and pJS4 were almost identical to the insert of plasmid pSK1, only one strand of these inserts was sequenced. The restriction maps of the DNA insert in clones pSK1 (gamma pCEV15-11) and pJS3 are shown in FIGS. 3A and B, respectively. The sequence of the insert of the Hu-IFN-gamma AF-1 clone (pSK1), which represented the largest of the cDNA sequences obtained, is shown in FIG. 15A. Including a poly(A) stretch ot 39 residues, the cDNA insert of clone pSK1 consists of 2255 bases. The 2255 base-pair nucleotide sequence of the cDNA and the deduced amino acid sequence show an open reading frame of 1011 bases (FIG. 15A). The 5'-untranslated region of this clone consisted of 648 bases. The 3' untranslated region extended for an additional 557 bases terminating with a poly(A) tail. A conventional polyadenylation consensus sequence (AATAAA SEQ ID No:16) was found 29 bases upstream of the poly(A) tail.

The first initiation codon (ATG) of the largest open reading frame is located 649 bases downstream from the beginning of the cDNA (clone pSK1). This methionine (ATG, position 649) is followed by a sequence that appears to encode a hydrophobic signal peptide with a predicted cleavage site after amino acid 90. The cDNA encodes a protein of 337 amino acids ending with the termination codon TGA at position 1660. In addition to the putative $NH_2$-terminal signal peptide, hydropathy index computation of the translated sequence (FIG. 16) reveals a hydrophobic domain towards the carboxy terminus of the molecule (amino acids 248–273) compatible with a transmembrane domain. This region is followed by a sequence of overall basic residues, a feature common to the cytosolic face of the membrane-spanning segments of many proteins including the human and mouse IFN-gamma receptors (23,24). This suggests an exoplasmic orientation of the amino terminus and cytoplasmic orientation of the carboxyl terminus characteristic of a type I membrane protein (81). If the leader peptide consists of the first 27 amino acids, the extracellular domain consists of 220 amino acids from positions 28 to 247 (FIG. 15A). The intracellular domain is predicted to consist of 64 amino acids from positions 274 to 337, the carboxy terminus (FIG. 15A). There are six potential N-linked glycosylation sites, all on the extracellular domain (FIG. 15A). The high content of serine and threonine residues (15.1%) makes extensive O-linked glycosylation a possibility (82, 83). The amino acid composition of the complete (preprotein) and the putative mature Hu-IFN-gamma receptor AF-1 molecules are summarized in Table 5.

The DNA sequence of the cDNA insert in pJS3 (FIG. 21A) was almost identical to that of the insert in pSK1 (FIG. 21B). There was virtual identity between the sequences of the coding region except for nucleotide position 839 which was "G" in the pSK1 insert and an "A" (nucleotide 109) in the pJS3 insert. This corresponds to a substitution of Arg in pSK1 to Gln in pJS3 at amino acid 64 of the AF-1 coding sequence (FIGS. 4A and 4B). The DNA sequence of the coding region of plasmid pJS4 was identical to the of pJS3.

Demonstration of Hu-IFN-gamma Receptor Accessory Factor Function of the AF-1 cDNA Plasmids pSK1, pJS3 and pJS4 containing the cDNA for the accessory factor under control of the CMV promoter were expressed in 16-9 cells which express the Hu-IFN-gamma/R and the human HLA-B7 antigen (65). The parental 16-9 cells displayed very good class I HLA induction upon treatment with Hu-IFN-A/D (FIGS. 17A,B, panels A) and a slight negative response to 100 units/ml Hu-IFN-gamma (FIGS. 17A,B, panels B). The 16-9 cells transfected with plasmids pJS3 (FIG. 17A, panels C and D), pJS4 (FIG. 17B, panels C and D) and pSK1 (FIG. 17C) also exhibited a good response to Hu-IFN-A/D (FIGS. 17A,B, panels C; FIG. 17C, panel A). In addition, they also showed very good HLA class I antigen induction upon treatment with 100 units/ml Hu-IFN-gamma (FIGS. 17A,B, panels D) or 500 units/ml Hu-IFN-gamma (FIG. 17C, panel B). A similar response could be generated by treatment of the transfected cells with as little as 10 units/ml of Hu-IFN-gamma (data not shown). The data demonstrate the cDNA clone exhibits the accessory factor-1 (AF-1) function attributed to a sequence on human Chromosome 21: ability of cells to induce class I MHC antigens in response to Hu-IFN-gamma.

Activity of 16-9 Cells Transfected with Plasmids Expressing AF-1 It was reported that hamster/human somatic hybrid 153B7-8 cells (carrying chromosome 21q as its sole human chromosome) transfected with the Hu-IFN-gamma receptor cDNA are protected against EMCV infection and display an increase in class I HLA antigen expression upon treatment with Hu-IFN-gamma (20,25). Furthermore, since the 3x1S region of Chromosome 21q is sufficient to complement the Hu-IFN-gamma receptor tor class I HLA induction (65,22,46), we tested whether this cDNA clone (pJS3) encodes the accessory factor which confers protection against EMCV infection in response to Hu-IFN-gamma. Previous results indicated Chromosome 21q encodes the accessory factors for EMCV antiviral protection (20). However, 16-9 cells transformed with YAC-JS2 (65) or YAC J18 (71) that express the gene for the accessory factor for class I HLA antigen induction did not show any protection against EMCV. In accordance with these observations, the 16-9 cells expressing the AF-1 cDNA also did not confer upon the cells the ability to protect cells from EMCV or VSV infection in response to Hu-IFN-gamma (data not shown). These results indicate that there are at least two accessory factors on human Chromosome 21q: one is required for induction of MHC class I antigens; a second is required for protection against EMCV.

Comparison of Human IFN-gamma Receptor AF-1 to Other Protein Sequences

Computer-assisted searches of a sequence data bank (GenBank) demonstrated no significant major sequence homology of the AF-1 cDNA or the protein sequence with known sequences in the data bank. However, a comparison of the AF-1 protein sequence to that of the human and mouse IFN-gamma receptors (Hu-IFN-gamma R and Mu-IFN-gamma R), the human, mouse and bovine IFN-α receptors (Hu-, Mu- and Bo-IFN-αR) and the human CRF2-4 sequences revealed some overall structural homology of the sequences as previously delineated by Bazan (84,85). Conservation of the position of four cysteines residues is unveiled by the alignment (FIG. 18). There is a conserved tyrosine adjacent to the third conserved cysteine.

It appears that AF-1 is a member of the class 2 receptor family (84,85). Amino acid comparison with other members of the class 2 receptor family were made: IFN-gamma R, mouse (24), human (23); IFN-αR, mouse (86), human (87), bovine (88,89); and CRF2-4, human (90). Significant homology is seen (20–30%, Table 6) in the extracellular domains, and in the conserved portion of the transmembrane region. The AF-1 protein contains a single D200 domain consisting of D100A and D100B domains each of which is proposed to be organized in two β-sheets with 7 β-strands in each sheet similar to the extracellular domain of other class 2 cytokine receptors (84,85,91). There are a few strongly conserved residues in all members of this family (FIG. 18). Two pairs of conserved Cys residues are located at positions that allow for an N-terminal and C-terminal disulfide bridge (84,85). The conservation of two proline residues between the SD100A and SD100B /-sheet domains allows for relative conformational independence of the /-sheets and further supports the suggestion that AF-1 is a member of this receptor family. Positions of clusters of aromatic (W, F, Y) and hydrophobic (A, 1, L, V, M) residues are also conserved throughout the extracellular domain. The occurrence of an unmatched Cys residue at position 174 of AF-1 and corresponding Cys residue at positions 174 (mouse) and 167 (human) of the IFN-gamma Rs (FIG. 18, arrow, third alignment section) might allow for the formation of an intermolecular disulfide bridge before or during IFN-gamma binding and transduction of the signal for MHC class I induction. There are also aligned Cys residues at corresponding positions of the IFN-gamma/Rs (position 128, mouse; 122, human) and CRF2-4 (position 106) but not AF-1 (FIG. 18, arrow, second alignment section) that suggests that CRF2-4 may be another member of the IFN-gamma R complex or accessory factor family.

Northern Blot Analysis of AF-1

To determine the size of the human transcript for AF-1, blot hybridization was carried out with the polyA$^+$ RNA isolated from Raji, HL60 and 3x1S cells and the labeled human AF-1 cDNA as probe. The probe hybridized to a major transcript of 1.8 kb (FIG. 13). Minor transcripts of larger size were observed (2.3 kb and 4 kb). The 1.8 kbp cDNA inserts in plasmids pJS3 and pJS4 correspond to the 1.8 kb transcript. The 2.25 kbp cDNA insert in plasmid pSK1 corresponds to the 2.3 kb transcript. The presence of a single major transcript for AF-1 is consistent with it being the product of a single-copy gene.

We previously demonstrated that the Chromosome 21 accessory factor gene necessary for class I HLA antigen induction by Hu-IFN-gamma is located in a 150 kb region of human DNA (65,71). We now show that a cDNA clone encoded on a gene from the YAC clones previously identified exhibits full functional accessory factor-1 activity. We reported that the accessory factor required for VSV protection (designated AF-3) is different from that leading to EMCV protection (designated AF-2) after Hu-IFN-gamma treatment (20,65). The observation that a small segment of human chromosome 21q (3x1S region) in conjunction with the Hu-IFN-gamma receptor was sufficient to induce class I HLA antigen expression and EMCV protection with Hu-IFN-gamma initially suggested that the same accessory factor was involved in both activities (83). However, the observation that 16-9 cells transformed with several YACs (65,71) were not protected against EMCV challenge demonstrated that another accessory factor is necessary for this antiviral activity, or that both the antiviral factor and the class I MHC induction factor are required for this antiviral activity. Our data demonstrated that the distinct additional factor responsible for the EMCV antiviral effect present in the 3x1S region was not included in the YAC clones that exhibited accessory factor-1 (AF-1) activity (65,71). Similarly, the AF-1 cDNA does not confer EMCV or VSV protection to hamster cells in response to Hu-IFN-gamma.

The identification of cDNA clones encoding the AF-1 protein will help us to understand the interactions between the Hu-IFN-gamma receptor and the accessory factors. This study and our previous studies (17—17,20,65,46) demonstrate that accessory factor functions for class I MHC induction, protection of cells against EMCV infection and protection against VSV infection are mediated by different factors or a different combination of factors. We thus conclude that a family of accessory factors that mediate unique intracellular signals is associated with the IFN-gamma receptor. It is likely that the expression of these factors are qualitatively and quantitatively different in various tissues, a hypothesis that explains the varied responses of different cells and tissues to IFN-gamma.

It is significant that the AF-1 protein exhibits meaningful homology to other members of the class 2 receptor family (84,85) that is represented by IFN-gamma and IFN-gamma receptors as well as CRF2-4. Although we do not know the molecular mechanisms by which AF-1 enables Hu-IFN-gamma to transmit a signal in combination with the Hu-IFN-gamma R, previous results suggested that the extracellular domain of the Hu-IFN-gamma R interacts with AF-1 (17–19). Since AF-1 is a transmembrane protein, it is likely that the extracellular domains of the two proteins interact. The ultimate intracellular signal that initiates the cytoplasmic events expressed as class I MHC antigen induction, however, must be generated by both Hu-IFN-gamma R and AF-1. The molecular signals in response to Hu-IFN-gamma gamma R/AF-2 and Hu-IFN-gamma R/AF-3 must be different from those in response to Hu-IFN-gamma R/AF-1 in order to engender effects not seen with the Hu-IFN-gamma R/AF-1 combination alone. We do not know whether AF-1 is required for functional activity of AF-2 and AF-3 at this time. However, the identification and isolation of the AF-1 cDNA will facilitate analysis of these interactions.

Appendium of References

1. Wheelock, E. F. (1965) Interferon Like Virus Inhibitor Induced in Human Leukocytes by Phytohemagglutinin. Science 149:310–311.
2. Blalock, J. E., Georgiades J. A., Langford, M. P., and Johnson, H. M. (1980) Purified Human Immune Interferon is a More Potent Anticellular Agent Than Leukocyte or Fibroblast Interferon. Cell Immunol. 49:390–394.
3. Tyring, S., Kimpel, G. R., Fleischman, W. R., Jr., and Baron, S. (1982) Direct Cytolysis by Partially-purified Preparation of Immune Interferon. Int. J. Cancer 30:59–64.
4. Stone-Wolff, D. S., Yip, Y. K., Kelker, J. C., Le, J., Henriksen-Destefano, D., Rubin, B. Y., Rinderknecht, E., Aggarwal, B. B., and Vilcek, J. (1984) Interrelationships of Human Interferon-gamma- with Lymphotoxin and Monocyte Cytotoxin. J. Exp. Med. 159:828–843.
5. Pestka, S., Langer, J. A., Zoon, K. C., and Samuel, C. E. (1987) Interferons and Their Actions. Ann. Rev. Biochem. 56:727–777.
6. Trinchieri, G. and Perussia, B. (1985) Immune Interferon: A Pleiotropic Lymphokine with Multiple Effects. Immunol. Today 6:131–136.
7. Langer, J. A., and Pestka, S. (1988) Interferon Receptors. Immunol. Today 9:393–399.
8. Landolfo, S., and Garotta, G. (1991) IFN-gamma, a Lymphokine That Modulates Immunological and Inflammatory Responses. J. Immunol. Res. 3:81–94.
9. Rothermal, C. D., Rubin, B. Y., and Murray, H. W. (1983) Interferon-gamma is the Factor in Lymphokine that Activates Human Macrophages to Inhibit Intracellular Chlamydia psittaci Replication. J. Immunol. 131:2542–2544.
10. Finkelman, F. D., Katona, I. M., Mosmann, T. R., and Coffman, R. L. (1988) IFN-gamma Regulates the Isotypes of Ig Secreted During in vivo Humoral Immune Responses. J. Immunol. 140:1022–1027.
11. Rashidbaigi, A., Langer, J. A., Jung, V., Jones, C., Morse, H. G., Tischfield, J. A., Trill, J. J., Kung, H.-F., and Pestka, S. (1986) The Gene for the Human Immune Interferon Receptor is Located on Chromosome 6. Proc. Natl. Acad. Sci. U.S.A. 83:384–388.
12. Mariano, T. M., Kozak, C.A., Langer, J. A., and Pestka, S. (1987) The Mouse Immune Interferon Receptor Gene is Located on Chromosome 10. J. Biol. Chem. 262:5812–5814.
13. Levine, F., Erlich, H., Mach, B., Leach, R., White, R., and Pious, D. (1985) Deletion Mapping of HLA and Chromosome 6p Genes. Proc. Natl. Acad. Sci. U.S.A. 82:3741–3745.
14. Jung, V., Rashidbaigi, A., Jones. C., Tischfield, J. A., Shows, T. B., and Pestka, S. (1987) Human Chromosome 6 and 21 are Required for Sensitivity to Human Interferon Gamma. Proc. Natl. Acad. Sci. U.S.A. 84:4151–4155.
15. Jung, V., Jones, C., Rashidbaigi, A., Geyer, D. D., Morse, H. G., Wright, R. B., and Pestka, S. (1988) Chromosome Mapping of Biological Pathways by Fluorescence-activated Cell Sorting and Cell fusion: The Human Interferon Gamma Receptor as a Model System. Somat. Cell Mol. Genet. 14:583–592.
16. Hibino, Y., Mariano, T. M., Kumar, C. S., Kozak, C. A., and Pestka, S. (1991) Expression and Reconstitution of a Biologically Active Mouse Interferon Gamma Receptor in Hamster Cells: Chromosome Location of an Accessory Factor. J. Biol. Chem. 266:6948–6951.
17. Hibino, Y., Kumar, C. S., Mariano, T. M., Lai, D., and Pestka, S. (1992) Chimeric Interferon Gamma Receptors Demonstrate an Accessory Factor Required for Activity Interacts with the Extracellular Domain. J. Biol. Chem. 267:3741–3749.
18. Hemmi, S., Merlin, G., and Aguet, M. (1992) Functional Characterization of a Hybrid Human-mouse Interferon-gamma Receptor: Evidence for Species-specific Interaction of the Extracellular Receptor Domain with a Putative Signal Transducer. Proc. Natl. Acad. Sci. U.S.A. 89:2737–2741.
19. Gibbs, V. C., Williams, S. R., Gray, P. W., Schreiber, R. D., Pennica, D., Rice, G. and Goeddel, D. V. (1991) The Extracellular Domain of the Human Interferon Gamma Receptor Interacts with a Species-specific Signal Transducer. Mol. Cell Biol. 11:5860–5866.
20. Cook, J. R., Jung, V., Schwartz, B., Wang, P. and Pestka, S. (1992) Structural Analysis of the Human Interferon-gamma Receptor: Specific Requirement of a Small Segment of the lntracellilar Domain for Class I MHC Antigen Induction and Antiviral Activity. Proc. Natl. Acad. Sci. U.S.A. 89:11317–11321.
21. Farrar, M. A., Campbell, J. D., and Schreiber, R. D. (1992) Identification of a Functionally Important Sequence in the C Terminus of the Interferon-gamma Receptor. Proc. Natl. Acad. Sci. U.S.A. 89:8806–11710.
22. Langer, J. A., Rashidbaigi, A., Lat, L.-W., Patterson, D., and Jones, C. (1990) Sublocalization on Chromosome 21 of Human Interferon-α Receptor Gene and the Gene for an Interferon-gamma Response Protein. Somat. Cell Mol. Genet. 16:231–240.
23. Aguet, M., Dembic, Z., and Merlin, G. (1988) Molecular Cloning and Expression of the Human Interferon-gamma Receptor. Cell 55:273–280.
24. Kumar, C.S., Muthukumaran, G., Frost, L. J., Noe, M., Ahn, Y.-H., Mariano, T. M., and Pestka, S. (1989) Molecular Characterization of the Murine Interferon Gamma Receptor cDNA. J. Biol. Chem. 264, 17939–17946.
25. Jung, V., Jones, C., Kumar, C. S., Stefanos, S., O'connell, S., and Pestka, S. (1990) Expression and Reconstitution of a Biologically Active cDNA for the Human Interferon Gamma Receptor. J. Biol. Chem. 265:1827–1830.
26. Kalina, U., Ozman, L., Dadova, K. D., Gentz, R., and Garotta, G. (1993) The Human Gamma Interferon Receptor Accessory Factor Encoded by Chromosome 21 Transduces the Signal for the Induction of 2′,5′-Oligoadenylate-synthetase, Resistance to Virus Cytopathic Effect, and Major Histocompatibility Complex Class I Antigens. J. Virology 67:1702–1706.
27. Burke, D., Carle, G. F., and Olson, M. V. (1987) Cloning of Large Segments of Exogenous DNA into Yeast by Means of Artificial Chromosome Vectors. Science 236:806–812.
28. Green, E. D. and Olson, M. V. (1990) Systematic Screening of Yeast Artificial-chromosome Libraries by use of the Polymerase Chain Reaction. Proc. Natl. Acad. Sci. U.S.A. 87:1213–1217.
29. Gao, J., Erickson, P., Gardiner, K., LeBeau, M. M., Diaz, M. O., Patterson, D., Rowley, J. D., and Drabkin, H. A. (1991) Isolation of a Yeast Artificial Chromosome Spanning the 8;21 Translocation Breakpoint t(8;21) (q22; q22.3) in Acute Myelogenous Leukemia. Proc. Natl. Acad. Sci. U.S.A. 88:4882–4886.
30. D'Urso, M., Zucchi, I., Ciccodicola, A., Palmieri, G., Abidi, F., and Schlessinger, D. (1990) Human Glucose-6-phosphate Dehydrogenase Gene Carried on a Yeast Artificial Chromosome Encodes Active Enzyme in Monkey Cells. Genomics 7:531–534.
31. Huxley, C., Hagino, Y., Schlessinger, D., Olson, M. V. (1991) The Human HPRT Gene on a Yeast Artificial Chromosome is Functional when Transfected to Mouse Cells by Cell Fusion. Genomics 9:742–750.
32. Gnirke, A., Barnes, T. S., Patterson, D., Schild, D., Featherstone, T., and Olson, M. V. (1991) Cloning and in vivo Expression of the Human GART Gene using Yeast Artificial Chromosomes. The EMBO J. 10:1629–1634.
33. Pavan, W. J., Hieter, P., and Reeves, R. H. (1990) Modification and Transfer into an Embryonal Carcinoma Cell Line of a 360-kilobase Human-derived Yeast Artificial Chromosome. Mol. Cell. Biol. 10:4163–4169.
34. Pachnis, V., Pevny, L., Rothstein, R., and Costantini, F. (1990) Transfer of a Yeast Artificial Chromosome Carrying Human DNA from Saccharomyces cerevisiae into Mammalian Cells. Proc. Natl. Acad. Sci. U.S.A. 87:5109–5113.
35. Yoshi, O., Schmidt, H., Reddy, E. S. P., Weissman, S., and Lengyel, P. (1982) Mouse Interferons Enhance the Accumulation of a Human HLA RNA and Protein in Transfected Mouse and Hamster Cells. J. Biol. Chem. 257:13169–13172.
36. Yoshie, O., Schmidt, H., Lengyel, P., Reddy, E. S. P., Morgan, W. R., and Weissman, S. M. (1984) Transcripts of Human HLA Gene Fragments Lacking the 5′-terminal Region in Transfected Mouse Cells. Proc. Natl. Acad. Sci. U.S.A. 81:649–653.
37. Rehberg, E., Kelder, B. Hoal, E. G., and Pestka, S. (1982) Specific Molecular Activities of Recombinant and Hybrid Leukocyte Interferons. J. Biol. Chem. 257:11497–11502.
38. Barnstable, C. J., Bodiner, W. F., Brown, G., Galfre, G., Milstein, C., Williams, A. F., and Zeigler, A. (1978) Production of Monoclonal Antibodies to Group A Erythrocytes, HLA and Other Human Cell Surface Antigens—New Tools for Genetic Analysis. Cell 14:9–20.
39. Rose, M. D., Winston, F., and Hieter, P. (1990) Methods in Yeast Genetics, A Laboratory Course Manual. Cold Spring Harbor Laboratory Press, pp. 119–123.
40. Smith, C. L., Lawrance, S. K., Gillespie, G. A., Cantor, C. R., Weissman, S. M., and Collins, F. S. (1987) Strategies for Mapping and Cloning Macroregions of Mammalian Genomes. Methods in Enzmology 151:461–489.
41. Feinberg, A. P., and Vogelstein. B. (1983) A Technique for Radiolabeling DNA Restriction Endonuclease Fragments to High Specific Activity. Anal. Biochem. 132:6–13.

42. Familletti, P. C., Rubinstein, S., and Pestka, S. (1981) A Convenient and Rapid Cypopathic Effect Inhibition Assay for Interferon. Methods Enzymol. 78:387–394.
43. Lutfalla, G., Roeckel, N., Mogensen, K. E., Mattei, M.-G., and Uzé, G. (1990) Assignment of Human Interferon-α Receptor Gene to Chromosome 21q22.1 by in situ Hybridization. J. Interferon Res. 10:515–517.
44. Lutfalla, G., Gardiner, K., Proudhon, D., Vielh, E., Uzé, G. (1992) The Structure of the Human Interferon α/β Receptor Gene. J. Biol. Chem. 267:2802–2809.
45. Mariano, T. M., Donnelly, R. J., Soh, J. and Pestka, S. (1992) "Structure and Function of the Type I Interferon Receptor." in Interferon: Principles and Medical Applications, (S. Baron, D. Coppenhaver, F. Dianzani, W. R. Fleischman, T. K. Hughes, G. R. Klimpel, D. W. Niesel, G. J. Stanton and S. K. Tyring, eds.), Univ. Texas Medical Branch at Galveston, Galveston, Tex., pp. 129–138.
46. Jung, V. (1991) The Human Interferon Gamma Receptor and Signal Transduction. Ph.D. thesis submitted to the Graduate School—New Brunswick, Rutgers, The State University of New Jersey, and the Graduate School of Biomedical Sciences, Robert Wood Johnson Medical School.
47. McCormick, M. K., Shero, J. H., Connelloy, C. J., Antonarakis, S. E., and Hieter, P. (1990) "Methods for Cloning Large DNA Segments as Artificial Chromosomes in S. cerevisiae, In: Technique-A J. of Methods in Cell and Molecular Biology 2:65–71.
48. Pavan, W. J., Hieter, P., and Reeves, R. H. (1990) Generation of Deletion Derivatives by Targeted Transforniation of Human-derived Yeast Artificial Chromosomes. Proc. Natl. Acad. Sci. U.S.A. 87:1300–1304.
49. Soh, J., Mariano, T. M., Bradshaw, G., Donnelly, R. J., and Pestka, S. (in preparation).
50. Duyk, G. M., Kim, S., Myers, R. M., and Cox, D. R. (1990) Exon Trapping: A Genetic Screen to Identify Candidate Transcribed Sequences in Cloned Mammalian Genomic DNA. Proc. Natl. Acad. Sci. U.S.A. 87:8995–8999
51. Lovett, M., Kere, J., and Hinton, L. M. (1991) Direct Selection: A Method for the Isolation of cDNAs Encoded by Large Genomic Regions. Proc. Natl. Acad. Sci. U.S.A. 88:9628–9632.
52. Elvin, P., Slynn, G., Black, D., Graham, A., Butler, R., Riley, J., Anand, R., and Markham, A. F. (1990) Isolation of cDNA Clones Using Yeast Artificial Chromosome Probes. Nucleic Acid. Res. 18:3913–3917.
53. Chumakov, I., Rigault, P., Guillou, S., Ougen, P., Billaut, A., Guasconi, G., Gervy, P., Le Gall, I., Soularue, P., Grinas, L., Bougueleret, L., Bellanné-Chantelot, C., Lacroix, B., Barillot, E., Gesnouin, P., Pook, S., Vaysseix, G., Frelat, G., Schmitz, A., Sambucy, J.-L., Bosch, A., Estivill, X., Weissenbach, J., Vignal, A., Riethman, H., Cox, D., Patterson, D., Gardiner, K., Hattori, M., Sakaki, Y., Ichikawa, H., Ohki, M., Paslier, L. D., Heilig, R., Antonarakis, S., Cohen, D. (1992) Continuum of Overlapping Clones Spanning the Entire Human Chromosome 21q. Nature 359:380–386.
54. Allshire, C. R., Cranston, G. Gosden, R. J., Maule, C. J., Hastie, D. N., and fantes, A. P. (1987) A Fission Yeast Chromosome can Replicate Autonomously in Mouse Cells. Cell 50:391–403.
55. Burke, D., Carle, G. F., and Olson, M. V. (1987) Cloning of Large Segment of Exogenous DNA into Yeast by Means of Artificial Chromosome Vectors. Science 236:806–812.
56. Burke, D. (1990) YAC Cloning: Options and Problems. GATA 7:94–99.
57. Jung, V. (1991). Ph.D. thesis (Rutgers Univ., Piscataway, N.J.).
58. Lewis, B. C., Shar, N. P., Braun. B. S., and Denny, C. T. (1992) Creation of a Yeast Artificial Chromosome Fragmentation Vector Based on Lysine-2. GATA 9:86–90.
59. Little, D. R., Porta, G., Carle, F. G., Schessinger, D., and D'Urso, M. (1989) Yeast Artificial Chromosome with 200- to 800-kilobase Inserts of Human DNA Containing HLA, V/5S, and Xq 24–Xq 28 Sequences. Proc. Natl. Acad. Sci. U.S.A. 86:1598–1602.
60. Pavan, J. W., Hieter, P. Sears, D., Burkhoff, A., and Reeves, R. (1991) High Efficiency Yeast Artificial Chromosome Fragment Vectors. Gene 106:125–127.
61. Sainz, J., Pevney, L., Wu, Y., Canter, R. C., and Smith, L. C. (1992) Distribution of Interspersed Repeats (Alu and Kpn) on Not I Restriction Fragments of Human Chromosome 21. Proc. Natl. Acad. Sci. U.S.A. 89:1080–1084.
62. Reeves, R. H., Pavan, W. J., and Hieter, P. (1990) Modification and Manipulation of Mammalian DNA Cloned as YACs. Genet. Anal. Tech. Appl. 7:107–113.
63. McCusker, J. H., and Davis, R. W. (1991). The Use of Proline as a Nitrogen Source Causes Hypersensitivity to, and Allows More Economical Use of 5FOA in Sacchacomyces cerevisiae. Yeast 7:607–608.
64. Kozak, C. A., Peyser, M., Krall, M., Mariano, T. M., Kumar, C. S., Pestka, S. and Mock, B. A. (1990) "Molecular Genetic Markers Spanning Mouse Chromosome 10, " Genomics 8, 519–524.
65. Soh, J., Donnelly, R. J., Mariano, T. M., Cook, J. R., Schwartz, B. and Pestka, S. (1993) "Identification of a YAC Clone Encoding an Accessory Factor for the Human Interferon Gamma Receptor: Evidence for Multiple Accessory Factors," Proc. Natl. Acad. Sci. U.S.A. (in press)
66. Kumar, C. S., Mariano, T. M., Noe, M. Deshpande, A. K., Rose, P. M. and Pestka, S. (1988) "Expression of the Murine Interferon gamma Receptor in Xenopus laevis Oocytes," J. Biol. Chem. 263, 13493–13496.
67. Emanuel, S. L. and Pestka, S. (1993) "Human Interferon-αA, α2 and α2(Arg) Genes in Genomic DNA," J. Biol. Chem. 268, 12565–12569.
68. Maniatis, T., Frisch, E. F. and Sambrook, J. (1989) *Molecular Cloning: A Laboratory Manual.* Three Volume Set, Cold Spring Harbor Laboratory, New York.
69. Blin, N. and Stafford, D. W. (1976) "A General Method for Isolation of High Molecular Weight DNA from Eukaryotes," Nucleic Acids Res. 3, 2303–2308.
70. Cook, J. R., Emanuel, S. L. and Pestka, S. (1993) "Yeast Artificial Chromosome Fragmentation Vectors Which Utilize Ura3[+] Selection," (submitted).
71. Cook, J. R., Emanuel, S. L., Donnelly, R. J., Soh, J., Mariano, T. M., Schwartz, B., Rhee, S. and Pestka, S. (1993) "Localization of the Human Interferon-gamma Receptor Accessory Factor Gene and Discovery of a New Accessory Factor by Chromosomal Fragmentation," (in preparation).
72. Miki, T., Fleming, T. P., Crescenzi, M., Molloy, C. J., Blam, S. B., Reynolds, S. H., and Aaronson, S. A. (1991) "Development of a highly efficient expression cDNA cloning system: application to oncogene isolation," Proc. Natl. Acad. Sci. USA 88, 5167–5171.
73. Miki, T., Matsui, T., Heidaran M. A. and Aaronson, S. A. (1989) "An Efficient Directional Cloning System to Construct cDNA Libraries Containing Full Length Inserts at High Frequency," Gene 83, 137–146.

74. Sanger, F., Nicklen, S. and Coulson, A. R. (1977) "DNA Sequencing with Chain-terminating Inhibitors," *Proc. Natl. Acad. Sci. USA* 74, 5463–5467.
75. Tabor, S. and Richardson, C. C. (1987) "DNA Sequence Analysis with a Modified Bacteriophage T7 DNA Polymerase," *Proc. Natl. Acad. Sci. USA* 84, 4767–4771.
76. Sealey, P. G., Whittaker, P. A. and Southern, E. M. (1985) "Removal of Repeated Sequences from Hybridisation Probes," *Nucl. Acids. Res.* 13, 1905–1922.
77. Devereux, J., Haeberli, P. and Smithies, O. (1984) "A Comprehensive Set of Sequence Analysis Programs for the Vax," *Nucl. Acids Res.* 12, 387–395.
78. Needleman, S. B. and Wunsch, C. D. (1970) "A General Method Applicable to the Search for Similarities in the Amino Acid Sequence of Two Proteins," *J. Mol. Biol.* 48, 443–453.
79. Kyte, J. and Doolittle, R. F. (1982) "A Simple Method for Displaying the Hydropathic Character of a Protein," *J. Mol. Biol.* 157, 105–132.
80. Rehberg, E., Kelder, B., Hoal, E. G., and Pestka, S. (1982) "Specific Molecular Activities of Recombinant and Hybrid Leukocyte Interferons," *J. Biol. Chem.* 257, 11497–11502.
81. Wickner, W. T. and Lodish, H. F. (1985) "Multiple Mechanisms of protein Insertion into and across Membranes," *Science* 230, 400–407.
82. Nikaido, T., Schimizu, A., Ishida, N., Sabe, H., Teshigawara, K., Maeda, M., Uchiyaina, T., Yodoi, J. and Honjo, T. (1984) "Molecular Cloning of cDNA Encoding Human Interleukin-2 Receptor," *Nature* 311, 631–635.
83. Russell, D. W., Schneider, W. J., Yamamota, T., Luskey, K. L., Brown, M. S. and Goldstein, J. L. (1984) "Domain Map of the LDL Receptor: Sequence Homology with the Epidermal Growth Factor Precursor," *Cell* 37, 577–585.
84. Bazan, J. F. (1990a) "Shared Architecture of Hormone Binding Domains in Type I and II Interferon Receptors," *Cell* 61, 753–754.
85. Bazan, J. F. (1990b) "Structural Design and Molecular Evolution of a Cytokine Receptor Super Family," *Proc. Natl. Acad. Sci. USA* 87, 6934–6938.
86. Uzé, G., Lutfalla, G., Bandu, M.-T., Proudhon, D. and Mogensen, K. E. (1992) "Behavior of a Cloned Murine Interferon α/β Receptor Expressed in Homospecific or Heterospecific Background," *Proc. Natl. Acad. Sci. USA* 89, 4774–4778.
87. Uzé, G., Lutfalla, G. and Gresser, I. (1990) "Genetic Transfer of a Functional Interferon α Receptor into Mouse Cells: Cloning and Expression of its cDNA," *Cell* 60, 225–234.
88. Mouchel-Vielh, E., Lutfalla, G., Mogensen, K. E., and Uzé, G. (1992) "Specific Antiviral Activities of the Human α-Interferons Are Determined at the Level of Receptor (IFNAR) Structure," *FEBS Lett.* 313, 255–259.
89. Lim, J.-K. and Langer, J. A. (1993) "Cloning and Characterization of a Bovine α-Interferon Receptor," *Biochem. Biophys. Acta* 1173, 314–319.
90. Lutfalla, G., Gardiner, K. and Uzé, G. (1993) "A New Member of the Cytokine Receptor Gene Family Maps on Chromosome 21 at Less Than 35 kb from IFNAR," *Genomics* 16, 366–373.
91. Thoreau, E., Petridou, B., Kelly, P. A. and Mornon, J. P. (1991) "Structural Symmetry of the Extracellular Domain of the Cytokine/Growth Hormone/Prolactin Receptor Family and Interferon Receptors Revealed by Hydrophobic Cluster Analysis," *FEBS Lett.* 282, 26–31.
92. Soh, J., Mariano, T. M., Bradshaw, G., Donnelly, R. J. and Pestka, S. (1993) "Generation of Random Internal Deletion Derivatives of YACs by *Homologous Targeting to Alu Sequences*," (submitted).
93. Gribskov, M. and Burgess, R. B. (1986) "Sigma Factors from *E. coli, B. subtilis*, Phage SP01, and Phage T4 are Homologous Proteins," *Nucleic Acids Res.* 14, 6745–6763.
94. Kumar, C. S., Muthukumaran, G., Frost, L. J., Noe, M., Ahn, Y.-H., Mariano, T. M., Rose, P. M., Kanter, P., and Pestka, S. (1989) "Molecular Characterization of the Murine Interferon Gamma Receptor cDNA," *J. Biol. Chem.* 264, 17939–17946.
95. Langer, J. A., and Pestka, S. (1988) "Interferon Receptors." *Immunology Today* 9, 393–400.
96. Rashidbaigi, A., Langer, J. A.. Jung, V., Jones, C., Morse, H. G., Tischfield, J. A., Trill, J. J., Kung, H.-F., and Pestka, S. (1986) "The Gene for the Human Immune Interferon Receptor is Located on Chromosome 6," *Proc. Natl. Acad. Sci. U.S.A.* 83, 384–388.
97. Jung, V., Rashidbaigi, A., Jones, C., Tischfield, J. A., Shows, T. B., and Pestka, S. (1987) "Human Chromosomes 6 and 21 are Required for Sensitivity to Human Interferon Gamma," *Proc. Natl. Acad. Sci. U.S.A.* 84, 4151–4155.
98. Jung, V. Jones, C. Rashidbaigi, A., Geyer, D. D., Morse, H. G., Wright, R. B., and Pestka, S. (1988) "Chromosome Mapping of Biological Pathways by Fluorescence-activated Cell Sorting and Cell Fusion: The Human Interferon Gamma Receptor as a Model System," *Somat. Cell Mol. Genet.* 14, 583–592.
99. Mariano, T. M., Kozak, C. A., Langer, J. A., and Pestka, S. (1987) "The Mouse Immune Interferon Receptor Gene is Located on Chromosome 10," *J. Biol. Chem.* 262, 5812–5814.
100. Hibino, Y., Mariano, T. M., Kumar, C. S., Kozak, C. A., and Pestka, S. (1991) "Expression and Reconstitution of a Biologically Active Mouse Interferon Gamma Receptor in Hamster Cells: Chromosomal Location of an Accessory Factor," *J. Biol. Chem.* 266, 6948–6951.
101. Hibino, Y., Kumar, C. S., Mariano, T. M., Lai, D., and Pestka, S. (1992) "Chimeric Interferon Gamma Receptors Demonstrate that an Accessory Factor Required for Activity Interacts with the Extracellular Domain," *J. Biol. Chem.* 267, 3741–3749.
102. Gibbs, V. C., Williams, S. R., Gray, P. W., Schreiber, R. D., Pennica, D., Rice, G.,and Goeddel, D. V. (1992) Mol. Cell. Biol. 11, 5860–5866.
103. Hemmi, S., Merlin, G., Aguet, M. (1992) Proc. Natl. Acad. Sci. U.S.A. 89, 2737–2741.
104. Langer, J. A., Rashidbaigi, A., Lai, L.-W., Patterson, D., And Jones, C. (1990) Somat. Cell Mol. Genet. 16, 321–240.
105. Soh, J., Donnelly, R. J., Mariano, T. M., Cook, J. R., Schwartz, B. and Pestka, S., (1993) "Identification of a YAC Clone Encoding an Accessory Factor for the Human Interferon Gamma Receptor: Evidence for Multiple Accessory Factors," Proc. Natl. Acad. Sci. U.S.A., in press.
106. Cook, J. R., Emanuel, S., and Pestka, S., "Yeast Artificial Chromosome Fragmentation Vectors Which Utilize Ura3[30] Selection," manuscript submitted.
107. Jung, V., Jones, C., Kumar, C. S., Stefanos, S., O'Connell, S., and Pestka, S. (1990) "Expression and Reconstitution of a Biologically Active Human Interferon Gamma Receptor in Hamster Cells," J. Biol. Chem. 265, 1827–1830.
108. Kung, H.-F., Pan, Y-C., Moschera, J., Tsai, K., Bekesi, E., Chang, M., Sugino, H., and Honda, S. (1986) Methods Enzymol. 119, 204–210.

109. Rehberg, E., Kelder, B., Hoal, E. G., and Pestka, S. (1982) "Specific Molecular Activities of Recombinant and Hybrid Leukocyte Interferons," J. Biol. Chem. 257, 11497–11502.
110. Cook, J. R., Jung, V., Schwartz, B., Wang, P, and Pestka, S. (1992) "Structural Analysis of the Human Interferon-gamma Receptor: Specific Requirement of a Small Segment of the Intracellular Domain for Class I MHC Antigen Induction and Antiviral Activity," Proc. Natl. Acad. Sci. U.S.A. 89, 11317–11321.
111. Friesen, H.-J., Stein, S., Evinger, M., Familletti, P., Moschera, J., Meienhofer, J., Shively, J., and Pestka, S. (1981) "Purification and Molecular Characterization of Human Fibroblast Interferon," Arch. Biochem. Biophys. 206 432–450.
112. Moschera, J. A., Woehlie, D., Tsai, K. P., Chen, C.-H., and Tarnowski, S. J. (1986) Methods in Enzymology 119, 177–183.
113. Pavan, W. J., Hieter, P., and Reeves, R. H. (1990) Mol. Cell. Biol. 10, 4163–4169.
114. Levy, D., Kessler, D. S., Pine, E., Darnell, J. E. (1989) Genes Dev. 3, 1362–1371.
115. Shuai, K. Schindler, C. Prezioso, V. R. and Darnell, J. E.,. Jr. (1992) "Activation of Transcription by IFN-gamma: Tyrosine Phosphorylation of a 91-kd DNA binding protein," Science 258, 1808–1812.
116. Familletti, P. C., Rubinstein, S., and Pestka, S. (1981) "A Convenient and Rapid Cytopathic Effect Inhibition Assay for Interferon," in Methods in Enzymology, Vol. 78 (S. Pestka, ed.), Academic Press, New York, 387–394.
117. Jung, V. (1991) Ph.D. Thesis (Rutgers University, Piscataway, N.J.).
118. Uzé, G., Lutfalla, G., Gresser, I. (1990) Cell 60, 225–234.
119. Cheng, S., Lutfalla, G., Uzé, G., Chumakov, I. M. and Gardiner, K. (1993) Mammalian Genome 4, 338–342.
120. Lutfalla, G., Gardiner, K. and Uzé, G. (1993) Genomics 16, 366–373.
121. Donnelly, R. J., Mariano, T. M., Cook, J. R., Bradshaw, G. L., Emanuel, S., Soh, J., O'Rear, J., and Pestka, S. (1992) "Development and Use of a YAC Fragmentation Vector to Map Human Chromosome 21," J. Interferon Res. 12, S216.
122. Levy, D. E., Kessler, D. S., Pine, R., Darnell, J. E. (1989) Genes Dev. 3 1362–1371.
123. Fu, X., Kessler, D. S., Veals, S. A., Levy, D. E., Darnell, J. E. (1990) Proc. Natl. Acad. Sci. U.S.A. 87, 8555–8559.
124. Schindler, C., Fu, X.-Y., Improta, R., Aebersold, J., Darnell, J. E. (1992) Science 257, 809–813.
125. Gutch, M. J., Daly, C., Reich, N. C. (1992) Proc. Natl. Acad. Sci. U.S.A. 89, 1141–1145.
126. Kalina, U., Ozmen, L., Di Padova, K., Gentz, R. and Garotta, G. (1993) J. Virol. 67, 1702–1706.
127. Raziuddin, A., Sarker, F. H., Dutkowski, R., Shulman, L., Ruddle, F. H., and Gupta, S. L. (1984) Proc. Natl. Acad. Sci. U.S.A. 81, 5504–5508.
128. Van Camp, G., Van Hul, W., Backhovens, H., Stinissen, P., Wehnert, A., Patterson, D., Vandenberghe, A., and Van Broeckhoven, C. (1990) Somatic Cell. Mol. Genet. 16, 241–249.

The invention being thus described, it will be obvious that the same may be varied in many ways. Such variations are not to be regarded as a departure from the spirit and scope of the invention and all such modifications are intended to be included within the scope of the following claims.

We claim:

1. Recombinant plasmid *Escherichia coli* DH5α (pSK1) having the deposit accession number ATCC 69390.

2. Recombinant plasmid *Escherichia coli* MC1061/p3 (pJS4) having the deposit accession number ATCC 69391.

3. Recombinant plasmid *Escherichia coli* MC1061/p3 (pJS3) having the deposit accession number ATCC 69392.

4. An isolated and purified polypeptide comprising the amino acid sequence of accessory factor-1 for human interferon gamma receptor as set out below MetArgProThrLeuLeuTrpSer-
LeuLeuLeuLeuLeuGlyValPheAlaA-
laAlaAlaAlaAlaProProAspPro-
LeuSerGlnLeuProAlaProGlnHisProLysIleArgLeu
TyrAsnAlaGluGlnValLeuSerTrpG-
luProValAlaLeuSerAsnSer-
ThrArgProValValTyrGlnValGln-
PheLysTyrThrAspSerLysTrpPheThrAlaAspIleMet
SerIleGlyValAsnCysThrGlnI-
LeThrAlaThrGluCysAspPheThrA-
laAlaSerProSerAlaGlyPheProMe-
tAspPheAsnValThrLeuArgLeuArgAlaGluLeuGlyAla
LeuHisSerAlaTrpValThrMetPro-
TrpPheGlnHisTyrArgAsnValThr-
ValGlyProProGluAsnIleGlu-
ValThrProGlyGluGlySerLeuIleIleArgPheSerSerPro
PheAspIleAlaAspThrSerThrAl-
aPhePheCysTyrTyrValHisTyrTrp-
GluLysGlyGlyIleGlnGlnValLysG-
lyProProPheArgSerAsnSerIleSerLeuAspAsnLeuLysPro
SerArgValTyrCysLeuGlnVal-
GlnAlaGlnLeuLeuTr-
pAsnLysSerAsnILePheArgValGly-
HisLeuSerAsnIleSerCysTyrGluThrMetAlaAspAla
SerThrGluLeuGlnGln-
ValIleLeuIleSerValGlyThrPhe-
SerLeuLeuSerValLeuAlaGlyAla-
CysPhePheLeuValLeuLysTyrArgGlyLeuIleLysTyr
TrpPheHisThrProProSerIlePro-
LeuGlnIleGluGluTyrLeuLysAsp-
ProThrGlnProIleLeuGluAla-
LeuAspLysAspSerSerProLysAspAspValTrpAspSer
ValSerIleIleSerPheProGluLys-
GluGlnGluAspValLeuGlnThrLeu SEQ ID.NO.1.

5. An isolated and purified polypeptide comprising the amino acid sequence of accessory factor-1 for human interferon gamma receptor as set out below MetArgProThrLeuLeuTrpSer-
LeuLeuLeuLeuLeuGlyValPheAlaA-
laAlaAlaAlaAlaProProAspPro-
LeuSerGlnLeuProAlaProGlnHisProLysIleArgLeu
TyrAsnAlaGluGlnValLeuSerTrpG-
luProValAlaLeuSerAsnSer-
ThrArgProValValTyrArgValGln-
PheLysTyrThrAspSerLysTrpPheThrAlaAspIleMet
SerIleGlyValAsnCysThrGlnIl-
LeThrAlaThrGluCysAspPheThrA-
laAlaSerProSerAlaGlyPheProMe-
tAspPheAsnValThrLeuArgLeuArgAlaGluLeuGly
AlaLeuHisSerAlaTrpValThrMet-
ProTrpPheGlnHisTyrArgAsn-
ValThrValGlyProProGluAsnILe-
GluValThrProGlyGluGlySerLeuILeILeArgPheSer
SerProPheAspIleAlaAspThrSer-
ThrAlaPhePheCysTyrTyrVal-
HisTyrTrpGluLysGlyGlyI-
leGlnGlnValLysGlyProPheArgSerAsnSerIleSerLeu
AspAsnLeuLysProSerArgValTyr-
CysLeuGlnValGlnAlaGln-
LeuLeuTrpAsnLysSerAsnIlePhe-
ArgValGlyHisLeuSerAsnIleSerCysTyrGluThrMet
AlaAspAlaSerThrGluLeuGlnGlnVal IleLeuIleSerVal-
GlyThrPheSerLeuLeuSerVal-
LeuAlaGlyAlaCysPhePheLeu-
ValLeuLysTyrArgGlyLeuIleLysTyrTrpPheHisThr
ProProSerIleProLeuGlnIleGlu-
GluTyrLeuLysAspProThrGln-
ProIleLeuGluAlaLeuAspLysAspS-
erSerProLysAspAspValTrpAspSerValSerIleIleSer
PheProGluLysGluGlnGluAspValLeuGlnThrLeu SEQ ID.NO.4.

\* \* \* \* \*

UNITED STATES PATENT AND TRADEMARK OFFICE
CERTIFICATE OF CORRECTION

PATENT NO.    : 6,287,853 B1                                    Page 1 of 1
DATED         : September 11, 2001
INVENTOR(S)   : Sidney Pestka et al.

It is certified that error appears in the above-identified patent and that said Letters Patent is hereby corrected as shown below:

Title page,
Item [54], the title reading "ACCESSORY FACTORY FUNCTION FOR INTERFERON GAMMA AND ITS RECEPTOR" should read -- ACCESSORY FACTOR FUNCTION FOR INTERFERON GAMMA AND ITS RECEPTOR --.

Column 1,
Line 3, insert the following:

-- GOVERNMENT RIGHTS
The research leading to the present invention was supported, in part, by the following grants from the National Institute of Health: CA46465. Accordingly, the United States Government may have certain rights in the invention. --

Signed and Sealed this

Twenty-fourth Day of June, 2003

JAMES E. ROGAN
*Director of the United States Patent and Trademark Office*